US006828330B2

(12) United States Patent
Walker et al.

(10) Patent No.: US 6,828,330 B2
(45) Date of Patent: Dec. 7, 2004

(54) QUINUCLIDINE-SUBSTITUTED HETERO-BICYCLIC AROMATIC COMPOUNDS FOR THE TREATMENT OF DISEASE

(75) Inventors: Daniel Patrick Walker, Kalamazoo, MI (US); Donn G. Wishka, Kalamazoo, MI (US); David W. Piotrowski, Portage, MI (US); Vincent E. Groppi, Jr., Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/163,565

(22) Filed: Jun. 6, 2002

(65) Prior Publication Data

US 2003/0073707 A1 Apr. 17, 2003

Related U.S. Application Data

(60) Provisional application No. 60/373,496, filed on Apr. 18, 2002, provisional application No. 60/328,548, filed on Oct. 11, 2001, provisional application No. 60/297,633, filed on Jun. 12, 2001, provisional application No. 60/297,632, filed on Jun. 12, 2001, provisional application No. 60/297,631, filed on Jun. 12, 2001, provisional application No. 60/297,630, filed on Jun. 12, 2001, and provisional application No. 60/297,629, filed on Jun. 12, 2001.

(51) Int. Cl.[7] .................... A61K 31/439; C07D 453/02

(52) U.S. Cl. .................. 514/305; 546/133; 546/115; 546/114; 546/113; 514/303; 514/302; 514/301; 514/300; 514/299

(58) Field of Search .................. 514/305, 303, 514/302, 301, 300, 299; 546/133, 113, 114, 115

(56) References Cited

U.S. PATENT DOCUMENTS

| 4,612,319 A | 9/1986 | King .......................... 514/305 |
| 4,721,720 A | 1/1988 | Wootton et al. ............. 514/304 |
| 4,797,406 A | 1/1989 | Richardson et al. ........ 514/299 |
| 4,798,829 A | 1/1989 | King et al. .................. 514/214 |
| 4,803,199 A | 2/1989 | Donatsch et al. ........... 514/214 |
| 4,822,795 A | 4/1989 | King .......................... 514/214 |
| 4,835,162 A | 5/1989 | Abood ........................ 514/305 |
| 4,863,919 A | 9/1989 | Smith .......................... 514/214 |
| 4,882,327 A | 11/1989 | King .......................... 514/214 |
| 4,888,353 A | 12/1989 | Lednicer et al. ............ 514/422 |
| 4,910,193 A | 3/1990 | Buchheit .................... 514/216 |
| 4,920,127 A | 4/1990 | King et al. .................. 514/278 |
| 4,920,219 A | 4/1990 | Pelletier et al. ............. 540/523 |

(List continued on next page.)

FOREIGN PATENT DOCUMENTS

| DE | 3810552 A1 | 3/1988 | ......... C07D/451/12 |
| EP | 0279512 A2 | 1/1988 | .......... A61K/31/46 |
| EP | 0279512 B1 | 1/1988 | .......... A61K/31/46 |
| EP | 0322016 A1 | 12/1988 | ......... C07D/519/00 |
| EP | 0403882 A2 | 6/1990 | ......... C07D/451/02 |
| EP | 0457243 A1 | 5/1991 | ......... C07D/451/04 |
| EP | 0483836 A1 | 10/1991 | ......... C07D/519/00 |
| EP | 0485962 A2 | 11/1991 | ......... C07D/519/00 |
| EP | 0496064 A1 | 12/1991 | ......... C07D/405/02 |
| EP | 0512350 A2 | 4/1992 | ......... C07D/453/02 |
| WO | WO 90/14347 | 5/1990 | ......... C07D/453/02 |
| WO | WO 91/09593 | 12/1990 | .......... A61K/31/00 |
| WO | WO 91/17161 | 4/1991 | ......... C07D/451/14 |
| WO | WO 92/10494 | 12/1991 | ......... C07D/451/00 |
| WO | WO 95/27490 | 4/1995 | ......... A61K/31/445 |
| WO | WO 96/33186 | 4/1996 | ......... C07D/405/12 |
| WO | WO 97/35860 | 3/1997 | ......... C07D/451/14 |
| WO | WO 00/73431 A2 | 5/2000 | .......... C12N/15/00 |
| WO | WO 01/36417 A1 | 11/2000 | ......... C07D/451/04 |
| WO | WO 01/60821 A1 | 2/2001 | ......... C07D/453/02 |

OTHER PUBLICATIONS

William R. Kem, *The brain a7 nicotinic receptor may be an important therapeutic target for the treatment of Alzheimer's disease: studies with DMXBA (GTS–21)*, Bihavioural Brain Research, 113 (2000), pp. 169–181.

John E. Macor, et al., *The 5–HT3 Antagonist Tropisetron (ICS 205–930) is a Potent and Selective a7 Nicotinic Receptor Partial Agonist*, Bioorganic & Medicinal Chemistry Letters, 11 (2001) pp. 319–321.

Aurelio Orjales, et al., *Benzimidazole–2–carboxylic acid amides and esters: a new structural class of 5–HT3 ligands*, Eur. J. Med. Chem, 34 (1999), pp. 451–422.

Primary Examiner—Charanjit S. Aulakh
(74) Attorney, Agent, or Firm—Mary J. Hosley

(57) ABSTRACT

The invention provides compounds of Formula I:

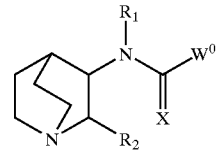

Formula I wherein $W^0$ is a bicyclic moiety and is

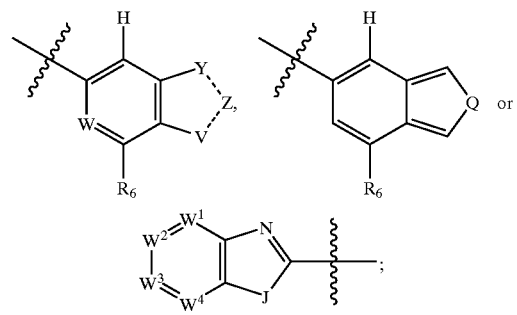

These compounds may be in the form of pharmaceutical salts or compositions, may be in pure enantiomeric form or racemic mixtures, and are useful to treat diseases or conditions in which α7 is known to be involved.

63 Claims, No Drawings

U.S. PATENT DOCUMENTS

| | | | |
|---|---|---|---|
| 4,920,227 A | 4/1990 | Pelletier et al. | 546/133 |
| 4,921,982 A | 5/1990 | Cohen et al. | 549/462 |
| 4,924,010 A | 5/1990 | Youssefyeh et al. | 549/355 |
| 4,933,445 A | 6/1990 | Pelletier et al. | 540/552 |
| 4,935,511 A | 6/1990 | Youssefyeh et al. | 540/552 |
| 4,937,247 A | 6/1990 | King | 514/299 |
| 4,973,594 A | 11/1990 | Tyers | 514/299 |
| 4,983,600 A | 1/1991 | Ward et al. | 514/214 |
| 4,985,437 A | 1/1991 | Tyers | 514/304 |
| 5,001,133 A | 3/1991 | Richardson et al. | 514/304 |
| 5,039,680 A | 8/1991 | Imperato et al. | 514/304 |
| 5,063,231 A | 11/1991 | Sanger et al. | 514/214 |
| 5,114,947 A | 5/1992 | Imondi | 514/282 |
| 5,175,173 A | 12/1992 | Sun | 514/305 |
| 5,183,822 A | 2/1993 | Van Wijngaarden et al. | 514/305 |
| 5,217,975 A | 6/1993 | Wadsworth et al. | 514/299 |
| 5,272,154 A | 12/1993 | Dixon et al. | 514/299 |
| 5,273,972 A | 12/1993 | Jagdmann et al. | 514/210 |
| 5,300,512 A | 4/1994 | Flynn et al. | 514/305 |
| 5,322,951 A | 6/1994 | King et al. | 548/312.1 |
| 5,342,845 A | 8/1994 | Chokai et al. | 514/305 |
| 5,352,685 A | 10/1994 | Maruyama et al. | 514/301 |
| 5,362,734 A | 11/1994 | Ward et al. | 514/294 |
| 5,362,740 A | 11/1994 | Bedeschi et al. | 514/299 |
| 5,434,161 A | 7/1995 | Becker et al. | 514/300 |
| 5,510,478 A | 4/1996 | Sabb | 540/585 |
| 5,556,851 A | 9/1996 | Maruyama et al. | 514/214 |
| 5,561,149 A | 10/1996 | Azria et al. | 514/397 |
| 5,599,937 A | 2/1997 | Glas et al. | 546/133 |
| 5,977,144 A | 11/1999 | Meyer et al. | 513/334 |
| 6,054,464 A | 4/2000 | Macor et al. | 514/299 |

QUINUCLIDINE-SUBSTITUTED HETERO-BICYCLIC AROMATIC COMPOUNDS FOR THE TREATMENT OF DISEASE

CROSS REFERENCE TO RELATED APPLICATIONS

This application claims the benefit of U.S. provisional application Ser. No. 60/297,629 filed on 12 Jun. 2001, under 35 USC 119(e)(i); U.S. provisional application Ser. No. 60/297,630 filed on 12 Jun. 2001, under 35 USC 119(e)(i); U.S. provisional application Ser. No. 60/297,631 filed on 12 Jun. 2001, under 35 USC 119(e)(i); U.S. provisional application Ser. No. 60/297,632 filed on 12 Jun. 2001, under 35 USC 119(e)(i); U.S. provisional application Ser. No. 60/297,633 filed on 12 Jun. 2001, under 35 USC 119(e)(i); U.S. provisional application Ser. No. 60/328,548 filed on Oct. 11, 2001, under 35 USC 119(e)(i); and U.S. provisional application Ser. No. 60/373,496 filed on 18 Apr. 2002, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

BACKGROUND OF THE INVENTION

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, Nature, 366(6454), p. 360–4, 1997). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., Nature, 366(6454), p 479–83, 1993), and the pore forming C-terminal domain of the 5-HT$_3$ receptor expressed well in Xenopus oocytes while retaining nicotinic agonist sensitivity. Eisele et al. used the N-terminus of the avian (chick) form of the α7 nAChR receptor and the C-terminus of the mouse form of the 5-HT$_3$ gene. However, under physiological conditions the α7 nAChR is a calcium channel while the 5-HT$_3$R is a sodium and potassium channel. Indeed, Eisele et al. teaches that the chicken α7 nAChR/mouse 5-HT$_3$R behaves quite differently than the native α7 nAChR with the pore element not conducting calcium but actually being blocked by calcium ions. WO 00/73431 A2 reports on assay conditions under which the 5-HT$_3$R can be made to conduct calcium. This assay may be used to screen for agonist activity at this receptor.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

SUMMARY OF THE INVENTION

The present invention discloses compounds of the Formula I:

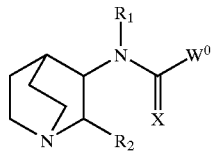

Formula I wherein W$^0$ is a bicyclic moiety and is

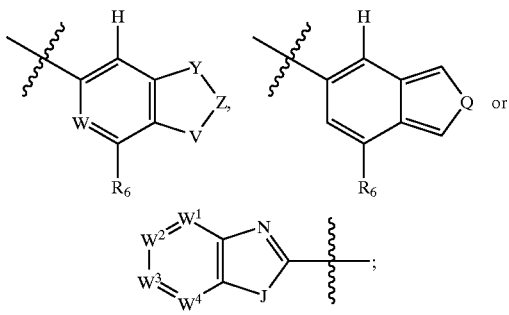

X is O, or S;

R$_1$ is H, alkyl, cycloalkyl, halogenated alkyl, substituted phenyl, or substituted naphthyl;

R$_2$ is H, alkyl, halogenated alkyl, substituted alkyl, cycloalkyl, or aryl;

R$_3$ is H, F, alkyl, halogenated alkyl, substituted alkyl, lactam heterocycloalkyl, phenoxy, substituted phenoxy, R$_7$, R$_9$, —N(R$_4$)-aryl, —N(R$_4$)-substituted phenyl, —N(R$_4$)-substituted naphthyl, —O-substituted phenyl, —O-substituted naphthyl, —S-substituted phenyl, —S-substituted naphthyl, or alkyl substituted on the ω carbon with R$_{15}$ where said ω carbon is determined by counting the longest carbon chain of the alkyl moiety with the C-1 carbon being the carbon attached to the bicyclic moiety W$^0$ and the ω carbon being the carbon furthest, e.g., separated by the greatest number of carbon atoms in the chain, from said C-1 carbon;

W is C(H) where

V—Z—Y is selected from O—C(R$_3$)=N, O—C(R$_5$)(R$_3$)—N(R$_4$), O—C(R$_5$)(R$_3$)—S, O—N=C(R$_5$), O—C(R$_3$)(R$_8$)—O, O—C(R$_3$)(R$_5$)—O, S—C(R$_3$)=N, S—C(R$_5$)(R$_3$)—N(R$_4$), S—N=C(R$_5$), N=C(R$_3$)—O, N=C(R$_3$)—S, N=C(R$_3$)—N(R$_4$), N(R$_4$)—N=C(R$_5$), N(R$_4$)—C(R$_5$)(R$_3$)—O, N(R$_4$)—C(R$_5$)(R$_3$)—S, N(R$_4$)—C(R$_5$)(R$_3$)—N(R$_4$), C(R$_4$)$_2$—O—N(R$_4$), C(R$_5$)$_2$—N(R$_4$)—O, C(R$_5$)$_2$—N(R$_4$)—S, C(R$_5$)=N—O, C(R$_5$)=N—S, C(R$_5$)=N—N(R$_4$), C(R$_5$)$_2$—O—C(R$_5$)$_2$, C(R$_5$)$_2$—S—C(R$_5$)$_2$, C(R$_5$)$_2$—N(R$_4$)—C(R$_5$)$_2$, C(R$_5$)(R$_{17}$)—C(R$_3$)(R$_{17}$)—C(R$_5$)(R$_{17}$), or C(R$_5$)$_2$—C(R$_3$)(R$_5$)—C(R$_5$)—C(R$_5$)$_2$;

Q is N(R$_{19}$), O, or S;

W is N where

V—Z—Y is selected from O—C(R$_3$)=N, O—C(R$_5$)(R$_3$)—N(R$_4$), O—C(R$_5$)(R$_3$)—S, O—N=C(R$_5$) O—C(R$_3$)(R$_5$)—O, S—C(R$_3$)=N, S—C(R$_5$)(R$_3$)—N(R$_4$), S—N=C(R$_5$), N=C(R$_3$)—O, N=C(R$_3$)—S, N=C(R$_3$)—N(R$_4$), N(R$_4$)—N=C(R$_5$), N(R$_4$)—C(R$_5$)(R$_3$)—O, N(R$_4$)—C(R$_5$)(R$_3$)—S, N(R$_4$)—C(R$_5$)(R$_3$)—N(R$_4$), C(R$_5$)$_2$—O—N(R$_4$), C(R$_5$)$_2$—N(R$_4$)—O C(R$_5$)$_2$—N(R$_4$)—S, C(R$_5$)=N—O, C(R$_5$)=N—S, C(R$_5$)=N—N(R$_4$), C(R$_5$)=C(R$_3$)—C(R$_5$)$_2$, or C(R$_5$)$_2$—C(R$_3$)(R$_5$)—C(R$_5$)$_2$;

W$^1$, W$^2$, W$^3$, W$^4$ are each independently N or C(R$_{21}$), provided that no more than two of W$^1$, W$^2$, W$^3$, W$^4$ are N, and further provided when more than two of W$^1$, W$^2$, W$^3$, W$^4$ are C(R$_{21}$) that no more than two R$_{21}$ are other than H;

J is N(R$_{23}$), S, or O;

R$_4$ is H, or alkyl;

R$_5$ is H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)N(R$_{16}$)$_2$, —NHR$_1$, —NR$_1$COR$_{16}$, —N(R$_{10}$)$_2$, —SR$_1$, —C(O)R$_{16}$, —CO$_2$R$_1$, aryl, R$_7$, or R$_9$;

R$_6$ is H, F, Cl, Br, I, —CN, —CF$_3$, —OR$_{16}$, —SR$_{16}$, or —N(R$_{16}$)$_2$;

R$_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from R$_{20}$ and further having 0–3 substituents independently selected from F, Cl, Br, or I, or R$_7$ is 9-membered fused-ring moieties having a 6-membered ring fused to a 5-membered ring and having the formula

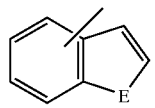

wherein E is O, S, or NR$_{19}$,

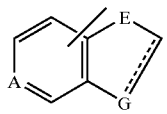

wherein E and G are independently selected from CR$_{18}$, O, S, N, or NR$_{19}$, and A is CR$_{18}$ or N, or

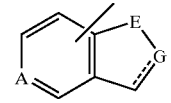

wherein E and G are independently selected from CR$_{18}$, O, S, N, or NR$_{19}$, and A is CR$_{18}$ or N, each 9-membered fused-ring moiety having 0–1 substituent selected from R$_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each R$_8$ is independently F, Br, Cl, I, alkyl, substituted alkyl, halogenated alkyl, alkenyl, substituted alkenyl, halogenated alkenyl, alkynyl, substituted alkynyl, halogenated alkynyl, —CN, —CF$_3$, —OR$_1$, —C(O)NH$_2$, —NHR$_1$, —SR$_1$, —CO$_2$R$_1$, aryl phenoxy, substituted phenoxy, heteroaryl, —N(R$_4$)-aryl, or —O-substituted aryl.

R$_9$ is 6-membered heteroaromatic mono-cyclic moieties containing within the ring 1–3 heteroatoms selected from =N— and having 0–1 substituent selected from R$_{20}$ and 0–3 substituent(s) independently selected from F, Cl, Br, or I, or R$_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from R$_{20}$ and 0–3 substituent(s) independently selected from F, Cl, Br, or I and having a bond directly or indirectly attached to the core molecule where valency allows;

Each R$_{10}$ is independently H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, or substituted phenyl;

Each R$_{11}$ is independently H, alkyl, cycloalkyl, heterocyclo-alkyl, halogenated alkyl, halogenated cycloalkyl, or halogenated heterocycloalkyl;

R$_{13}$ is —OR$_{11}$, —SR$_{11}$, —NR$_{11}$R$_{11}$, —C(O)R$_{11}$, —C(O)NR$_{11}$R$_{11}$, —CN, —CF$_3$, —NR$_{11}$C(O)R$_{11}$, —S(O)$_2$NR$_{11}$R$_{11}$, —NR$_{11}$S(O)$_2$R$_{11}$, or —NO$_2$;

R$_{15}$ is aryl, R$_7$, or R$_9$;

R$_{16}$ is H, alkyl, substituted alkyl, cycloalkyl, halogenated alkyl, heterocycloalkyl, substituted heterocycloalkyl, substituted phenyl, or substituted naphthyl;

One of R$_{17}$ is H, alkyl, substituted alkyl, halogenated alkyl, alkenyl, substituted alkenyl, halogenated alkenyl, alkynyl, substituted alkynyl, halogenated alkynyl, —CN, F, Br, Cl, I, —OR$_1$, —C(O)NH$_2$, —NHR$_1$, —SR$_1$, —CO$_2$R$_1$, aryl, R$_7$, or R$_9$, and each of the other two R$_{17}$ is independently selected from alkyl, substituted alkyl, halogenated alkyl, alkenyl, substituted alkenyl, halogenated alkenyl, alkynyl, substituted alkynyl, halogenated alkynyl, —CN, F, Br, Cl, I, —OR$_1$, —C(O)NH$_2$, —NHR$_1$, —SR$_1$, —CO$_2$R$_1$, aryl, R$_7$, or R$_9$;

Each R$_{18}$ is independently selected from H, F, Cl, Br, I, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

R$_{19}$ is H, alkyl, halogenated alkyl, substituted alkyl, cycloalkyl, halogenated cycloalkyl, substituted cycloalkyl, phenyl, or phenyl having 1 substituent selected from R$_{20}$ and further having 0–3 substituents independently selected from F, Cl, Br, or I;

R$_{20}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1-4 substituent(s) independently selected from F, Cl, Br, I, or R$_{13}$, cycloalkyl substituted with 1-4 substituent(s) independently selected from F, Cl, Br, I, or R$_{13}$, or heterocycloalkyl substituted with 1-4 substituent(s) independently selected from F, Cl, Br, I, or R$_{13}$;

R$_{21}$ is H, F, Cl, Br, I, alkyl, substituted alkyl, halogenated alkyl, cycloalkyl, —CN, —NR$_{22}$R$_{22}$, —OR$_{22}$, or —SR$_{22}$;

Each R$_{22}$ is independently H, alkyl, substituted alkyl, cycloalkyl, halogenated alkyl, substituted cycloalkyl, heterocycloalkyl, or substituted heterocycloalkyl;

R$_{23}$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, substituted phenyl, naphthyl, substituted naphthyl, R$_7$, or R$_9$;

or pharmaceutical composition, pharmaceutically acceptable salt, racemic mixture, or pure enantiomer thereof.

The compounds of Formula I are use to treat any one of or combination of cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, neurodegeneration associated with glaucoma, or symptoms associated with pain.

DETAILED DESCRIPTION OF THE INVENTION

Surprisingly, we have found that compounds of Formula I:

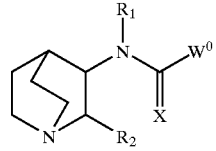

Formula I wherein W$^0$ is a bicyclic moiety and is

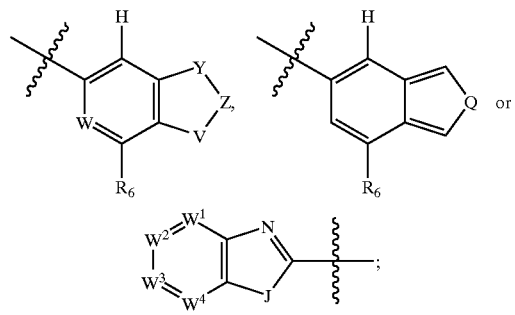

X is O, or S;

R$_1$ is H, alkyl, cycloalkyl, halogenated alkyl, substituted phenyl, or substituted naphthyl;

Alkyl is both straight- and branched-chain moieties having from 1–6 carbon atoms, unless otherwise specified;

Halogenated alkyl is an alkyl moiety having from 1–6 carbon atoms and having 1 to (2n+1) substituent(s) independently selected from F, Cl, Br, or I where n is the maximum number of carbon atoms in the moiety;

Cycloalkyl is a cyclic alkyl moiety having from 3–6 carbon atoms;

Substituted phenyl is a phenyl either having 1–4 substituents independently selected from F, Cl, Br, or I, or having 1 substituent selected from R$_{12}$ and 0–3 substituents independently selected from F, Cl, Br, or I;

Substituted naphthyl is a naphthalene moiety either having 1–4 substituents independently selected from F, Cl, Br, or I, or having 1 substituent selected from R$_{12}$ and 0–3 substituents independently selected from F, Cl, Br, or I, where the substitution can be independently on either only one ring or both rings of said naphthalene moiety;

R$_2$ is H, alkyl, halogenated alkyl, substituted alkyl, cycloalkyl, or aryl;

Aryl is phenyl, substituted phenyl, naphthyl, or substituted naphthyl;

Substituted alkyl is an alkyl moiety from 1–6 carbon atoms and having 0–3 substituents independently selected from F, Cl, Br, or I and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, —NO$_2$, R$_7$, R$_9$, phenyl, or substituted phenyl;

R$_3$ is H, F, alkyl, halogenated alkyl, substituted alkyl, lactam heterocycloalkyl, phenoxy, substituted phenoxy, R$_7$, R$_9$, —N(R$_4$)-aryl, —O-substituted phenyl, —O-substituted naphthyl, —S-substituted phenyl, —S-substituted naphthyl, or alkyl substituted on the ω carbon with $R_{15}$ where said ω carbon is determined by counting the longest carbon chain of the alkyl moiety with the C-1 carbon being the carbon attached to the bicyclic moiety $W^0$ and the ω carbon being the carbon furthest, e.g., separated by the greatest number of carbon atoms in the chain, from said C-1 carbon;

Lactam heterocycloalkyl is a cyclic moiety having from 4–7 atoms with one atom being only nitrogen with the bond to the lactam heterocycloalkyl thru said atom being only nitrogen and having a =O on a carbon adjacent to said nitrogen, and having up to 1 additional ring atom being oxygen, sulfur, or nitrogen and further having 0–2 substituents selected from F, Cl, Br, I, or $R_{14}$ where valency allows;

Substituted phenoxy is a phenoxy either having 1–3 substituents independently selected from F, Cl, Br, or I, or having 1 substituent selected from $R_{12}$ and 0–2 substituents independently selected from F, Cl, Br, or I;

W is C(H) where

V—Z—Y is selected from O—C($R_3$)=N, O—C($R_5$)($R_3$)—N($R_4$), O—C($R_5$)($R_3$)—S, O—N=C($R_5$), O—C($R_3$)($R_8$)—O, O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)$_2$—O—C($R_5$)$_2$, C($R_5$)$_2$—S—C($R_5$)$_2$, C($R_5$)$_2$—N($R_4$)—C($R_5$)$_2$, C($R_5$)($R_{17}$)—C($R_3$)($R_{17}$)—C($R_5$)($R_{17}$), or C($R_5$)$_2$—C($R_3$)($R_5$)—C($R_5$)$_2$;

Q is N($R_{19}$), O, or S;

W is N where

V—Z—Y is selected from O—C($R_3$)=N, O—C($R_5$)($R_3$)—N($R_4$), O—C($R_5$)($R_3$)—S, O—N=C($R_5$) O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)=C($R_3$)—C($R_5$)$_2$, or C($R_5$)$_2$—C($R_3$)($R_5$)—C($R_5$)$_2$;

$W^1$, $W^2$, $W^3$, $W^4$ are each independently N or C($R_{21}$), provided that no more than two of $W^1$, $W^2$, $W^3$, $W^4$ are N, and further provided when more than two of $W^1$, $W^2$, $W^3$, $W^4$ are C($R_{21}$) that no more than two $R_{21}$ are other than H;

J is N($R_{23}$), S, or O;

$R_4$ is H, or alkyl;

$R_5$ is H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)N($R_{16}$)$_2$, —NHR$_1$, —NR$_1$COR$_{16}$, —N($R_{10}$)$_2$, —SR$_1$, —C(O)R$_{16}$, —CO$_2$R$_1$, aryl, R$_7$, or R$_9$;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n–1) substituent(s) independently selected from F, Cl, Br, or I where n is the maximum number of carbon atoms in the moiety;

Substituted alkenyl is an unsaturated alkenyl moiety having from 2–6 carbon atoms and having 0–3 substituents independently selected from F, or Cl, and further having 1 substituent selected from —OR$_{10}$, —SR$_{10}$, —NR$_{10}$R$_{10}$, —C(O)R$_{10}$, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, —CN, R$_7$, R$_9$, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from F, Cl, Br, or I where n is the maximum number of carbon atoms in the moiety;

Substituted alkynyl is an unsaturated alkynyl moiety having from 3–6 carbon atoms and having 0–3 substituents independently selected from F, or Cl, and further having 1 substituent selected from —OR$_{10}$, —SR$_{10}$, —NR$_{10}$R$_{10}$, —C(O)R$_{10}$, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, —CN, R$_7$, R$_9$, phenyl, or substituted phenyl;

Halogenated cycloalkyl is a cyclic moiety having from 3–6 carbon atoms and having 1–4 substituents independently selected from F, or Cl;

Substituted cycloalkyl is a cyclic moiety having from 3–6 carbon atoms and having 0–3 substituents independently selected from F, or Cl, and further having 1 substituent selected from —OR$_{10}$, —SR$_{10}$, —NR$_{10}$R$_{10}$, —C(O)R$_{10}$, —CN, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, —NO$_2$, phenyl, or substituted phenyl;

Heterocycloalkyl is a cyclic moiety having 4–7 atoms with 1–2 atoms within the ring being —S—, —N($R_{19}$)—, or —O—;

Halogenated heterocycloalkyl is a cyclic moiety having from 4–7 atoms with 1–2 atoms within the ring being —S—, —N($R_{19}$)—, or —O—, and having 1–4 substituents independently selected from F, or Cl;

Substituted heterocycloalkyl is a cyclic moiety having from 4–7 atoms with 1–2 atoms within the ring being —S—, —N($R_{19}$)—, or —O— and having 0–3 substituents independently selected from F, or Cl, and further having 1 substituent selected from R$_7$, R$_9$, —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —NO$_2$, —S(O)$_2$NR$_{10}$R$_{10}$, —NR$_{10}$S(O)$_2$R$_{10}$, phenyl, or phenyl having 1 substituent selected from R$_{20}$ and further having 0–3 substituents independently selected from F, Cl, Br, or I;

$R_6$ is H, F, Cl, Br, I, —CN, —CF$_3$, —OR$_{16}$, —SR$_{16}$, or —N($R_{16}$)$_2$;

$R_7$ is 5-membered heteroaromatic mono-cyclic moieties containing within the ring 1–3 heteroatoms independently selected from the group consisting of —O—, =N—, —N($R_{19}$)—, and —S—, and having 0–1 substituent selected from R$_{20}$ and further having 0–3 substituents independently selected from F, Cl, Br, or I, or $R_7$ is 9-membered fused-ring moieties having a 6-membered ring fused to a 5-membered ring and having the formula

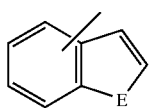

wherein E is O, S, or NR$_{19}$,

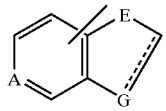

wherein E and G are independently selected from CR$_{18}$, O, S, N, or NR$_{19}$, and A is CR$_{18}$ or N, or

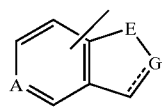

wherein E and G are independently selected from CR$_{18}$, O, S, N, or NR$_{19}$, and A is CR$_{18}$ or N, each 9-membered fused-ring moiety having 0–1 substituent selected from R$_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each R$_8$ is independently F, Br, Cl, I, alkyl, substituted alkyl, halogenated alkyl, alkenyl, substituted alkenyl, halogenated alkenyl, alkynyl, substituted alkynyl, halogenated alkynyl, —CN, —CF$_3$, —OR$_1$, —C(O)NH$_2$, —NHR$_1$, —SR$_1$, —CO$_2$R$_1$, aryl, phenoxy, substituted phenoxy, heteroaryl, —N(R$_4$)-aryl, or —O-substituted aryl.

R$_9$ is 6-membered heteroaromatic mono-cyclic moieties containing within the ring 1–3 heteroatoms selected from =N— and having 0–1 substituent selected from R$_{20}$ and 0–3 substituent(s) independently selected from F, Cl, Br, or I, or R$_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from R$_{20}$ and 0–3 substituent(s) independently selected from F, Cl, Br, or I and having a bond directly or indirectly attached to the core molecule where valency allows;

Each R$_{10}$ is independently H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, or substituted phenyl;

Each R$_{11}$ is independently H, alkyl, cycloalkyl, heterocyclo-alkyl, halogenated alkyl, halogenated cycloalkyl, or halogenated heterocycloalkyl;

R$_{12}$ is —OR$_{11}$, —SR$_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$;

R$_{13}$ is —OR$_{11}$, —SR$_{11}$, —NR$_{11}$R$_{11}$, —C(O)R$_{11}$, —C(O)NR$_{11}$R$_{11}$, —CN, —CF$_3$, —NR$_{11}$C(O)R$_{11}$, —S(O)$_2$NR$_{11}$R$_{11}$, —NR$_{11}$S(O)$_2$R$_{11}$, or —NO$_2$;

R$_{14}$ is alkyl, substituted alkyl, halogenated alkyl, —OR$_{11}$, —CN, —NO$_2$, —NR$_{10}$R$_{10}$;

R$_{15}$ is aryl, R$_7$, or R$_9$;

R$_{16}$ is H, alkyl, substituted alkyl, cycloalkyl, halogenated alkyl, heterocycloalkyl, substituted heterocycloalkyl, substituted phenyl, or substituted naphthyl;

One of R$_{17}$ is H, alkyl, substituted alkyl, halogenated alkyl, alkenyl, substituted alkenyl, halogenated alkenyl, alkynyl, substituted alkynyl, halogenated alkynyl, —CN, F, Br, Cl, I, —OR$_1$, —C(O)NH$_2$, —NHR$_1$, —SR$_1$, —CO$_2$R$_1$, aryl, R$_7$, or R$_9$, and each of the other two R$_{17}$ is independently selected from alkyl, substituted alkyl, halogenated alkyl, alkenyl, substituted alkenyl, halogenated alkenyl, alkynyl, substituted alkynyl, halogenated alkynyl, —CN, F, Br, Cl, I, —OR$_1$, —C(O)NH$_2$, —NHR$_1$, —SR$_1$, —CO$_2$R$_1$, aryl, R$_7$, or R$_9$;

Each R$_{18}$ is independently selected from H, F, Cl, Br, I, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

R$_{19}$ is H, alkyl, halogenated alkyl, substituted alkyl, cycloalkyl, halogenated cycloalkyl, substituted cycloalkyl, phenyl, or phenyl having 1 substituent selected from R$_{20}$ and further having 0–3 substituents independently selected from F, Cl, Br, or I;

R$_{20}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or R$_{13}$, cycloalkyl substituted with 1–4 substituent(s) independently selected from F, Cl, Br, I, or R$_{13}$, or heterocycloalkyl substituted with 1–4 substituent(s) independently selected from F, Cl, Br, I, or R$_{13}$;

R$_{21}$ is H, F, Cl, Br, I, alkyl, substituted alkyl, halogenated alkyl, cycloalkyl, —CN, —NR$_{22}$R$_{22}$, —OR$_{22}$, or —SR$_{22}$;

Each R$_{22}$ is independently H, alkyl, substituted alkyl, cycloalkyl, halogenated alkyl, substituted cycloalkyl, heterocycloalkyl, or substituted heterocycloalkyl;

R$_{23}$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, substituted phenyl, naphthyl, substituted naphthyl, $R_7$, or $R_9$; or pharmaceutical composition, pharmaceutically acceptable salt, racemic mixture, or pure enantiomer thereof useful to treat any one of or combination of cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, neurodegeneration associated with glaucoma, or symptoms associated with pain.

In another aspect, the invention includes methods of treating a mammal suffering from schizophrenia or psychosis by administering compounds of Formula I in conjunction with antipsychotic drugs. The compounds of Formula I and the antipsychotic drugs can be administered simultaneously or at separate intervals. When administered simultaneously the compounds of Formula I and the antipsychotic drugs can be incorporated into a single pharmaceutical composition. Alternatively, two separate compositions, i.e., one containing compounds of Formula I and the other containing antipsychotic drugs, can be administered simultaneously.

The present invention also includes the intermediates, the processes to make them and the compounds of the present invention, pharmaceutical compositions containing the active compounds, and methods to treat the identified diseases.

One group of compounds of Formula I includes compounds having the R configuration at the C3 position of the quinuclidine ring. Another group of compounds of Formula I includes compounds having the S configuration at the C3 position of the quinuclidine ring. Another group of compounds of Formula I includes compounds wherein the quinuclidine has S configuration at C2 when $R_2$ is other than H and at C2. Another group of compounds of Formula I includes compounds wherein the quinuclidine has 2S,3R configuration at C2 when $R_2$ is other than H at C2 with the amide-type bond being at C3.

Another group of compounds of Formula I includes compounds wherein X is O. Another group of compounds of Formula I includes compounds where $R_1$ is H. Another group of compounds of Formula I includes compounds wherein $R_2$ is H. Another group of compounds of Formula I includes compounds wherein $R_1$ is alkyl, cycloalkyl, halogenated alkyl, substituted phenyl, or substituted naphthyl. Another group of compounds of Formula I includes compounds wherein $R_2$ is alkyl. Another group of compounds of Formula I includes compounds wherein $R_2$ is methyl. Another group of compounds of Formula I includes compounds wherein $R_2$ is alkyl, halogenated alkyl, or substituted alkyl. Another group of compounds of Formula I includes compounds wherein $R_2$ is alkyl, halogenated alkyl, substituted alkyl, cycloalkyl, or aryl.

Another group of compounds of Formula I includes compounds wherein W is CH. Another group of compounds of Formula I includes compounds wherein W is CH and wherein V—Z—Y is O—C($R_3$)=N, O—C($R_5$)($R_3$)—N($R_4$), O—C($R_5$)($R_3$)—S, O—N=C($R_5$), O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)$_2$—O—C($R_5$)$_2$, C($R_5$)$_2$—S—C($R_5$)$_2$, C($R_5$)$_2$—N($R_4$)—C($R_5$)$_2$, or C($R_5$)$_2$—C($R_3$)($R_5$)—C($R_5$)$_2$.

Another group of compounds of Formula I includes compounds wherein W is CH and wherein V—Z—Y is independently any one of or combination of O—C($R_3$)=N, O—C($R_5$)($R_3$)—N($R_4$), O—C($R_5$)($R_3$)—S, O—N=C($R_5$), O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)$_2$—O—C($R_5$)$_2$, C($R_5$)$_2$—S—C($R_5$)$_2$, C($R_5$)$_2$—N($R_4$)—C($R_5$)$_2$, or C($R_5$)($R_{17}$)—C($R_3$)($R_{17}$)—C($R_5$)($R_{17}$).

Another group of compounds of Formula I includes compounds wherein W is CH and wherein V—Z—Y is independently any one of or combination of O—C($R_3$)=N, O—C($R_5$)($R_3$)—N($R_4$), O—C($R_5$)($R_3$)—S, O—N=C($R_5$), O—C($R_3$)($R_8$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)$_2$—O—C($R_5$)$_2$, C($R_5$)$_2$—S—C($R_5$)$_2$, C($R_5$)$_2$—N($R_4$)—C($R_5$)$_2$, or C($R_5$)$_2$—C($R_3$)($R_5$)—C($R_5$)$_2$.

Another group of compounds of Formula I includes compounds wherein W is CH and wherein V—Z—Y is independently any one of or combination of O—C($R_3$)=N, O—C($R_5$)($R_3$)—N($R_4$), O—C($R_5$)($R_3$)—S, O—N=C($R_5$), O—C($R_3$)($R_8$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)$_2$—O—C($R_5$)$_2$, C($R_5$)$_2$—S—C($R_5$)$_2$, C($R_5$)$_2$—N($R_4$)—C($R_5$)$_2$, or C($R_5$)($R_{17}$)—C($R_3$)($R_{17}$)—C($R_5$)($R_{17}$).

Another group of compounds of Formula I includes compounds wherein W is N. Another group of compounds of Formula I includes compounds wherein W is N and wherein V—Z—Y is independently any one of or combination of O—C($R_3$)=N, O—C($R_5$)($R_3$)—N($R_4$), O—C($R_5$)($R_3$)—S, O—N=C($R_5$) O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)=C($R_3$)—C($R_5$)$_2$, or C($R_5$)$_2$—C($R_3$)($R_5$)—C($R_5$)$_2$.

Another group of compounds of Formula I includes compounds wherein $R_3$ is H, F, alkyl, halogenated alkyl, substituted alkyl, lactam heterocycloalkyl, phenoxy, substituted phenoxy, $R_7$, $R_9$, —N($R_4$)-aryl, —O-substituted phenyl, —O-substituted naphthyl, —S-substituted phenyl, —S-substituted naphthyl, alkyl substituted on the ω carbon with naphthyl, or alkyl substituted on the ω carbon with substituted naphthyl. Said ω carbon is determined by counting the longest carbon chain of the alkyl moiety with the C-1 carbon being the carbon attached to the bicyclic moiety $W^0$ and the ω carbon being the carbon furthest, e.g., separated by the greatest number of carbon atoms in the chain, from said C-1 carbon. Another group of compounds of Formula I includes compounds wherein $R_3$ is H, F, alkyl, halogenated alkyl, substituted alkyl, lactam heterocycloalkyl, phenoxy, substituted phenoxy, —N($R_4$)-aryl, —O-substituted phenyl, —O-substituted naphthyl, —S-substituted phenyl, —S-substituted naphthyl, alkyl substituted on the ω carbon with naphthyl, or alkyl substituted on the ω carbon with substituted naphthyl.

Another group of compounds of Formula I includes compounds wherein $R_3$ is H, F, alkyl, halogenated alkyl, lactam heterocycloalkyl, phenoxy, substituted phenoxy, $R_7$, $R_9$, —N($R_4$)-aryl, —O-substituted phenyl, —O-substituted naphthyl, —S-substituted phenyl, —S-substituted naphthyl, or or alkyl substituted on the ω carbon with $R_{15}$.

Another group of compounds of Formula I includes compounds wherein $R_3$ is H, F, alkyl, halogenated alkyl, lactam heterocycloalkyl, phenoxy, substituted phenoxy, —N($R_4$)-aryl, —O-substituted phenyl, —O-substituted naphthyl, —S-substituted phenyl, —S —substituted naphthyl, or alkyl substituted on the ω carbon with $R_{15}$.

Another group of compounds of Formula I includes compounds wherein $R_5$ is H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —$NO_2$, —$OR_1$, —C(O)N($R_{16}$)$_2$, —$NHR_1$, —$NR_1COR_{16}$, —N($R_{10}$)$_2$, —$SR_1$, —C(O)$R_{16}$, —$CO_2R_1$, aryl, $R_7$, or $R_9$. Another group of compounds of Formula I includes compounds wherein $R_5$ is H, F, Br, Cl, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —$NO_2$, —$OR_1$, —C(O)N($R_{16}$)$_2$, —$NHR_1$, —$NR_1COR_{16}$, —N($R_{10}$)$_2$, —$SR_1$.

Another group of compounds of Formula I includes compounds wherein $R_6$ is any one of or combination of H, F, Cl, Br, I, —CN, —$CF_3$, —$OR_{16}$, —$SR_{16}$, or —N($R_{16}$)$_2$. Another group of compounds of Formula I includes compounds wherein $R_6$ is any one of or combination of H, F, Cl, Br, —CN, —$CF_3$, —$OR_{16}$, —$SR_{16}$, or —N($R_{16}$)$_2$.

Another group of compounds of Formula I includes compounds wherein $R_{17}$ is any one of or combination of H, F, Br, Cl, I, alkyl, substituted alkyl, halogenated alkyl, alkenyl, substituted alkenyl, halogenated alkenyl, alkynyl, substituted alkynyl, halogenated alkynyl, —CN, —$OR_1$, —C(O)$NH_2$, —$NHR_1$, —$SR_1$, —$CO_2R_1$, aryl, $R_7$, or $R_9$. Another group of compounds of Formula I includes compounds wherein $R_{17}$ is any one of or combination of H, F, Br, Cl, alkyl, substituted alkyl, halogenated alkyl, alkenyl, substituted alkenyl, halogenated alkenyl, alkynyl, substituted alkynyl, halogenated alkynyl, —CN, —$OR_1$, —C(O)$NH_2$, —$NHR_1$, —$SR_1$.

Another group of compounds of Formula I includes compounds wherein $R_{21}$ is any one of or combination of H, F, Cl, Br, I, alkyl, substituted alkyl, halogenated alkyl, cycloalkyl, —CN, —$NR_{22}R_{22}$, —$OR_{22}$, or —$SR_{22}$. Another group of compounds of Formula I includes compounds wherein $R_{21}$ is any one of or combination of H, F, Cl, Br, alkyl, substituted alkyl, halogenated alkyl, —CN, —N($R_{22}$)$_2$, —$OR_{22}$, or —$SR_{22}$.

Another group of compounds of Formula I includes compounds wherein $R_{23}$ is any one of or combination of H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, substituted phenyl, naphthyl, substituted naphthyl, $R_7$, or $R_9$. Another group of compounds of Formula I includes compounds wherein $R_{23}$ is any one of or combination of H, alkyl, halogenated alkyl, substituted alkyl, heterocycloalkyl, or substituted heterocycloalkyl.

Another group of compounds of Formula I includes compounds wherein $W^0$ is

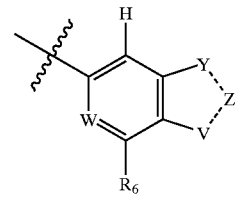

wherein W, $R_6$, and V—Z—Y are defined herein.

Another group of compounds of Formula I includes compounds wherein $W^0$ is

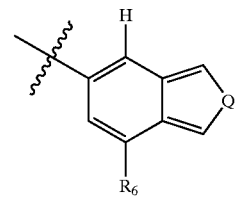

wherein Q and $R_6$ are defined herein.

Another group of compounds of Formula I for treating the diseases or conditions discussed herein includes compounds wherein $W^0$ is

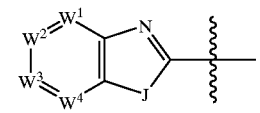

wherein $W^1$, $W^2$, $W^3$, $W^4$ are each independently N or C($R_{21}$), provided that no more than two of $W^1$, $W^2$, $W^3$, $W^4$ are N, and further provided when more than two of $W^1$, $W^2$, $W^3$, $W^4$ are C($R_{21}$) that no more than two $R_{21}$ are other than H; and wherein J is N($R_{23}$), S, or O.

Another group of compounds of Formula I includes compounds wherein $W^0$ is

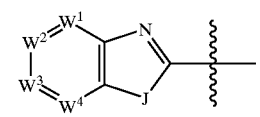

wherein $W^1$, $W^2$, $W^3$, $W^4$ are each independently N or C($R_{21}$), provided that no more than two of $W^1$, $W^2$, $W^3$, $W^4$ are N, further provided that when J is N($R_{23}$), at least one of $W^1$, $W^2$, $W^3$, $W^4$ is N, and further provided when more than two of $W^1$, $W^2$, $W^3$, $W^4$ are C($R_{21}$) that no more than two $R_{21}$ are other than H; and wherein J is N($R_{23}$), S, or O.

Another group of compounds of Formula I includes compounds wherein $W^0$ is

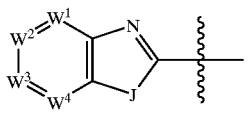

wherein $W^1$, $W^2$, $W^3$, $W^4$ are each independently N or $C(R_{21})$, provided that no more than two of $W^1$, $W^2$, $W^3$, $W^4$ are N, and further provided when more than two of $W^1$, $W^2$, $W^3$, $W^4$ are $C(R_{21})$ that no more than two $R_{21}$ are other than H; and wherein J is S, or O.

Another group of compounds of Formula I includes compounds wherein $W^0$ includes any one of or combination of the following:

1,3-benzoxazol-6-yl, 1,3-benzoxazol-5-yl, 1,3-benzothiazol-6-yl, indan-5-yl, 1,3-benzodioxol-5-yl, [1,3]oxazolo[5,4-c]pyridin-6-yl, 2-benzoisothiophen-5-yl, 1,3-benzothiazol-5-yl, 1,3-benzothiazol-2-yl, 1,2-benzisoxazol-6-yl, 1,2-benzisoxazol-5-yl, 3H-imidazo[4,5-b]pyridin-2-yl, or 1H-indazol-6-yl, optionally substituted with F, Br, Cl, alkyl, halogenated alkyl, substituted alky, alkyl substituted on the ω carbon with $R_{15}$, alkenyl, substituted alkenyl, halogenated alkenyl, alkynyl, substituted alkynyl, halogenated alkynyl, heterocycloalkyl, substituted heterocycloalkyl, lactam heterocycloalkyl, phenoxy, substituted phenoxy, —CF$_3$, —CN, —NO$_2$, —OR$_1$, —OR$_{16}$, —OR$_{22}$, —O-substituted phenyl, —O-substituted naphthyl, —NHR$_1$, —N(R$_{10}$)$_2$, —N(R$_{16}$)$_2$, —N(R$_{22}$)$_2$, —N(R$_4$)-aryl, —SR$_1$, —SR$_{16}$, —SR$_{22}$, —S-substituted phenyl, —S-substituted naphthyl, —C(O)N(R$_{16}$)$_2$, —NR$_1$COR$_{16}$. One of ordinary skill in the art will recognize where the optional substitution is allowed by comparing the listed moieties with $W^0$ and identifying where $R_3$, $R_4$, $R_5$, $R_6$, $R_{17}$, $R_{21}$, and $R_{23}$ would allow for substitution.

Another group of compounds of Formula I includes any one of or combination of the following:
N-((3R)-1-azabicyclo[2.2.2]oct-3-yl)-1,3-benzoxazole-6-carboxamide; N-((3R)1-azabicyclo[2.2.2]oct-3-yl)-2-methyl-1,3-benzoxazole-6-carboxamide; N-((3R)1-azabicyclo[2.2.2]oct-3-yl)-1,3-benzoxazole-5-carboxamide; N-((3R)1-azabicyclo[2.2.2]oct-3-yl)-2-methyl-1,3-benzoxazole-5-carboxamide; N-((3R)1-azabicyclo[2.2.2]oct-3-yl)-1,3-benzothiazole-6-carboxamide; N-((3R)1-azabicyclo[2.2.2]oct-3-yl)indane-5-carboxamide; N-((3R)-1-azabicyclo[2.2.2]oct-3-yl)-1,3-benzodioxole-5-carboxamide; N-[(3R)-1-azabicyclo[2.2.2]oct-3-yl][1,3]oxazolo[5,4-c]pyridine-6-carboxamide; N-[(3R)-1-azabicyclo[2.2.2]oct-3-yl]-2-benzoisothiophene-5-carboxamide; N-[(3R)-1-azabicyclo[2.2.2]oct-3-yl]-1,3-benzothiazole-5-carboxamide; N-[(3R)-1-azabicyclo[2.2.2]oct-3-yl]-3-methyl-1,2-benzisoxazole-6-carboxamide; N-[(3R)-1-azabicyclo[2.2.2]oct-3-yl]-3-methyl-1,2-benzisoxazole-5-carboxamide; N-[(3R)-1-azabicyclo[2.2.2]oct-3-yl]-1H-indazole-6-carboxamide; N-[(3R)-1-azabicyclo[2.2.2]oct-3-yl]-1,3-benzothiazole-2-carboxamide; N-[(3R)-1-azabicyclo[2.2.2]oct-3-yl]-6-fluoro-1,3-benzothiazole-2-carboxamide; N-[(3R)-1-azabicyclo[2.2.2]oct-3-yl]-3H-imidazo[4,5-b]pyridine-2-carboxamide; N-((2S,3R)-2-methyl-1-azabicyclo[2.2.2]oct-3-yl)-1,3-benzoxazole-6-carboxamide; N-((2S,3R)-2-methyl-1-azabicyclo[2.2.2]oct-3-yl)-2-methyl-1,3-benzoxazole-6-carboxamide; N-((2S,3R)-2-methyl-1-azabicyclo[2.2.2]oct-3-yl)-1,3-benzoxazole-5-carboxamide; N-((2S,3R)-2-methyl-1-azabicyclo[2.2.2]oct-3-yl)-2-methyl-1,3-benzoxazole-5-carboxamide; N-((2S,3R)-2-methyl-1-azabicyclo[2.2.2]oct-3-yl)-1,3-benzothiazole-6-carboxamide; N-((2S,3R)-2-methyl-1-azabicyclo[2.2.2]oct-3-yl)indane-5-carboxamide; N-((2S,3R)-2-methyl-1-azabicyclo[2.2.2]oct-3-yl)-1,3-benzothiazole-5-carboxamide; N-[(2S,3R)-2-methyl-1-azabicyclo[2.2.2]oct-3-yl]-1,3-benzodioxole-5-carboxamide; N-[(2S,3R)-2-methyl-1-azabicyclo[2.2.2]oct-3-yl][1,3]oxazolo[5,4-c]pyridine-6-carboxamide; N-[(2S,3R)-2-methyl-1-azabicyclo[2.2.2]oct-3-yl]-2-benzoisothiophene-5-carboxamide; N-[(2S,3R)-2-methyl-1-azabicyclo[2.2.2]oct-3-yl]-1,3-benzothiazole-5-carboxamide; N-[(2S,3R)-2-methyl-1-azabicyclo[2.2.2]oct-3-yl]-3-methyl-1,2-benzisoxazole-6-carboxamide; N-[(2S,3R)-2-methyl-1-azabicyclo[2.2.2]oct-3-yl]-3-methyl-1,2-benzisoxazole-5-carboxamide; N-[(2S,3R)-2-methyl-1-azabicyclo[2.2.2]oct-3-yl]-1H-indazole-6-carboxamide; N-[(2S,3R)-2-methyl-1-azabicyclo[2.2.2]oct-3-yl]-1,3-benzothiazole-2-carboxamide; N-[(2S,3R)-2-methyl-1-azabicyclo[2.2.2]oct-3-yl]-6-fluoro-1,3-benzothiazole-2-carboxamide; N-[(2S,3R)-2-methyl-1-azabicyclo[2.2.2]oct-3-yl]-3H-imidazo[4,5-b]pyridine-2-carboxamide; or a pharmaceutically acceptable salt or pharmaceutical composition thereof.

Another group of compounds of Formula I includes any one of or combination of the following: N-((3S)-1-azabicyclo[2.2.2]oct-3-yl)-1,3-benzoxazole-6-carboxamide; N-((3S)1-azabicyclo[2.2.2]oct-3-yl)-2-methyl-1,3-benzoxazole-6-carboxamide; N-((3S)1-azabicyclo[2.2.2]oct-3-yl)-1,3-benzoxazole-5-carboxamide; N-((3S)1-azabicyclo[2.2.2]oct-3-yl)-2-methyl-1,3-benzoxazole-5-carboxamide; N-((3S)1-azabicyclo[2.2.2]oct-3-yl)-1,3-benzothiazole-6-carboxamide; N-((3S)1azabicyclo[2.2.2]oct-3-yl)indane-5-carboxamide; N-((3S)-1-azabicyclo[2.2.2]oct-3-yl)-1,3-benzodioxole-5-carboxamide; N-[(3S)-1-azabicyclo[2.2.2]oct-3-yl][1,3]oxazolo[5,4-c]pyridine-6-carboxamide; N-[(3S)-1-azabicyclo[2.2.2]oct-3-yl]-2-benzoisothiophene-5-carboxamide N-[(3S)-1-azabicyclo[2.2.2]oct-3-yl]-1,3-benzothiazole-5-carboxamide; N-[(3S)-1-azabicyclo[2.2.2]oct-3-yl]-3-methyl-1,2-benzisoxazole-6-carboxamide; N-[(3S)-1-azabicyclo[2.2.2]oct-3-yl]-3-methyl-1,2-benzisoxazole-5-carboxamide; N-[(3S)-1-azabicyclo[2.2.2]oct-3-yl]-1H-indazole-6-carboxamide; N-[(3S)-1-azabicyclo[2.2.2]oct-3-yl]-1,3-benzothiazole-2-carboxamide; N-[(3S)-1-azabicyclo[2.2.2]oct-3-yl]-6-fluoro-1,3-benzothiazole-2-carboxamide; N-[(3S)-1-azabicyclo[2.2.2]oct-3-yl]-3H-imidazo[4,5-b]pyridine-2-carboxamide; or a pharmaceutically acceptable salt or pharmaceutical composition thereof.

Another group of compounds of Formula I includes any one of or combination of the following: N-[(3R)-1-azabicyclo[2.2.2]oct-3-yl]-1H-indazole-5-carboxamide; N-[(3R)-1-azabicyclo[2.2.2]oct-3-yl]-3-methyl-1H-indazole-6-carboxamide; N-[(3R)-1-azabicyclo[2.2.2]oct-3-yl]-3-methyl-1H-indazole-5-carboxamide; N-[(3R)-1-azabicyclo[2.2.2]oct-3-yl]-3-ethyl-1H-indazole-6-carboxamide; N-[(3R)-1-azabicyclo[2.2.2]oct-3-yl]-3-ethyl-1H-indazole-5-carboxamide; N-[(3R)-1-azabicyclo[2.2.2]oct-3-yl]-1,2-benzisothiazole-6-carboxamide; N-[(3R)-1-azabicyclo[2.2.2]oct-3-yl]-1,2-benzisothiazole-5-carboxamide; N-[(3R)-1-azabicyclo[2.2.2]oct-3-yl]-3-ethyl-1,2-benzisothiazole-6-carboxamide; N-[(3R)-1-azabicyclo[2.2.2]oct-3-yl]-3-ethyl-1,2-benzisothiazole-5-carboxamide; N-[(3R)-1-azabicyclo[2.2.2]oct-3-yl]-3-methyl-1,2-benzisothiazole-6-carboxamide; N-[(3R)-1-azabicyclo[2.2.2]oct-3-yl]-3-methyl-1,2-benzisothiazole-5-carboxamide; N-[(3R)-1-azabicyclo[2.2.2]oct-3-yl]-2-cyclopropyl-1,3-benzoxazole-6-carboxamide; N-[(3R)-1-azabicyclo[2.2.2]oct-3-yl]-2-cyclopropyl-1,3-benzoxazole-5-carboxamide; N-[(3R)-1-azabicyclo[2.2.2]oct-3-yl]-2- cyclopropyl-1,3-benzothiazole-6-carboxamide; N-[(3R)-1-azabicyclo[2.2.2]oct-3-yl]-2-cyclopropyl-1,3-benzothiazole-5-carboxamide; N-[(3R)-1-azabicyclo[2.2.2]oct-3-yl]-2-methyl-1,3-benzothiazole-6-carboxamide; N-[(3R)-1-azabicyclo[2.2.2]oct-3-yl]-2-methyl-1,3-benzothiazole-5-carboxamide; N-[(3R)-1-azabicyclo[2.2.2]oct-3-yl]-2-ethyl-1,3-benzothiazole-6-carboxamide; N-[(3R)-1-azabicyclo[2.2.2]oct-3-yl]-2-ethyl-1,3-benzothiazole-5-carboxamide; N-[(3R)-1-azabicyclo[2.2.2]oct-3-yl]-2-methyl-1,3-benzodioxole-5-carboxamide; N-[(3R)-1-azabicyclo[2.2.2]oct-3-yl]-2-ethyl-1,3-benzodioxole-5-carboxamide; N-[(3R)-1-azabicyclo[2.2.2]oct-3-yl]-2,2-dimethyl-1,3-benzodioxole-5-carboxamide; N-[(3R)-1-azabicyclo[2.2.2]oct-3-yl]-2-benzofuran-5-carboxamide; N-[(3R)-1-azabicyclo[2.2.2]oct-3-yl]-2H-isoindole-5-carboxamide; N-[(3R)-1-azabicyclo[2.2.2]oct-3-yl]-1H-benzimidazole-5-carboxamide; N-[(3R)-1-azabicyclo[2.2.2]oct-3-yl][1,3]thiazolo[5,4-c]pyridine-6-carboxamide; N-[(3R)-1-azabicyclo[2.2.2]oct-3-yl][1,3]thiazolo[4,5-c]pyridine-6-carboxamide; N-[(3R)-1-azabicyclo[2.2.2]oct-3-yl][1,3]dioxolo[4,5-c]pyridine-6-carboxamide; N-[(3R)-1-azabicyclo[2.2.2]oct-3-yl][1,3]oxazolo[4,5-c]pyridine-6-carboxamide; N-[(3R)-1-azabicyclo[2.2.2]oct-3-yl]-1H-imidazo[4,5-c]pyridine-6-carboxamide;

N-[(2S,3R)-2-methyl-1-azabicyclo[2.2.2]oct-3-yl]-1H-indazole-6-carboxamide; N-[(2S,3R)-2-methyl-1-azabicyclo[2.2.2]oct-3-yl]-1H-indazole-5-carboxamide; N-[(2S,3R)-2-methyl-1-azabicyclo[2.2.2]oct-3-yl]-3-methyl-1H-indazole-6-carboxamide; N-[(2S,3R)-2-methyl-1-azabicyclo[2.2.2]oct-3-yl]-3-methyl-1H-indazole-5-carboxamide; N-[(2S,3R)-2-methyl-1-azabicyclo[2.2.2]oct-3-yl]-3-ethyl-1H-indazole-6-carboxamide; N-[(2S,3R)-2-methyl-1-azabicyclo[2.2.2]oct-3-yl]-3-ethyl-1H-indazole-5-carboxamide; N-[(2S,3R)-2-methyl-1-azabicyclo[2.2.2]oct-3-yl]-1,2-benzisothiazole-6-carboxamide; N-[(2S,3R)-2-methyl-1-azabicyclo[2.2.2]oct-3-yl]-1,2-benzisothiazole-5-carboxamide; N-[(2S,3R)-2-methyl-1-azabicyclo[2.2.2]oct-3-yl]-3-ethyl-1,2-benzisothiazole-6-carboxamide; N-[(2S,3R)-2-methyl-1-azabicyclo[2.2.2]oct-3-yl]-3-ethyl-1,2-benzisothiazole-5-carboxamide; N-[(2S,3R)-2-methyl-1-azabicyclo[2.2.2]oct-3-yl]-3-methyl-1,2-benzisothiazole-6-carboxamide; N-[(2S,3R)-2-methyl-1-azabicyclo[2.2.2]oct-3-yl]-3-methyl-1,2-benzisothiazole-5-carboxamide; N-[(2S,3R)-2-methyl-1-azabicyclo[2.2.2]oct-3-yl]-2-cyclopropyl-1,3-benzoxazole-6-carboxamide; N-[(2S,3R)-2-methyl-1-azabicyclo[2.2.2]oct-3-yl]-2-cyclopropyl-1,3-benzoxazole-5-carboxamide; N-[(2S,3R)-2-methyl-1-azabicyclo[2.2.2]oct-3-yl]-2-cyclopropyl-1,3-benzothiazole-6-carboxamide; N-[(2S,3R)-2-methyl-1-azabicyclo[2.2.2]oct-3-yl]-2-cyclopropyl-1,3-benziothiazole-5-carboxamide; N-[(2S,3R)-2-methyl-1-azabicyclo[2.2.2]oct-3-yl]-2-methyl-1,3-benzothiazole-6-carboxamide; N-[(2S,3R)-2-methyl-1-azabicyclo[2.2.2]oct-3-yl]-2-methyl-1,3-benzothiazole-5-carboxamide; N-[(2S,3R)-2-methyl-1-azabicyclo[2.2.2]oct-3-yl]-2-ethyl-1,3-benzothiazole-6-carboxamide; N-[(2S,3R)-2-methyl-1-azabicyclo[2.2.2]oct-3-yl]-2-ethyl-1,3-benzothiazole-5-carboxamide; N-[(2S,3R)-2-methyl-1-azabicyclo[2.2.2]oct-3-yl]-2-methyl-1,3-benzodioxole-5-carboxamide; N-[(2S,3R)-2-methyl-1-azabicyclo[2.2.2]oct-3-yl]-2-ethyl-1,3-benzodioxole-5-carboxamide; N-[(2S,3R)-2-methyl-1-azabicyclo[2.2.2]oct-3-yl]-2,2-dimethyl-1,3-benzodioxole-5-carboxamide; N-[(2S,3R)-2-methyl-1-azabicyclo[2.2.2]oct-3-yl]-2-benzofuran-5-carboxamide; N-[(2S,3R)-2-methyl-1-azabicyclo[2.2.2]oct-3-yl]-2H-isoindole-5-carboxamide; N-[(2S,3R)-2-methyl-1-azabicyclo[2.2.2]oct-3-yl]-1H-benzimidazole-5-carboxamide; N-[(2S,3R)-2-methyl-1-azabicyclo[2.2.2]oct-3-yl][1,3]thiazolo[5,4-c]pyridine-6-carboxamide; N-[(2S,3R)-2-methyl-1-azabicyclo[2.2.2]oct-3-yl][1,3]thiazolo[4,5-c]pyridine-6-carboxamide; N-[(2S,3R)-2-methyl-1-azabicyclo[2.2.2]oct-3-yl][1,3]dioxolo[4,5-c]pyridine-6-carboxamide; N-[(2S,3R)-2-methyl-1-azabicyclo[2.2.2]oct-3-yl][1,3]oxazolo[4,5-c]pyridine-6-carboxamide; N-[(2S,3R)-2-methyl-1-azabicyclo[2.2.2]oct-3-yl]-1H-imidazo[4,5-c]pyridine-6-carboxamide; or a pharmaceutically acceptable salt or pharmaceutical composition thereof.

Abbreviations which are well known to one of ordinary skill in the art may be used (e.g., "Ph" for phenyl, "Me" for methyl, "Et" for ethyl, "h" or "hr" for hour or hours, min for minute or minutes, and "rt" or "RT" for room temperature).

All temperatures are in degrees Centigrade.

Room temperature is within the range of 15–25 degrees Celsius.

AChR refers to acetylcholine receptor.

nAChR refers to nicotinic acetylcholine receptor.

Pre-senile dementia is also known as mild cognitive impairment.

$5HT_3R$ refers to the serotonin-type 3 receptor.

α-btx refers to α-bungarotoxin.

FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).

TLC refers to thin-layer chromatography.

HPLC refers to high pressure liquid chromatography.

MeOH refers to methanol.

EtOH refers to ethanol.

IPA refers to isopropyl alcohol.

THF refers to tetrahydrofuran.

DMSO refers to dimethylsulfoxide.

DMF refers to N,N-dimethylformamide.

EtOAc refers to ethyl acetate.

TMS refers to tetramethylsilane.

TEA refers to triethylamine.

DIEA refers to N,N-diisopropylethylamine.

MLA refers to methyllycaconitine.

Ether refers to diethyl ether.

HATU refers to O-(7-azabenzotriazol-1-yl)-N,N,N',N'-tetramethyluronium hexafluorophosphate.

CDI refers to carbonyl diimidazole.

NMO refers to N-methylmorpholine-N-oxide.

TPAP refers to tetrapropylammonium perruthenate.

Halogen is F, Cl, Br, or I.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

Non-inclusive examples of heteroaryl compounds that fall within the definition of $R_7$ and $R_9$ include, but are not limited to, thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl.

Non-inclusive examples of heterocycloalkyl include, but are not limited to, tetrahydrofurano, tetrahydropyrano, morpholino, pyrrolidino, piperidino, piperazine, azetidino, azetidinono, oxindolo, dihydroimidazolo, and pyrrolidinono.

The ω carbon with $R_{15}$ is determined by counting the longest carbon chain of the alkyl moiety with the C-1 carbon being the carbon attached to the bicyclic moiety $W^0$ and the ω carbon being the carbon furthest, e.g., separated by the greatest number of carbon atoms in the chain, from said C-1 carbon.

The core molecule is the quinuclidinyl-(carboxamide-type moiety)-$W^0$:

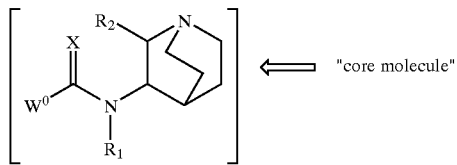  ⇐ "core molecule"

Therefore, when determining the ω carbon, the C-1 carbon will be the carbon attached, as valency allows, to the $W^0$ moiety of the core molecule and the ω carbon will be the carbon furthest from said C-1 carbon.

Mammal denotes human and other mammals.

Brine refers to an aqueous saturated sodium chloride solution.

Equ means molar equivalents.

IR refers to infrared spectroscopy.

Lv refers to leaving groups within a molecule, including Cl, OH, or mixed anhydride.

NMR refers to nuclear (proton) magnetic resonance spectroscopy, chemical shifts are reported in ppm (δ) downfield from TMS.

MS refers to mass spectrometry expressed as m/e or mass/charge unit. HRMS refers to high resolution mass spectrometry expressed as m/e or mass/charge unit. M+H$^+$ refers to the positive ion of a parent plus a hydrogen atom. M–H$^-$ refers to the negative ion of a parent minus a hydrogen atom. M+Na$^+$ refers to the positive ion of a parent plus a sodium atom. M+K$^+$ refers to the positive ion of a parent plus a potassium atom. EI refers to electron impact. ESI refers to electrospray ionization. CT refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The compounds of Formula I have optically active center (s) on the quinuclidine ring. Although it is desirable that the stereochemical purity be as high as possible, absolute purity is not required. This invention involves racemic mixtures and compositions of varying degrees of stereochemical purities. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001 to 100 mg/kg/day for an adult, preferably in the range of about 0.1 to 50 mg/kg/day for an adult. A total daily dose of about 1 to 1000 mg of active ingredient may be appropriate for an adult. The daily dose can be administered in one to four doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, EtOH, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the $\gamma$-aminobutyric acid type A receptor. Like the other members of this receptor superfamily, the $5HT_3R$ exhibits a large degree of sequence homology with $\alpha$ 7 nAChR but functionally the two ligand-gated ion channels are very different. For example, $\alpha 7$ nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the $\alpha 7$ nAChR and $5HT_3R$ proteins have some degree of homology, but function very differently. Indeed the pharmacology of the channels is very different. For example, Ondansetron, a highly selective $5HT_3R$ antagonist, has little activity at the $\alpha 7$ nAChR. The converse is also true. For example, GTS-21, a highly selective $\alpha 7$ nAChR agonist, has little activity at the $5HT_3R$.

$\alpha 7$ nAChR is a ligand-gated $Ca^{++}$ channel formed by a homopentamer of $\alpha 7$ subunits. Previous studies have established that $\alpha$-bungarotoxin ($\alpha$-btx) binds selectively to this homopetameric, $\alpha 7$ nAChR subtype, and that $\alpha 7$ nAChR has a high affinity binding site for both ($\alpha$-btx and methyllycaconitine (MLA). $\alpha 7$ nAChR is expressed at high levels in the hippocampus, ventral tegmental area and ascending cholinergic projections from nucleus basilis to thalamocortical areas. $\alpha 7$ nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology*, 108:417–31, 1992; Levin, E. D. and Simon B. B., *Psychopharmacology*, 138:217–30, 1998). For example, it is well known that nicotine increases cognition and attention in humans. ABT-418, a compound that activates $\alpha 4\beta 2$ and $\alpha 7$ nAChR, improves cognition and attention in clinical trials of Alzheimer's disease and attention-deficit disorders (Potter, A. et. al., *Psychopharmacology (Berl).*, 142(4):334–42, March 1999; Wilens, T. E. et. al., *Am. J. Psychiatry*, 156(12):1931–7, December 1999). It is also clear that nicotine and selective but weak $\alpha 7$ nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "a typical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., *Am J Psychiatry*, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencepholographic (EEG) recordings of neuronal activity of the hippocampus are used to measure the subject's response to a series of auditory "clicks" (Adler, L. E. et. al., *Biol. Psychiatry*, 46:8–18, 1999). Normal individuals respond to the first click with greater degree than to the second click. In general, schizophrenics and schizotypal patients respond to both clicks nearly the same (Cullum, C. M. et. al., *Schizophr. Res.*, 10:131–41, 1993). These data reflect a schizophrenic's inability to "filter" or ignore unimportant information. The sensory gating deficit appears to be one of the key pathological features of this disease (Cadenhead, K. S. et. al., *Am. J. Psychiatry*, 157:55–9, 2000). Multiple studies show that nicotine normalizes the sensory deficit of schizophrenia (Adler, L. E. et. al., *Am. J. Psychiatry*, 150:1856–61, 1993). Pharmacological studies indicate that nicotine's effect on sensory gating is via the $\alpha 7$ nAChR (Adler, L. E. et. al., *Schizophr. Bull.*, 24:189–202, 1998). Indeed, the biochemical data indicate that schizophrenics have 50% fewer of $\alpha 7$ nAChR receptors in the hippocampus, thus giving a rationale to partial loss of α7 nAChR functionality (Freedman, R. et. al., *Biol. Psychiatry*, 38:22–33, 1995). Interestingly, genetic data indicate that a polymorphism in the promoter region of the α7 nAChR gene is strongly associated with the sensory gating deficit in schizophrenia (Freedman, R. et. al., *Proc. Nat'l Acad. Sci. USA*, 94(2):587–92, 1997; Myles-Worsley, M. et. al.,*Am. J. Med. Genet*, 88(5):544–50, 1999). To date, no mutation in the coding region of the α7 nAChR has been identified. Thus, schizophrenics express the same α7 nAChR as non-schizophrenics.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and 5HT$_3$R. To conduct such an assay, one uses cell lines that expressed functional forms of the α7 nAChR using the α7/5-HT$_3$ channel as the drug target and cell lines that expressed functional 5HT$_3$R. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating schizophrenia, or psychosis.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Psychosis is a mental disorder characterized by gross impairment in the patient's perception of reality. The patient may suffer from delusions, and hallucinations, and may be incoherent in speech. His behavior may be agitated and is often incomprehensible to those around him. In the past, the term psychosis has been applied to many conditions that do not meet the stricter definition given above. For example, mood disorders were named as psychoses.

There are a variety of antipsychotic drugs. The conventional antipsychotic drugs include Chlorpromazine, Fluphenazine, Haloperidol, Loxapine, Mesoridazine, Molindone, Perphenazine, Pimozide, Thioridazine, Thiothixene, and Trifluoperazine. These drugs all have an affinity for the dopamine 2 receptor.

These conventional antipsychotic drugs have several side effects, including sedation, weight gain, tremors, elevated prolactin levels, akathisia (motor restlessness), dystonia and muscle stiffness. These drugs may also cause tardive dyskinesia. Unfortunately, only about 70% of patients with schizophrenia respond to conventional antipsychotic drugs. For these patients, a typical antipsychotic drugs are available.

Atypical antipsychotic drugs generally are able to alleviate positive symptoms of psychosis while also improving negative symptoms of the psychosis to a greater degree than conventional antipsychotics. These drugs may improve neurocognitive deficits. Extrapyramidal (motor) side effects are not as likely to occur with the a typical antipsychotic drugs, and thus, these a typical antipsychotic drugs have a lower risk of producing tardive dyskinesia. Finally these a typical antipsychotic drugs cause little or no elevation of prolactin. Unfortunately, these drugs are not free of side effects. Although these drugs each produce different side effects, as a group the side effects include: agranulocytosis; increased risk of seizures, weight gain, somnolence, dizziness, tachycardia, decreased ejaculatory volume, and mild prolongation of QTc interval.

In a combination therapy to treat multiple symptoms of diseases such as schizophrenia, the compounds of Formula I and the anti-psychotic drugs can be administered simultaneously or at separate intervals. When administered simultaneously the compounds of Formula I and the antipsychotic drugs can be incorporated into a single pharmaceutical composition, e.g., a pharmaceutical combination therapy composition. Alternatively, two separate compositions, i.e., one containing compounds of Formula I and the other containing anti-psychotic drugs, can be administered simultaneously. Examples of anti-psychotic drugs, in addition to those listed above, include, but are not limited to, Thorazine, Mellaril, Trilafon, Navane, Stelazine, Permitil, Prolixin, Risperdal, Zyprexa, Seroquel, ZELDOX, Acetophenazine, Carphenazine, Chlorprothixene, Droperidol, Loxapine, Mesoridazine, Molindone, Ondansetron, Pimozide, Prochlorperazine, and Promazine.

A pharmaceutical combination therapy composition can include therapeutically effective amounts of the compounds of Formula I, noted above, and a therapeutically effective amount of anti-psychotic drugs. These compositions may be formulated with common excipients, diluents or carriers, and compressed into tablets, or formulated elixirs or solutions for convenient oral administration or administered by intramuscular intravenous routes. The compounds can be administered rectally, topically, orally, sublingually, or parenterally and maybe formulated as sustained relief dosage forms and the like.

When separately administered, therapeutically effective amounts of compositions containing compounds of Formula I and anti-psychotic drugs are administered on a different schedule. One may be administered before the other as long as the time between the two administrations falls within a therapeutically effective interval. A therapeutically effective interval is a period of time beginning when one of either (a) the compounds of Formula I, or (b) the anti-psychotic drugs is administered to a human and ending at the limit of the beneficial effect in the treatment of schizophrenia or psychosis of the combination of (a) and (b). The methods of administration of the compounds of Formula I and the anti-psychotic drugs may vary. Thus, either agent or both agents may be administered rectally, topically, orally, sublingually, or parenterally.

As discussed, the compounds of the present invention are α7 nAChR agonists. Therefore, as another aspect of the present invention, the compounds of the present invention may be used to treat a variety of diseases including cognitive and attention deficit symptoms of Alzheimer's, neurodegeneration associated with diseases such as Alzheimer's disease, pre-senile dementia (also known as mild cognitive impairment), and senile dementia.

Alzheimer's disease has many aspects, including cognitive and attention deficits. Currently, these deficits are treated with cholinesterase inhibitors. These inhibitors slow the break down of acetylcholine, and thereby provide a general nonspecific increase in the activity of the cholinergic nervous system. Since the drugs are nonspecific, they have a wide variety of side effects. Thus, there is a need for a drug that stimulates a portion of the cholinergic pathways and thereby provides improvement in the cognitive and attention deficits associated with Alzheimer's disease without the side effects created by nonspecific stimulation of the cholinergic pathways.

Neurodegeneration is a common problem associated with diseases such as Alzheimer's disease. While the current drugs treat some of the symptoms of this disease, they do not control the underlying pathology of the disease. Accordingly, it would be desirable to provide a drug that can slow the progress of Alzheimer's disease.

Pre-senile dementia (mild cognitive impairment) concerns memory impairment rather than attention deficit problems and otherwise unimpaired cognitive functioning. Mild cognitive impairment is distinguished from senile dementia in that mild cognitive impairment involves a more persistent and troublesome problem of memory loss for the age of the patient. There currently is no medication specifically identified for treatment of mild cognitive impairment, due somewhat to the newness of identifying the disease. Therefore, there is a need for a drug to treat the memory problems associated with mild cognitive impairment.

Senile dementia is not a single disease state. However, the conditions classified under this name frequently include cognitive and attention deficits. Generally, these deficits are not treated. Accordingly, there is a need for a drug that provides improvement in the cognitive and attention deficits associated with senile dementia.

As discussed, the compounds of the present invention are α7 nAChR agonists. Therefore, yet other diseases to be treated with compounds of the present invention include treating the cognitive and attention deficits as well as the neurodegeneration associated with attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, or symptoms associated with pain.

Attention deficit disorder is generally treated with methylphenidate, an amphetamine-like molecule that has some potential for abuse. Accordingly, it would be desirable to provide a drug that treats attention deficit disorder while having fewer side effects than the currently used drug.

Attention deficit hyperactivity disorder, otherwise known as ADHD, is a neurobehavioral disorder affecting 3–5% of all American children. ADHD concerns cognitive alone or both cognitive and behavioral actions by interfering with a person's ability to stay on a task and to exercise age-appropriate inhibition. Several types of ADHD exist: a predominantly inattentive subtype, a predominantly hyperactive-impulsive subtype, and a combined subtype. Treatment may include medications such as methylphenidate, dextroamphetamine, or pemoline, which act to decrease impulsivity and hyperactivity and to increase attention. No "cure" for ADHD currently exists. Children with the disorder seldom outgrow it; therefore, there is a need for appropriate medicaments.

Mood and affective disorders fall within a large group of diseases, including monopolar depression and bi-polar mood disorder. These diseases are treated with three major classes of compounds. The first group is the heterocyclic antidepressant (HCA's). This group includes the well-known tricyclic antidepressants. The second group of compounds used to treat mood disorders is the monoamine oxidase inhibitors (MAOI's) that are used in particular types of diseases. The third drug is lithium. Common side effects from HCA's are sedation and weight gain. In elderly patients with organic brain disease, the side effects of HCA's can also include seizures and behavioral symptoms. The main side effects from using MAOI's occur from dietary and drug interactions. Benign side effects from the use of lithium include, but are not limited to, weight gain, nausea, diarrhea, polyuria, polydipsia, and tremor. Toxic side effects from lithium can include persistent headache, mental confusion, and may reach seizures and cardiac arrhythmias. Therefore, agents with less side effects or interactions with food or other medications would be useful.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Borderline personality disorder, although not as well known as bipolar disorder, is more common. People having borderline personality disorder suffer from a disorder of emotion regulation. Pharmaceutical agents are used to treat specific symptoms, such as depression or thinking distortions.

Acquired immune deficiency syndrome (AIDS) results from an infection with the human immunodeficiency virus (HIV). This virus attacks selected cells and impairs the proper function of the immune, nervous, and other systems. HIV infection can cause other problems such as, but not limited to, difficulties in thinking, otherwise known as AIDS dementia complex. Therefore, there is a need to drugs to relieve the confusion and mental decline of persons with AIDS.

Amyotrophic lateral sclerosis, also known as Lou Gehrig's disease, belongs to a class of disorders known as motor neuron diseases wherein specific nerve cells in the brain and spinal cord gradually degenerate to negatively affect the control of voluntary movement. Currently, there is no cure for amyotrophic lateral sclerosis although patients may receive treatment from some of their symptoms and although Riluzole has been shown to prolong the survival of patients. Therefore, there is a need for a pharmaceutical agent to treat this disease.

Traumatic brain injury occurs when the brain is damaged from a sudden physical assault on the head. Symptoms of the traumatic brain injury include confusion and other cognitive problems. Therefore, there is a need to address the symptoms of confusion and other cognitive problems.

Brain tumors are abnormal growths of tissue found inside of the skull. Symptoms of brain tumors include behavioral and cognitive problems. Surgery, radiation, and chemotherapy are used to treat the tumor, but other agents are necessary to address associated symptoms. Therefore, there is a need to address the symptoms of behavioral and cognitive problems.

Persons with Down's syndrome have in all or at least some of their cells an extra, critical portion of the number 21 chromosome. Adults who have Down's syndrome are known to be at risk for Alzheimer-type dementia. Currently, there is no proven treatment for Down's syndrome. Therefore, there is a need to address the dementia associated with Down's syndrome.

Genetically programmed degeneration of neurons in certain areas of the brain cause Huntington's disease. Early symptoms of Huntington's disease include mood swings, or trouble learning new things or remembering a fact. Most drugs used to treat the symptoms of Huntington's disease have side effects such as fatigue, restlessness, or hyperexcitability. Currently, there is no treatment to stop or reverse the progression of Huntington's disease. Therefore, there is a need of a pharmaceutical agent to address the symptoms with fewer side effects.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Dementia with Lewy Bodies is a neurodegenerative disorder involving abnormal structures known as Lewy bodies found in certain areas of the brain. Symptoms of dementia with Lewy bodies include, but are not limited to, fluctuating cognitive impairment with episodic delirium. Currently, treatment concerns addressing the parkinsonian and psychiatric symptoms. However, medicine to control tremors or loss of muscle movement may actually accentuate the underlying disease of dementia with Lewy bodies. Therefore, there is a need of a pharmaceutical agent to treat dementia with Lewy bodies.

Age-related macular degeneration (AMD) is a common eye disease of the macula which is a tiny area in the retina that helps produce sharp, central vision required for "straight ahead" activities that include reading and driving. Persons with AMD lose their clear, central vision. AMD takes two forms: wet and dry. In dry AMD, there is a slow breakdown of light-sensing cells in the macula. There currently is no cure for dry AMD. In wet AMD, new, fragile blood vessels growing beneath the macula as dry AMD worsens and these vessels often leak blood and fluid to cause rapid damage to the macula quickly leading to the loss of central vision. Laser surgery can treat some cases of wet AMD. Therefore, there is a need of a pharmaceutical agent to address AMD.

Parkinson's disease is a neurological disorder characterized by tremor, hypokinesia, and muscular rigidity. Currently, there is no treatment to stop the progression of the disease. Therefore, there is a need of a pharmaceutical agent to address Parkinson's.

Tardive dyskinesia is associated with the use of conventional antipsychotic drugs. This disease is characterized by involuntary movements most often manifested by puckering of the lips and tongue and/or writhing of the arms or legs. The incidence of tardive dyskinesia is about 5% per year of drug exposure among patients taking conventional antipsychotic drugs. In about 2% of persons with the disease, tardive dyskinesia is severely disfiguring. Currently, there is no generalized treatment for tardive dyskinesia. Furthermore, the removal of the effect-causing drugs is not always an option due to underlying problems. Therefore, there is a need for a pharmaceutical agent to address the symptoms of tardive dyskinesia.

Pick's disease results from a slowly progressive deterioration of social skills and changes in personality with the resulting symptoms being impairment of intellect, memory, and language. Common symptoms include memory loss, lack of spontaneity, difficulty in thinking or concentrating, and speech disturbances. Currently, there is no specific treatment or cure for Pick's disease but some symptoms can be treated with cholinergic and serotonin-boosting antidepressants. In addition, antipsychotic medications may alleviate symptoms in FTD patients who are experiencing delusions or hallucinations. Therefore, there is a need for a pharmaceutical agent to treat the progressive deterioration of social skills and changes in personality and to address the symptoms with fewer side effects.

Post-traumatic stress disorder (PTSD) is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat Post traumatic stress disorder.

Dysregulation of food intake associated with eating disease, including bulemia nervosa and anorexia nervosa, involve neurophysiological pathways. Anorexia nervosa is hard to treat due to patients not entering or remaining in after entering programs. Currently, there is no effective treatment for persons suffering from severe anorexia nervosa. Cognitive behavioral therapy has helped patients suffering from bulemia nervosa; however, the response rate is only about 50% and current treatment does not adequately address emotional regulation. Therefore, there is a need for pharmaceutical agents to address neurophysiological problems underlying diseases of dysregulation of food intake.

Cigarette smoking has been recognized as a major public health problem for a long time. However, in spite of the public awareness of health hazard, the smoking habit remains extraordinarily persistent and difficult to break. There are many treatment methods available, and yet people continue to smoke. Administration of nicotine transdermally, or in a chewing gum base is common treatments. However, nicotine has a large number of actions in the body, and thus can have many side effects. It is clear that there is both a need and a demand of long standing for a convenient and relatively easy method for aiding smokers in reducing or eliminating cigarette consumption. A drug that could selectively stimulate only certain of the nicotinic receptors would be useful in smoke cessation programs.

Smoke cessation programs may involve oral dosing of the drug of choice. The drug may be in the form of tablets. However, it is preferred to administer the daily dose over the waking hours, by administration of a series of incremental doses during the day. The preferred method of such administration is a slowly dissolving lozenge, troche, or chewing gum, in which the drug is dispersed. Another drug in treating nicotine addiction is Zyban. This is not a nicotine replacement, as are the gum and patch. Rather, this works on other areas of the brain, and its effectiveness is to help control nicotine craving or thoughts about cigarette use in people trying to quit. Zyban is not very effective and effective drugs are needed to assist smokers in their desire to stop smoking. These drugs may be administered transdermally through the use of skin patches. In certain cases, the drugs may be administered by subcutaneous injection, especially if sustained release formulations are used.

Drug use and dependence is a complex phenomenon, which cannot be encapsulated within a single definition. Different drugs have different effects, and therefore different types of dependence. Drug dependence has two basic causes, that is, tolerance and physical dependence. Tolerance exists when the user must take progressively larger doses to produce the effect originally achieved with smaller doses. Physical dependence exists when the user has developed a state of physiologic adaptation to a drug, and there is a withdrawal (abstinence) syndrome when the drug is no longer taken. A withdrawal syndrome can occur either when the drug is discontinued or when an antagonist displaces the drug from its binding site on cell receptors, thereby counteracting its effect. Drug dependence does not always require physical dependence.

In addition drug dependence often involves psychological dependence, that is, a feeling of pleasure or satisfaction when taking the drug. These feelings lead the user to repeat the drug experience or to avoid the displeasure of being deprived of the drug. Drugs that produce strong physical dependence, such as nicotine, heroin and alcohol are often abused, and the pattern of dependence is difficult to break. Drugs that produce dependence act on the CNS and generally reduce anxiety and tension; produce elation, euphoria, or other pleasurable mood changes; provide the user feelings of increased mental and physical ability; or alter sensory perception in some pleasurable manner. Among the drugs that are commonly abused are ethyl alcohol, opioids, anxiolytics, hypnotics, cannabis (marijuana), cocaine, amphetamines, and hallucinogens. The current treatment for drug-addicted people often involves a combination of behavioral therapies and medications. Medications, such as methadone or LAAM (levo-alpha-acetyl-methadol), are effective in suppressing the withdrawal symptoms and drug craving associated with narcotic addiction, thus reducing illicit drug use and improving the chances of the individual remaining in treatment. The primary medically assisted withdrawal method for narcotic addiction is to switch the patient to a comparable drug that produces milder withdrawal symptoms, and then gradually taper off the substitute medication. The medication used most often is methadone, taken orally once a day. Patients are started on the lowest dose that prevents the more severe signs of withdrawal and then the dose is gradually reduced. Substitutes can be used also for withdrawal from sedatives. Patients can be switched to long-acting sedatives, such as diazepam or phenobarbital, which are then gradually reduced.

Gilles de la Tourette's Syndrome is an inherited neurological disorder. The disorder is characterized by uncontrollable vocal sounds called tics and involuntary movements. The symptoms generally manifest in an individual before the person is 18 years of age. The movement disorder may begin with simple tics that progress to multiple complex tics, including respiratory and vocal ones. Vocal tics may begin as grunting or barking noises and evolve into compulsive utterances. Coprolalia (involuntary scatologic utterances) occurs in 50% of patients. Severe tics and coprolalia may be physically and socially disabling. Tics tend to be more complex than myoclonus, but less flowing than choreic movements, from which they must be differentiated. The patient may voluntarily suppress them for seconds or minutes.

Currently simple tics are often treated with benzodiazepines. For simple and complex tics, Clonidine may be used. Long-term use of Clonidine does not cause tardive dyskinesia; its limiting adverse effect is hypotension. In more severe cases, antipsychotics, such as Haloperidol may be required, but side effects of dysphoria, parkinsonism, akathisia, and tardive dyskinesia may limit use of such antipsychotics. There is a need for safe and effective methods for treating this syndrome.

Glaucoma is within a group of diseases occurs from an increase in intraocular pressure causing pathological changes in the optical disk and negatively affects the field of vision. Medicaments to treat glaucoma either decrease the amount of fluid entering the eye or increase drainage of fluids from the eye in order to decrease intraocular pressure. However, current drugs have drawbacks such as not working over time or causing side effects so the eye-care professional has to either prescribe other drugs or modify the prescription of the drug being used. There is a need for safe and effective methods for treating problems manifesting into glaucoma.

Ischemic periods in glaucoma cause release of excitotoxic amino acids and stimulate inducible form of nitric oxide synthase (iNOS) leading to neurodegeneration. Alpha 7 nicotinic agonists may stimulate the release of inhibitory amino acids such as GABA which will dampen hyperexcitablity. Alpha 7 nicotinic agonists are also directly neuroprotective on neuronal cell bodies. Thus alpha 7 nicotinic agonists have the potential to be neuroprotective in glaucoma.

Persons afflicted with pain often have what is referred to as the "terrible triad" of suffering from the pain, resulting in sleeplessness and sadness, all of which are hard on the afflicted individual and that individual's family. Pain can manifest itself in various forms, including, but not limited to, headaches of all severity, back pain, neurogenic, and pain from other ailments such as arthritis and cancer from its existence or from therapy to irradicate it. Pain can be either chronic (persistent pain for months or years) or acute (short-lived, immediate pain to inform the person of possible injury and need of treatment). Persons suffering from pain respond differently to individual therapies with varying degrees of success. There is a need for safe and effective methods for treating pain.

Finally, the compounds of the present invention may be used in combination therapy with typical and a typical anti-psychotic drugs. All compounds within the present invention are useful for and may also be used in combination with each other to prepare pharmaceutical compositions. Such combination therapy lowers the effective dose of the anti-psychotic drug and thereby reduces the side effects of the anti-psychotic drugs. Some typical anti-psychotic drugs that may be used in the practice of the invention include Haldol. Some a typical anti-psychotic drugs include Ziprasidone, Olanzapine, Resperidone, and Quetiapine.

Compounds of Formula I can be prepared as shown in Scheme 1. The key step in the preparation of this class of compounds is the coupling of commercially-available 3-aminoquinuclidine with the requisite acid chloride (Lv=Cl), mixed anhydride (e.g., Lv=diphenyl phosphoryl, Bis(2-oxo-3-oxazolidinyl)phosphinyl, or acyloxy of the general formula of O—C(O)—$R_{Lv}$, where $R_{Lv}$ includes phenyl or t-butyl), or carboxylic acid (Lv=OH) in the presence of an activating agent. Suitable activating reagents are well known in the art, for examples see Kiso, Y., Yajima, H. "Peptides" pp. 39–91, San Diego, Calif., Academic Press, (1995), and include, but are not limited to, agents such as carbodiimides, phosphonium and uronium salts (such as HATU).

Scheme 1

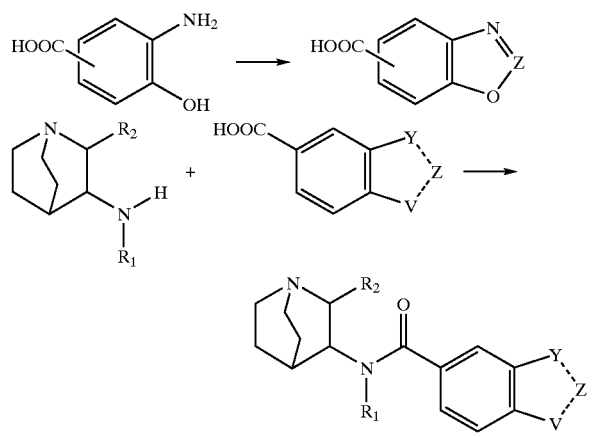

Preferably, the acid is coupled with the aminoquinuclidine using HATU in the presence of DIEA using $CH_2Cl_2$ as the solvent.

It will be apparent to those skilled in the art that the requisite carboxylic acids can be obtained through synthesis via literature procedures or through the slight modification thereof.

One of ordinary skill in the art will recognize that the methods described for the reaction of the unsubstituted 3-aminoquinuclidine ($R_2$=H) are equally applicable to substituted compounds ($R_2 \neq H$). Such compounds can be prepared by reduction of the oxime of the corresponding 3-quinuclidinone (see J. Labelled Compds. Radiopharm., 53–60 (1995) and J. Med. Chem. 988–995, (1998)). The oximes can be prepared by treatment of the 3-quinuclidinones with hydroxylamine hydrochloride in the presence of a base. The 3-quinuclidinones, where $R_2$=substituted alkyl, or cycloalkyl can be prepared by known procedures (see Tet. Lett. 1015–1018, (1972), J. Am. Chem. Soc. 1278–1291 (1994), J. Am. Chem. Soc. 4548–4552 (1989), Tetrahedron, 1139–1146 (2000)). The 3-quinuclidinones, where $R_2$=aryl, can be prepared by palladium catalyzed arylation as described in J. Am. Chem. Soc. 1473–1478 (1999) and J. Am. Chem. Soc. 1360–1370 (2000).

There are a variety of methods for constructing thioamides. One can treat the corresponding amide with a reagent such as Lawesson's reagent (2,4-bis(4-methoxyphenyl)-1,3-dithia-2,4-diphosphetane-2,4-disulfide). See Lawesson et. al. in Bull. Soc. Chim. Belg., 229 (1978)), or $P_4S_{10}$ (see Chem. Rev., 45 (1961). Alternatively one can react a dithiocarboxylic ester with the corresponding quinuclidine to form the same thioamide.

The following examples are provided as examples and are not intended to limit the scope of this invention to only those provided examples and named compounds. Also, the salts made in the examples are only exemplary and are not intended to limit the invention. Any pharmaceutically acceptable salt can be made by one of ordinary skill in the art. Further, the naming of specific stereoisomers is for exemplification, and is not intended to limit in anyway the scope of the invention. The examples were made using 3R-aminoquinuclidine. However, compounds could be made using the 3S-aminoquinuclinde making non-critical changes to the methods discussed herein. The invention includes the following examples in pure stereoisomeric form or as racemic mixtures.

EXAMPLE 1

N-((3R)-1-azabicyclo[2.2.2]oct-3-yl)-1,3-benzoxazole-6-carboxamide.fumarate

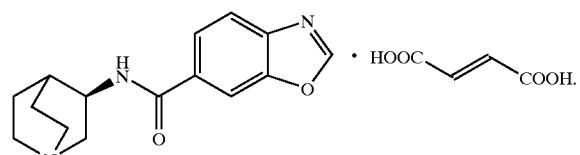

Method A. Preparation of 1,3-benzoxazole-6-carboxylic Acid (Acid C1).

A mixture of 4-amino-3-hydroxybenzoic acid (250 mg. 1.63 mmol) and trimethyl orthoformate (500 µL, 4.57 mmol) is heated in an oil bath at 100° C. for 2 h. The mixture is cooled to rt and diluted with MeOH. The resulting solution is filtered through a pad of Celite, and the filtrate is concentrated in vacuo to give Acid C1 as a brown solid (237 mg, 89%): $^1$H NMR (DMSO-$d_6$) δ 13.2, 8.9, 8.3, 8.0, 7.9.

Method B. Preparation of N-(1-azabicyclo[2.2.2]oct-3-yl)-1,3-benzoxazole-6-carboxamide .fumarate.

To a stirred solution of Acid C1 (194 mg, 1.19 mmol) in anhydrous THF/DMF (5:1, 12 mL) are added DIEA (600 µL, 3.44 mmol) and 3-(R)-aminoquinuclidine dihydrochloride (225 mg, 1.13 mmol). The mixture is cooled to –10° C. and HATU (430 mg, 1.13 mmol) is added in one portion. The reaction mixture is allowed to warm to rt and stirred overnight. The solvents are removed in vacuo and the residue is partitioned between saturated aqueous potassium carbonate solution and 95:5 $CHCl_3$-MeOH. The aqueous layer is extracted with 95:5 $CHCl_3$—MeOH (2×), and the combined organic layers are washed with brine, dried over anhydrous sodium sulfate, filtered and concentrated in vacuo. The crude product is purified by flash chromatography on silica gel. Elution with $CHCl_3$—MeOH-ammonium hydroxide (90:9:1) gives an orange solid. The solid is dissolved in acetone (5 mL) and a hot solution of fumaric acid (66 mg, 0.58 mmol) in isopropyl alcohol (2 mL) is added. The mixture is stirred for 30 min in a 50° C. water bath. The solvents are removed in vacuo and the remaining residue is dissolved in acetone (5 mL). The mixture is stirred overnight at rt. The solid precipitate is collected by filtration and washed with acetone. The solid is dried in vacuo overnight to give 150 mg (35%) of the title compound as a light yellow solid: $^1$H NMR (CD$_3$OD) δ 8.6, 8.2, 8.0, 7.9, 6.7, 4.9, 4.5-4.4, 3.9-3.8, 3.5-3.3, 2.4, 2.3-2.2, 2.1, 2.0–1.9.

EXAMPLE 2

N-((3R)1-azabicyclo[2.2.2]oct-3-yl)-2-methyl-1,3-benzoxazole-6-carboxamide.fumarate

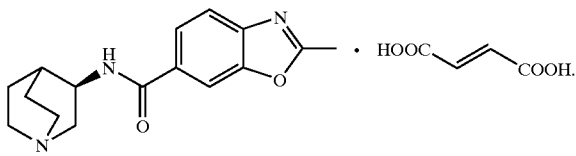

Preparation of 2-methyl-1,3-benzoxazole-6-carboxylic Acid (Acid C2):

A mixture of 4-amino-3-hydroxybenzoic acid (500 mg, 3.7 mmol) and trimethyl orthoacetate (1.0 mL, 7.9 mmol) is heated in an oil bath to 100° C. for 2 h. The mixture is cooled to rt and diluted with MeOH. The resulting solution is filtered through a pad of Celite, and the filtrate is concentrated in vacuo to give Acid C2 as an off-white solid (266 mg, 46%): $^1$H NMR (DMSO-$d_6$) δ 13.1, 8.2, 8.0, 7.7, 2.7.
Coupling:

Example 2 is obtained using Acid C2 according to Method B making non-critical changes. $^1$H NMR (CD$_3$OD) δ 8.1, 7.9, 7.7, 6.7, 4.9, 4.5-4.4, 3.9-3.8, 3.5-3.3, 2.4-2.3, 2.3-2.2, 2.1-2.0, 2.0-1.9.

EXAMPLE 3

N-((3R)1-azabicyclo[2.2.2]oct-3-yl)-1,3-benzoxazole-5-carboxamide.fumarate

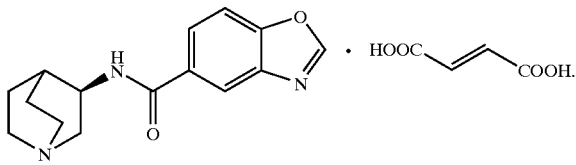

Preparation of 1,3-benzoxazole-5-carboxylic Acid (Acid C3):

A mixture of 4-amino-3-hydroxybenzoic acid (1.0 g, 6.5 mmol) and trimethyl orthoformate (2.0 mL, 18.3 mmol) is heated in an oil bath at 100° C. for 30 h. The mixture is cooled to rt and diluted with MeOH. The resulting solution is filtered through a pad of Celite, and the filtrate is concentrated in vacuo to give Acid C3 as a brown solid (290 mg, 27%): $^1$H NMR (DMSO-$d_6$) δ 13.0, 8.9, 8.3, 8.1, 7.9.
Coupling:

Example 3 is obtained using Acid C3 according to Method B making non-critical changes. $^1$H NMR (CD$_3$OD) δ 8.6, 8.3, 8.0, 7.8, 6.7, 4.5, 3.9-3.8, 3.5-3.3, 2.4, 2.3-2.2, 2.1-2.0, 2.0-1.9.

EXAMPLE 4

N-((3R)1-azabicyclo[2.2.2]oct-3-yl)-2-methyl-1,3-benzoxazole-5-carboxamide.fumarate

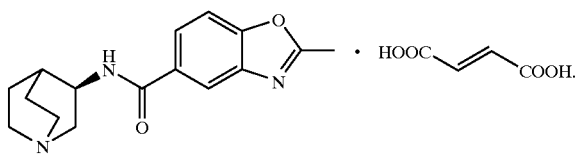

Preparation of 2-methyl-1,3-benzoxazole-5-carboxylic Acid (Acid C4):

A mixture of 4-amino-3-hydroxybenzoic acid (480 mg, 3.1 mmol) and trimethyl orthoacetate (1.0 mL, 7.9 mmol) is heated in an oil bath to 107° C. for 2 h. The mixture is cooled to rt and diluted with MeOH. The resulting solution is filtered through a pad of silica gel and the filtrate is concentrated in vacuo to give Acid C4 as an orange solid (490 mg, 88%): $^1$H NMR (DMSO-$d_6$) δ 13.0, 8.2, 8.0, 7.8, 2.7.
Coupling:

Eample 4 is obtained using Acid C4 according to Method B making non-critical changes. $^1$H NMR (CD$_3$OD) δ 8.2, 7.9, 7.7, 6.7, 4.9, 4.5-4.4, 3.9-3.8, 3.4-3.3, 2.7, 2.4, 2.3-2.2, 2.1, 2.0-1.9.

EXAMPLE 5

N-((3R)1-azabicyclo[2.2.2]oct-3-yl)-1,3-benzothiazole-6-carboxamide.fumarate

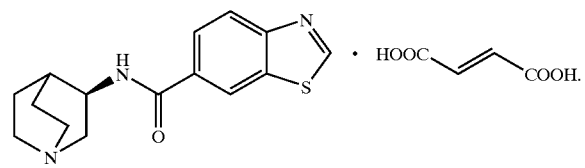

To a stirred solution of 1,3-benzothiazole-6-carboxylic acid (500 mg, 2.8 mmol) and 3-(R)-aminoquinuclidine dihydrochloride (530 mg, 2.7 mmol) in DMF (27 mL) is added DIEA (1.5 mL, 8.4 mmol). The solution is stirred for 10 min, followed by cooling with an ice bath. HATU (1.0 g, 2.7 mmol) is added and the mixture is allowed to warm to rt and stir 16 h. The solvent is removed in vacuo and the remaining residue is partitioned between saturated aqueous potassium carbonate solution and 9:1 CHCl$_3$—MeOH. The aqueous layer is extracted with 9:1 CHCl$_3$—MeOH, and the combined organic layers are washed with brine, dried over anhydrous magnesium sulfate, filtered and concentrated in vacuo to a clear residue. The residue is taken up in acetone (3.0 mL) and a hot solution of fumaric acid (320 mg, 2.8 mmol) in isopropyl alcohol is added. The mixture is warmed in a water bath at 45° C. for 15 min, and then the reaction is concentrated in vacuo. The residue is triturated in acetone (3.0 mL) to afford Example 5 as a white solid (850 mg, 79%): $^1$H NMR (CD$_3$OD) δ 9.4, 8.6, 8.2, 8.1, 6.7, 4.5, 3.9, 3.5-3.3, 2.4, 2.3, 2.1, 2.0.

EXAMPLE 6

N-((3R)1-azabicyclo[2.2.2]oct-3-yl)indane-5-carboxamide.fumarate

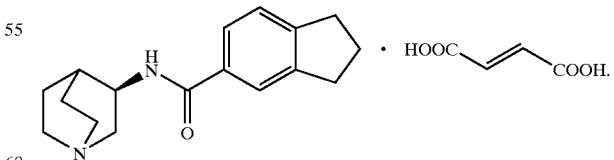

Preparation of 5-indancarboxylic Acid (Acid C6).

To a stirred 6% aqueous sodium hypochlorite solution in an oil bath to 55° C. is added 1-indane-5-yl-ethanone (1.0 g, 6.2 mmol). The solution is stirred at 55° C. for 2 h, followed by cooling to rt. Solid sodium bisulfite is added until the solution became clear. The mixture is diluted with water, followed by aqueous hydrochloric acid (6.0 M). The solid that forms is filtered and washed several times with water. The solid is dried under high vacuum at 60° C. for 5 h to afford Acid C6 as a white solid (0.96 g, 95%): $^1$H NMR (CDCl$_3$) δ 8.0, 7.9, 7.3, 3.0, 2.1.

Method C: Coupling.

To a stirred solution of Acid C6 (500 mg, 3.1 mmol) in dry DMF (30 mL) is added DIEA (1.6 mL, 9.3 mmol), followed by 3-(R)-aminoquinuclidine dihydrochloride (580 mg, 2.9 mmol). The solution is cooled with an ice bath before 1.0 g (2.9 mmol) of HATU is added. The solution is allowed to warm to rt and stir for 16 h. The solvent is removed in vacuo, and the remaining residue is partitioned between saturated aqueous potassium carbonate solution and 9:1 CHCl$_3$—MeOH. The aqueous layer is extracted with 9:1 CHCl$_3$—MeOH, and the combined organic layers are washed with brine, dried over anhydrous magnesium sulfate, filtered and concentrated in vacuo to a clear oil. The oil is dissolved in acetone (2.0 mL) and a hot solution of fumaric acid (320 mg, 2.8 mmol) in isopropyl alcohol (2.0 mL) is added. The solution is heated in a 45° C. water bath for 15 minutes, followed by removal of the solvents in vacuo. The remaining solid is triturated with acetone to afford Example 6 as a white solid (510 mg, 45%): $^1$H NMR (CD$_3$OD) δ 7.7, 7.6, 7.3, 6.7, 4.4, 3.8, 3.5-3.2, 3.0, 2.3-2.0, 1.9.

EXAMPLE 7

N-((3R)-1-azabicyclo[2.2.2]oct-3-yl)-1,3-benzodioxole-5-carboxamide, 4-methylbenzenesulfonate

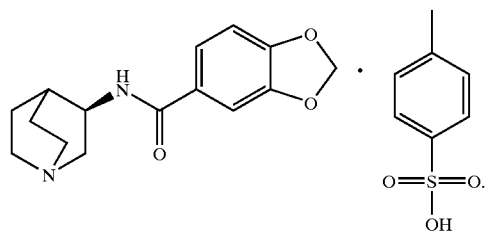

To a stirred suspension of 1,3-benzodioxole-5-carboxylic acid (380 mg, 2.3 mmol) in dry CH$_2$Cl$_2$ (5.0 mL) is added TEA (320 μL, 2.3 mmol), followed by diphenylphosphoryl azide (405 μL, 2.0 mmol). In a separate flask, to a stirred suspension of 3-(R)-aminoquinuclidine dihydrochloride (300 mg, 1.5 mmol) in CH$_2$Cl$_2$ (5.0 mL) is added TEA (530 μL, 3.8 mmol). After 10 min, the aminoquinuclidine solution is rapidly added to the benzodioxole solution. DMF (1.0 mL) is added, and the combined mixture is stirred for 24 h at rt. The reaction mixture is partitioned between saturated aqueous potassium carbonate solution and CH$_2$Cl$_2$. The aqueous layer is extracted with CH$_2$Cl$_2$, and the combined organic layers are washed with brine, dried over anhydrous magnesium sulfate, filtered and concentrated in vacuo to a clear residue. The crude product is purified by flash chromatography on silica gel. Elution with CHCl$_3$—MeOH-ammonium hydroxide (90:9:1) gives 130 mg (31%) of a white foam. The foam (125 mg, 0.46 mmol) is dissolved in EtOAc (1.0 mL) and a solution of p-toluenesulfonic acid monohydrate (90 mg, 0.48 mmol) in MeOH (0.5 mL) is added. The solution is allowed to stand overnight. The solid that forms is filtered and dried in vacuo at 50° C. for 48 h to afford the title compound (160 mg, 76%): $^1$H NMR (CD$_3$OD) δ 7.7, 7.5, 7.4, 7.3, 6.9, 6.1, 4.4, 3.8, 3.5-3.2, 2.4, 2.3, 2.2, 2.1, 1.9.

EXAMPLE 8

N-[(3R)-1-azabicyclo[2.2.2]oct-3-yl][1,3]oxazolo[5,4-c]pyridine-6-carboxamide

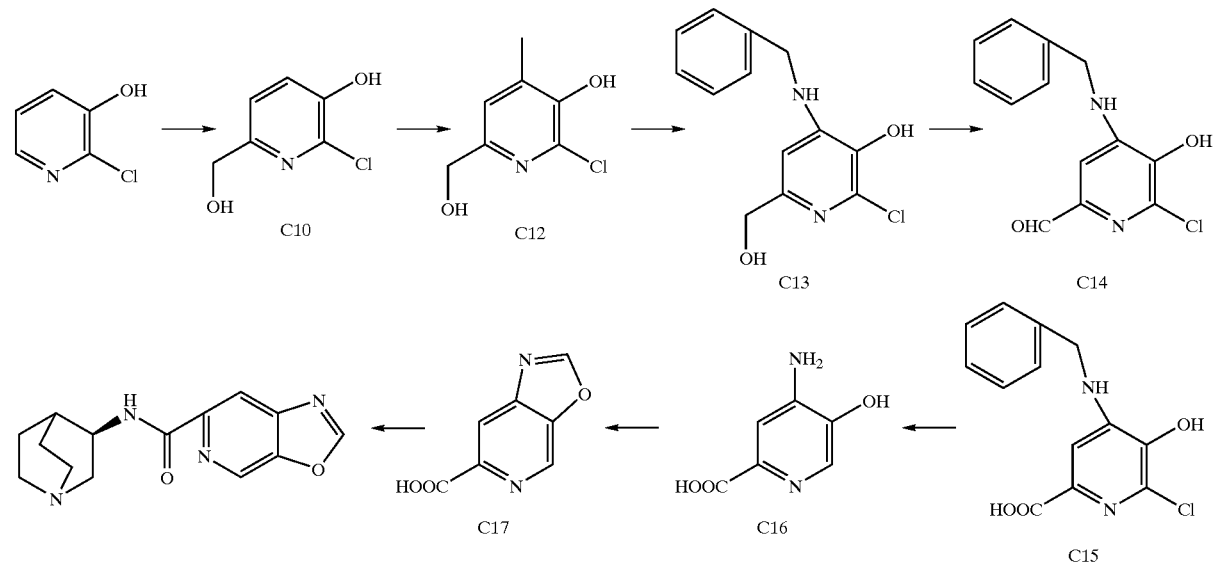

Preparation of the Acid

2-Chloro-3-pyridinol (20.0 g, 0.154 mole), NaHCO₃ (19.5 g, 0.232 mole, 1.5 equ), and 150 mL of water are placed in a flask. The flask is placed in an oil bath at 90° C., and after 5 minutes, 37% aqueous formaldehyde (40.5 mL, 0.541 mole, 3.5 equ) is added in six unequal doses in the following order: 12 mL, 3×8 mL, then 2.2 mL all at 90-minute intervals and then the final 2.3 mL after the reaction had stirred for 15 h at 90° C. The reaction is stirred at 90° C. for another 4 h and then is cooled by placing the flask in an ice bath. The pH of the reaction is then adjusted to 1 using 6N HCl. The reaction is stirred for 1.5 h in an ice bath allowing an undesired solid to form. The undesired solid is removed by filtration, and the filtrate is extracted seven times with EtOAc. The combined organic extracts are concentrated in vacuo, toluene is added to the flask and removed in vacuo to azeotrope water, and then CH₂Cl₂ is added and removed in vacuo to obtain 2-chloro-6-(hydroxymethyl)-3-pyridinol (C10) as a pale yellow solid (81% yield) sufficiently pure for subsequent reaction. MS (EI) for C₆H₆ClNO₂, m/z: 159(M)⁺.

2-Chloro-6-(hydroxymethyl)-3-pyridinol (C10) (11.6 g, 72.7 mmol) and NaHCO₃ (18.3 g, 218 mmol) are added to 200 mL water. The mixture is stirred until homogeneous, the flask is placed in an ice bath, iodine (19.4 g, 76.3 mmol) is added, and the reaction is stirred over the weekend at rt. The pH of the mixture is adjusted to 3 with 2N NaHSO₄, and the mixture is extracted with 4×50 mL EtOAc. The combined organic layer is dried over anhydrous MgSO₄, is filtered and the filtrate is concentrated in vacuo to a yellow solid. The crude solid is washed with EtOAc to provide 2-chloro-6-(hydroxymethyl)-4-iodo-3-pyridinol (C12) as an off-white solid (62% yield), and the filtrate is concentrated to a small volume and is chromatographed over 250 g silica gel (230–400 mesh) eluting with 2.5:4.5:4:0.1 EtOAc/CH₂Cl₂/hexane/acetic acid. The desire fractions are combined and concentrated to afford an additional pure C12 (12% yield). MS (EI) for C₆H₅ClINO₂, m/z: 285(M)⁺.

4-(Benzylamino)-2-chloro-6-(hydroxymethyl)-3-pyridinol (C13) may be produced by amination of 2-chloro-6-(hydroxymethyl)-4-iodo-3-pyridinol (C12) with benzylamine under palladium catalysis. Amination of aryl iodides with primary amines such as benzylamine under palladium catalysis is generally described in a review by B. H. Yang and S. L. Buchwald in *J. Organomet. Chem.*, 576, 125–146, 1999 and in greater detail in the references therein.

C13 may be oxidized to 4-(benzylamino)-2-chloro-3-hydroxypyridine-6-carboxaldehyde (C14) under a wide variety of conditions (e.g., TPAP and NMO in CH₂Cl₂). C14 may be oxidized to produce the corresponding carboxylic acid C15 using an oxidizing reagent such as NaClO₂ and KH₂PO₄ in DMSO/H₂O or Ag₂O, or hydrogen peroxide or ruthenium tetroxide.

Removal of the benzyl group and the chloro group of Acid C15 may be accomplished by utilizing hydrogen or a hydrogen source (e.g., cyclohexene, cyclohexadiene, ammonium formate, hydrazine, etc.) in the presence of Pd/C or other catalyst, under a variety of conditions and in various solvents, to produce 4-amino-5-hydroxypyridine-2-carboxylic acid (Acid C16).

Cyclocondensation of Acid C16 with trimethyl orthoformate in the presence of catalytic para-toluenesulfonic acid may be conducted to produce [1,3]oxazolo[5,4-c]pyridine-6-carboxylic acid (Acid C17).

Coupling

Example 8 is obtained using Acid C17 according to Method B making non-critical changes. The free base can be made into a suitable salt.

EXAMPLE 9

N-[(3R)-1-azabicyclo[2.2.2]oct-3-yl]-2-benzoisothiophene-5-carboxamide

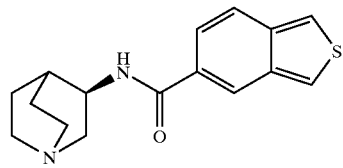

Acid C21 can be made by the saponification of the methyl ester C20, which can be made pursuant to Wynberg, Hans, et al., *Recl. Trav. Chim. Pays-Bas* (1968), 87(10), 1006–1010. Acid C21 can then be coupled with the aminoquinuclidine using Method B with non-critical changes to provide Example 9 as the free base that can be made into a suitable salt.

EXAMPLE 10

N-[(3R)-1-azabicyclo[2.2.2]oct-3-yl]-1,3-benzothiazole-5-carboxamide.fumarate

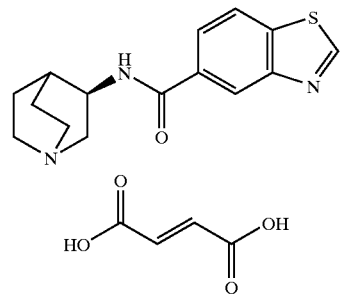

A solution of sodium sulfide.nanohydrate (1.15 g, 4.9 mmol) in methanol-water (ca. 10 mL, 1:1) is warmed on a hot plate. To this solution is added elemental sulfur (150 mg, 4.6 mmol). Heating is continued for 15 min before the solution is poured into a separate solution of 1.0 g (4.6 mmol) of methyl 4-chloro-3-nitrobenzoate (see: Kuene, *J. Am. Chem. Soc.* 1962, 48, 837.) in MeOH (5.0 mL). The mixture is stirred for 30 min, followed by cooling in a refrigerator overnight. The solid precipitate is filtered, washed with water and methanol, and dried in vacuo at 50° C. to afford 650 mg (65%) of dimethyl 4,4'-dithio-bis-(3-nitrobenzoate) as a yellow solid: ¹H NMR (400 MHz, CDCl₃) δ 9.0, 8.2, 7.9, 4.0.

To a stirred solution of dimethyl 4,4'-dithio-bis-(3-nitrobenzoate) (900 mg, 2.12 mmol) in ethanol is added tin powder (1.91 g, 17.0 mmol). The mixture is heated in a 70° C. oil bath for 30 minutes before 2.8 mL of concentrated hydrochloric acid is added drop-wise. After complete addition, the mixture is stirred for an additional 10 min, followed by cooling to RT. The reaction mixture is filtered and the fitrate is concentrated in vacuo to a solid. The solid is washed with 1.0M aqueous hydrochloric acid and dried in vacuo to afford a yellow solid. The solid (750 mg, 3.42 mmol) is suspended in formic acid (4 mL) in a 100° C. oil bath. Zinc dust (15 mg) is added to the reaction. The mixture is stirred for 10 min, followed by cooling to RT. The mixture is diluted with water and extracted with EtOAc. The organic layer is dried over MgSO₄, filtered and concentrated in vacuo to afford 640 mg (97%) of methyl 1,3-benzothiazole-5-carboxylate as a yellow solid: $^1$H NMR (400 MHz, CDCl$_3$) δ 9.1, 8.9, 8.2, 8.1, 4.0.

To a stirred solution of methyl 1,3-benzothiazole-5-carboxylate (290 mg, 1.5 mmol) in MeOH (20 mL) is added sodium hydroxide (10 mL of a 5% aqueous solution). The mixture is heated in a 65° C. oil bath for 30 min, followed by cooling to RT. The mixture is diluted with water and extracted with hexanes-ether (1:1). The organic layer is discarded and the aqueous layer is acidified with concentrated hydrochloric acid to pH=1. The aqueous layer is extracted with ether. The ethereal layer is dried over MgSO$_4$, filtered and concentrated in vacuo to a yellow powder for 1,3-benzothiazole-5-carboxylic acid (260 mg, 98%): $^1$H NMR (400 MHz, DMSO-d$_6$) δ 13-12.5, 9.5, 8.6, 8.3, 8.0.

Example 10 is obtained using 1,3-benzothiazole-5-carboxylic acid according to the coupling procedure described for making Example 5 to afford 300 mg (86%) of Example 10 as a white solid. $^1$H NMR (MeOH-d$_4$) δ 9.3, 8.6, 8.2, 8.0, 6.7, 4.5, 3.9, 3.5-3.3, 2.4, 2.3, 2.1 , 2.0.

EXAMPLE 11

N-[(2S,3R)-2-methyl-1-azabicyclo[2.2.2]oct-3-yl]-1,3-benzothiazole-6-carboxamide hydrochloride

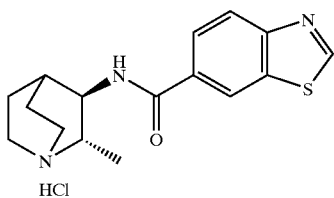

Preparation of (2S,3R)-2-methyl-1-azabicyclo[2.2.2]octan-3-amine dihydrochloride:

A mixture of 2-methylene-3-quinuclidinone dihydrate hydrochloride (27.2 g, 0.13 mol, 1 eq) and K$_2$CO$_3$ (86.0 g, 0.62 mol, 4.8 eq) is dissolved in 130 mL water and 250 mL CH$_2$Cl$_2$ and stirred vigorously. After 3 days, the layers are separated and the aqueous layer is extracted with CH$_2$Cl$_2$. The combined organic layers are dried (MgSO$_4$), filtered and concentrated to give 17.8 g (100%) of 2-methylenequinuclidin-3-one as a yellow oil. MS (ESI) for C$_8$H$_{11}$NO m/z 138.1 (M$^+$).

2-Methylenequinuclidin-3-one (17.8 g, 0.13 mol, 1 eq) is dissolved in 40 mL MeOH in a Parr hydrogenation bottle. A THF slurry of 10% Pd/C (0.57 g) is added. The mixture is hydrogenated for 45 min at 45 psi, recharging as needed. The mixture is filtered through a pad of Celite. The Celite is washed with excess MeOH. The solution is concentrated to give a solid and a yellow oil. The mixture is taken up in ether, filtered and concentrated to provide 16.2 g (90%) of 2-methylquinuclidin-3-one. MS (ESI) for C$_8$H$_{13}$NO m/z 140.2 (M$^+$).

2-Methylquinuclidin-3-one (39.6 g, 0.28 mol, 1 eq) and hydroxylamine hydrochloride (20.0 g, 0.29 mol, 1.01 eq) are dissolved in 170 mL absolute EtOH. The mixture is heated under reflux until a clear solution develops (about 20 min), after which is immediately followed by formation of a white precipitate. The reaction is cooled and allowed to stand overnight. The mixture is cooled in an ice bath, the solids are filtered and dried (house vacuum) to provide 46.4 g of (3E/Z)-2-methyl-1-azabicyclo[2.2.2]octan-3-one oxime hydrochloride. A second crop of 2.4 g is also obtained. Overall yield is 48.8 g (90%). The 2-methyl-1-azabicyclo[2.2.2]octan-3-one oxime hydrochloride is a 4:1 mixture of oxime isomers. MS (ESI) for C$_8$H$_{14}$N$_2$O m/z 154.8 (M$^+$). Partial $^1$H NMR (400 MHz, DMSO) δ 4.39 (0.2H), 4.29 (0.8H), 1.57 (0.6H), 1.47 (2.4H).

A solution of sodium n-propoxide (prepared from 5.5 g sodium (0.24 mol) and 100 mL n-propanol) is added dropwise to a suspension of (3E/Z)-2-methyl-1-azabicyclo[2.2.2]octan-3-one oxime hydrochloride (45.8 g, 0.24 mol, 1 eq) in 150 mL n-propanol. After complete addition, 250 mL of n-propanol is added, and the mixture is heated under reflux. Sodium (55.2 g, 2.40 mol, 10 eq) is added in portions to the refluxing mixture. The mixture is heated under reflux overnight. After about 14 h, the mixture is cooled, water is added and the layers are separated. The n-propanol layer is washed with brine and dried (MgSO$_4$). The combined aqueous layers are extracted with CHCl$_3$ and dried (MgSO$_4$). The combined, dried organic layers are treated with about 70 mL concentrated HCl. The solvent is removed in vacuo. Absolute EtOH is added, and the solvent is removed. The sequence is repeated 2-3 times with fresh EtOH until a white solid formed. Absolute EtOH is added, the solids are filtered and dried (vacuum oven, about 60° C.) to provide 36.5 g of trans 3-amino-2-methylquinuclidine dihydrochloride. MS (ESI) for C$_8$H$_{16}$N$_2$ m/z 141.3 (M$^+$). Additional material is obtained from the mother liquor: 7.8 g (2$^{nd}$ crop) and 1.5 g (3$^{rd}$ crop); this material is a mixture of both trans and cis isomers.

4-Chlorobenzoic acid (26.3 g, 0.17 mol, 1.1 eq) and TEA (106 mL, 0.76 mol, 5 eq) are dissolved in 300 mL THF. Diphenylphosphoryl chloride (32.0 mL, 0.17 mol, 1.1 eq) is added dropwise. After 1 h, trans 2-methylquinuclidin-3-amine dihydrochloride (32.6 g, 0.15 mol, 1 eq) is added. The mixture is allowed to stir at RT overnight. 1N NaOH (about 100 mL) is added, and the pH is adjusted to pH 11 with 50% NaOH and about 50 g K$_2$CO$_3$. The layers are separated. The aqueous layer is extracted with CHCl$_3$. The combined organic layers are dried (MgSO$_4$), filtered and concentrated. The residue is taken up in heptane and concentrated to give 35.1 g (82%) of 4-chloro-N-(2-methyl-1-azabicyclo[2.2.2]oct-3-yl)phenyl-2-carboxamide as a light yellow solid. The enantiomers are separated on a 5×50 cm Chiralcel OD column at 30° C., eluting with 15% IPA/heptane +0.1% DEA at 90 mL/min to provide 17.4 g of the eutomer at about 97% ee. The p-TsOH salt is prepared and recrystallized from EtOH/EtOAc. [α]$^{25}_D$=+3° (c 0.96, methanol). HRMS (FAB) calcd for C$_{15}$H$_{19}$ClN$_2$O+H 279.1264, found 279.1272.

A solution of 4-chloro-N-[(2S,3R)-2-methyl-1-azabicyclo[2.2.2]oct-3-yl]benzamide (17.2 g, 61.7 mmol) in absolute EtOH (70 mL) and concentrated HCl (70 mL) is heated under reflux for about 64 h. The reaction is monitored for disappearance of starting amide by reverse phase HPLC (ZORBAX Eclipse XDB-C8, 4.6 mm×15 cm, 80:12:8H$_2$O/CH$_3$CN/IPA). The solvent is removed in vacuo. The residue is dissolved/suspended in EtOH and the solvent is removed (twice). The solid is suspended in boiling EtOH, filtered and dried (vacuum oven, about 60° C.) to provide 8.8 g (67%) of N-(2S,3R)-2-methyl-1-azabicyclo[2.2.2]octan-3-amine dihydrochloride as a white solid. MS (EI) m/z 141.2 (M$^+$).

Coupling:

1,3-Benzothiazole-6-carboxylic acid (0.18 g, 1.0 mmol), HATU (0.465 g, 1.22 mmol) and (2S,3R)-2-methyl-1-azabicyclo[2.2.2]octan-3-amine dihydrochloride (0.215 g, 10 mmol) are suspended in 15mL CH$_3$CN. DIEA (1.4 mL, 8.0 mmol) is added dropwise. The reaction is warmed to RT. After 48 h, the solvent is removed in vacuo. The residue is taken up in CHCl$_3$, 1N NaOH is added and the mixture is extracted with CHCl$_3$. The combined organic layers are dried (MgSO$_4$), filtered and concentrated. The residue is purified by chromatography (Biotage 40S, 90:9:1 CHCl$_3$/MeOH/NH$_4$OH). The hydrochloride salt is prepared and recrystallized from MeOH/EtOAc to provide 0.123 g (36%) of the product. HRMS (FAB) calculated for C$_{16}$H$_{19}$N$_3$OS+H 302.1327, found 302.1311.

EXAMPLE 12

N-[(3R)-1-azabicyclo[2.2.2]oct-3-yl]-3-methyl-1,2-benzisoxazole-6-carboxamide

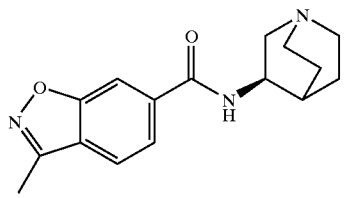

3-Hydroxybenzoic acid (13.8 g, 100 mmol) is dissolved in concentrated NH$_4$OH (200 mL) using an overhead stirrer and is treated slowly dropwise with a solution of iodine (23.4 g, 92 mmol) and KI (18.26 g, 110 mmol) in water (100 mL). The solution is stirred for 1 h at rt and then treated rapidly dropwise with concentrated HCl (180 mL). The white solid is collected via filtration, rinsed with water and dried overnight [by pulling air through the solid] in vacuo to afford 13.05 g (54%) of 3-hydroxy-4-iodobenzoic acid as a tan solid. $^1$H NMR (DMSO-d$_6$): δ 7.13, 7.43, 7.80, 10.71, 12.98 ppm.

3-Hydroxy-4-iodobenzoic acid (12.55 g, 47.5 mmol) is dissolved in MeOH (200 mL), treated slowly dropwise with thionyl chloride (32.3 mL, 442.9 mmol) at rt, then heated to reflux for 20 h. The mixture is concentrated to dryness and partitioned between CH$_2$Cl$_2$ (100 mL) and saturated NaHCO$_3$ (50 mL). Not all of the residue is solubilized, so the mixture is filtered and the solid is washed with a small amount of CH$_2$Cl$_2$ and MeOH. The original filtrate and the organic washes are combined, concentrated to dryness, dissolved in 10% MeOH/CH$_2$Cl$_2$ (200 mL), diluted with water (50 mL) and the layers separated. The organics are washed with saturated NaHCO$_3$ (2×50 mL), then water (50 mL), dried over anhydrous Na$_2$SO$_4$ and concentrated to a tan solid. This solid is triturated with CH$_2$Cl$_2$ (50 mL) and filtered. The two solids are combined to afford 9.4 g (70%) of methyl 3-hydroxy-4-iodobenzoate as a beige solid. HRMS (FAB) calcd for C$_8$H$_7$IO$_3$+H$_1$: 278.9520, found 278.9521.

Methyl 3-hydroxy-4-iodobenzoate (5.22 g, 18.8 mmol) is combined with trimethylsilylacetylene (3.71 mL, 26.3 mmol), bis(triphenylphosphine)palladium dichloride (386 mg, 0.55 mmol) and cuprous iodide (54 mg, 0.28 mmol) in THF (20 mL) CHCl$_3$ (40 mL) in a dry flask, under nitrogen. TEA (8.14 mL<58.4 mmol) is added and the mixture is heated to 50° C. for 4 h. The mixture is diluted with CHCl$_3$ (60 mL), washed with 5% HCl (2×40 mL), dried over anhydrous MgSO$_4$ and concentrated to a brown paste (8.31 g). The crude material is chromatographed over a standard 90 g Biotage column, eluting with 10% EtOAc/hexane (1 L) followed by 15% EtOAc/hexane (1 L). The appropriate fractions are combined and concentrated to afford 4.22 g (91%) of methyl 3-hydroxy-4-[(trimethylsilyl)ethynyl]benzoate as a yellow solid. HRMS (FAB) calcd for C$_{13}$H$_{16}$O$_3$SI+H$_1$: 249.0947, found 249.0947.

Methyl 3-hydroxy-4-[(trimethylsilyl)ethynyl]benzoate (540 mg, 2.17 mmole) is combined with 4 ml formic acid under nitrogen. The reaction is warmed to 80° C. for 12 h, is cooled to rt, and the volatiles are removed in vacuo. The black residue is chromatographed over 25 g silica gel (230–400 mesh) eluting with 15% EtOAc/hexane. The appropriate fractions are combined and concentrated to provide 350 mg (83%) of methyl 4-acetyl-3-hydroxybenzoate as a pale yellow solid. $^1$H NMR (CDCl$_3$) δ 2.70, 3.95, 7.54, 7.64, 7.82, 12.10 ppm.

Methyl 4-acetyl-3-hydroxybenzoate (350 mg, 1.8 mmole) is combined with 5 ml absolute EtOH. The solution is treated with hydroxylamine hydrochloride (125 mg, 1.8 mmole) dissolved in 0.9 ml 2N aqueous NaOH, and the reaction is stirred overnight at rt. The volatiles are removed in vacuo and the residue is washed with H$_2$O, collected, and dried to give 294 mg (78%) of methyl 3-hydroxy-4-[N-hydroxyethanimidoyl]benzoate as a tan solid. MS (EI) m/z: 209 (M$^+$).

Methyl 3-hydroxy-4-[N-hydroxyethanimidoyl]benzoate (250 mg, 1.19 mmole) is combined with triphenylphosphine (446 mg, 1.7 mmole) in 14 ml dry THF in a dry flask under nitrogen. The solution is treated slowly dropwise with N,N'-diethylazidodicarboxylate (268 mL, 1.7 mmole) in 10 ml dry THF. The reaction is stirred 4 h at rt. The volatiles are removed in vacuo and the residue is chromatographed over 30 g silica gel (230-400 mesh) eluting with 10% EtOAc/hexane. The appropriate fractions are combined and concentrated to provide 125 mg (55%) of methyl 3-methyl-1,2-benzisoxazole-6-carboxylate slightly contaminated (<10%) with methyl 4-acetyl-3-hydroxybenzoate. $^1$H NMR (CDCl$_3$) δ 2.64, 4.00, 7.70, 8.01, 8.25 ppm.

Methyl 3-methyl-1,2-benzisoxazole-6-carboxylate (170 mg, 0.89 mmole) is dissolved in 6 ml MeOH under nitrogen. The solution is treated with 2N aqueous NaOH (1 ml, 2 mmole) and the mixture is stirred 4 h at rt. The volatiles are removed in vacuo and the residue is dissolved in 4 ml water. The pH of the solution is adjusted to 3 with 10% aqueous HCl, the white precipitate is collected, is washed with water, and is dried to give 144 mg (92%) of 3-methyl-1,2-benzisoxazole-6-carboxylic acid as a white solid. MS m/z (ESI): 176.2 (M−H)$^-$.

3-Methyl-1,2-benzisoxazole-6-carboxylic acid (139 mg, 0.78 mmole) is combined with (3R)-aminoquinuclidine dihydrochloride (156 mg, 0.78 mmole) and DIEA (272 μL, 1.56 mmole) in 3 ml DMF under nitrogen. The mixture is treated with HATU (296 mg, 0.78 mmole), and the reaction is stirred overnight at rt. The volatiles are removed in vacuo and the residue is partitioned between 1×10 ml 10% MeOH/CHCl$_3$ and 1×10 ml 1:1 saturated sodium chloride/conc. NH$_4$OH. The aqueous layer is washed with 1×10 ml CHCl$_3$ and the combined organic layer is dried over K$_2$CO$_3$. The dried organic layer is concentrated in vacuo to give an amber residue. The crude material is chromatographed over 15 g silica gel (230–400 mesh) eluting with 7% MeOH/CHCl$_3$+ 1% conc. NH$_4$OH. The appropriate fractions are combined and concentrated to give a pale foam. The foam is crystallized from Et$_2$O to provide 163 mg (72%) of N-[(3R)-1-azabicyclo[2.2.2]oct-3-yl]-3-methyl-1,2-benzisoxazole-6-carboxamide as an off-white solid. MS (EI) m/z: 285 (M$^+$).

EXAMPLE 13

N-[(3R)-1-azabicyclo[2.2.2]oct-3-yl]-3-methyl-1,2-benzisoxazole-5-carboxamide

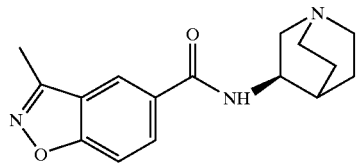

Example 13 is obtained according to the methods discussed for preparing Example 12 starting with 4-hydroxybenzoic acid to make 3-methyl-1,2-benzisoxazole-5-carboxylic acid. Example 13 is obtained in 79% yield for the last step (coupling). MS (EI) m/z: 285 (M+).

EXAMPLE 14

N-[(3R)-1-azabicyclo[2.2.2]oct-3-yl]-1H-indazole-6-carboxamide.fumarate

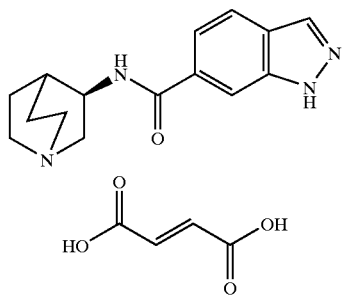

To a stirred solution of 3-amino-4-methylbenzoic acid (5.0 g, 33 mmol) in a mixture of water (50 mL) and concentrated hydrochloric acid (15 mL) in an acetone-crushed ice bath is added a solution of sodium nitrite in water (12 mL) dropwise. The solution is stirred for 10 min, followed by the addition of tert-butyl mercaptan (1.8 mL, 16 mmol). The mixture is stirred for 1 h. The solid precipitate is filtered, washed with water and dried in vacuo to obtain 3.85 g (95%) of 3-[(E)-(tert-butylthio)diazenyl]-4-methylbenzoic acid as a tan solid: $^1$H NMR (400 MHz, DMSO-$d_6$) δ 13.2, 7.8, 7.5, 7.3, 2.1, 1.6.

To a stirred solution of potassium tert-butoxide (8.1 g, 73 mmol) in DMSO (30 mL) was added a solution of 3-[(E)-(tert-butylthio)diazenyl]-4-methylbenzoic acid (1.9 g, 7.3 mmol) at RT. The mixture was stirred overnight, followed by the adition of ice water. The aqueous layer was extracted with ethyl acetate. The organic layer was dicarded. The pH of the aqueous layer was adjusted to 4-5 with aqueous 1N HCl. The aqueous layer was extracted with ethyl acetate. The organic layer was washed with brine, dried over MgSO$_4$, filtered and concentrated in vacuo to afford 800 mg (97%) of 1H-indazole-6-carboxylic acid as a tan solid: $^1$H NMR (400 MHz. DMSO-$d_6$) δ 13.4, 13.0, 8.2, 8.1, 7.9, 7.7.

To a stirred solution of 1H-indazole-6-carboxylic acid (160, 1.0 mmol) in anhydrous DMF (10 mL) are added N,N-DIEA (520 μL, 3.0 mmol) and 3-(R)-aminoquinuclidine dihydrochloride (190 mg, 0.95 mmol). The mixture is cooled to 0° C., and HATU (360 mg, 0.95 mmol) is added in one portion. The reaction mixture is allowed to warm to rt and stir overnight. The solvent is removed in vacuo and the residue is partitioned between saturated aqueous potassium carbonate solution and chloroform. The aqueous layer is extracted with chloroform (2x). The combined organic layers are washed with brine, dried over anhydrous sodium sulfate, filtered and concentrated in vacuo. The crude product is purified by flash chromatography on silica gel. Elution with CHCl$_3$-MeOH-NH$_4$OH (89:9:1) gives the carboxamide as a clear solid (220 mg, 87%).

To a stirred solution of the carboxamide (220 mg, 0.82 mmol) in MeOH (10 mL) is added a warm solution of fumaric acid (95 mg, 0.82 mmol) in MeOH (10 mL). The mixture is stirred for 10 min at 50° C. The solvent is removed in vacuo and the remaining residue is diluted with acetone (15 mL) and water (few drops). The mixture is stirred overnight at rt. The solid is collected by filtration, washed with acetone, and dried in vacuo overnight to afford 240 mg (74%) of Example 14 as a white solid. $^1$H NMR (400 MHz, CD$_3$OD) δ 8.2, 8.1, 7.9, 7.6, 6.7, 4.5, 3.9, 3.5-3.3, 2.4, 2.3, 2.1, 1.9.

The benzothiazole and benzimidazole intermediates can be prepared using the methods as shown in Scheme 3 or Scheme 4, respectively. The benzoxazole intermediates can be prepared using methods described in Campaigne, E.; Van Verth, J. E., *J. Org. Chem.*, 1958, 23, 1344–1346, whereby the requisite o-aminophenol is treated with diethyloxalate. An alternate preparation of these compounds utilizes an approach described in *Pol. J. Pharm.*, 1984, 683–688, wherein the o-aminophenol is treated with glycolic acid. The resultant alcohol is then oxidized with KMnO$_4$ to afford the desired benzoxazole-2-carboxylic acid derivative. Similar approaches can be followed to afford the desired benzothiazole and benzimidazole derivatives.

Scheme 3

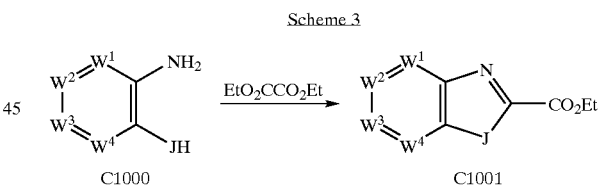

Scheme 4

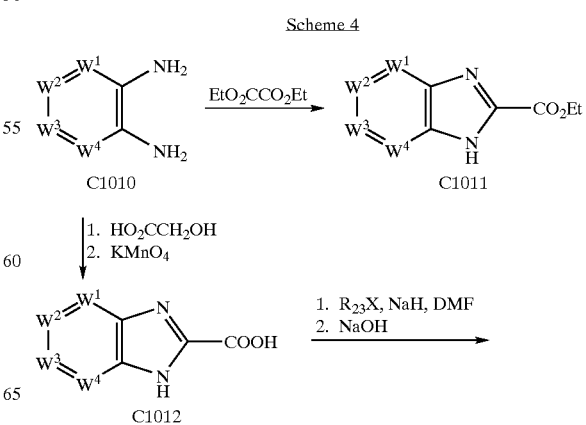

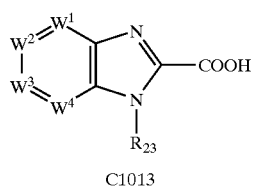

Scheme 5

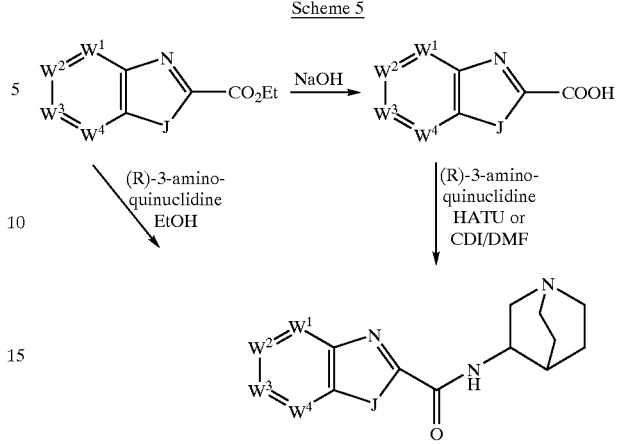

Alternatively, for where there is substitution on the imidazole:

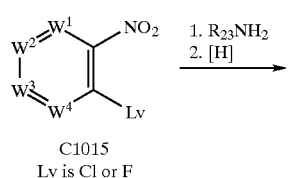

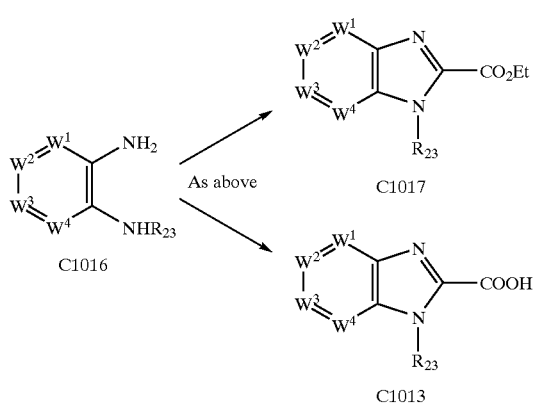

2-Carboethoxy derivatives can be directly coupled to (R)-3-aminoquinuclidine upon heating in the ester in ethanol at reflux. An alternate route entails subjecting the ester to hydrolysis providing a carboxylic acid. The carboxylic acid can then be coupled to (R)-3-aminoquinuclidine using a variety of amide bond coupling reagents.

EXAMPLE 1001

N-[(3R)-1-Azabicyclo[2.2.2]oct-3-yl]-1,3-benzothiazole-2-carboxamide hydrochloride

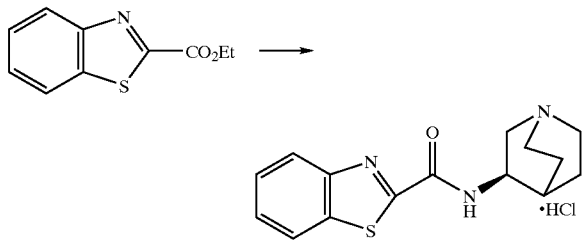

The synthetic route to other compounds of interest is shown in Scheme 4. Heating C1010 in neat diethyl oxalate provides C1011. Alternatively, heating C1010 in neat glycolic acid provides an alcohol which is subsequently oxidized with $KMnO_4$ to afford C1012 (*Pol. J. Pharm.* 1984, 683–688). In yet another approach to compounds of the present invention, 2-halonitroaryl or heteroaryl compounds are subjected to amines wherein a well documented ipso-displacement of the halogen group occurs to provide a nitro-derivative that can be reduced, using methods well known to those or ordinary skill in the art, yielding C1016. Finally, using methods described earlier, C1016 can be transformed into C1013 directly using diethyloxalate or into C1017 using glycolic acid followed by oxidation of the alcohol to the carboxylic acid.

The coupling of 3-aminoquinuclidine occurs using either the carboxylic acids, such as C1012 or C1013, or the ethyl esters, such as C1001, C1011, or C1017, as shown in Scheme 5.

Step 1001a: Preparation of Ethyl 2-benzothiazolecarboxylate

A solution of 2-aminothiophenol (10.7 mL, 0.1 mol) in diethyl oxalate (27.3 mL, 0.2 mol) is heated at reflux for 4 hr. The solution is cooled to rt and poured into a solution consisting of water (150 mL), conc. HCl (50 mL) and 95% EtOH (70 mL). With stirring, the oil dissolved and a solid formed. The solution is cooled in an ice bath, the solid is collected by vacuum filtration and the solids are washed with a solution consisting of EtOH/water (25/75) to afford a dark solid. This material is purified by crystallization from hot (68° C.) ligroin to yield ethyl 2-benzothiazolecarboxylate (7.5 g, 36%). Elemental analysis for $C_{10}H_9NO_2S$: Calc: C, 57.95; H, 4.38; N, 6.76. Found: C, 57.99; H, 4.28; N, 6.78.

Step 1001b: Coupling

Ethyl 2-benzothiazolecarboxylate (0.918 g, 4.43 mmol) is dissolved in MeOH (20 mL) and 2 N NaOH (3.0 mL) is added. The mixture is stirred at rt for 2 hr, then lyophilized to afford the sodium salt of the 2-benzothiazolecarboxylate. The crude salt is dissolved in THF (25 mL) and cooled to 0° C. To this is added 3-(R)-aminoquinuclidine dihydrochloride, DIEA (1.7 g, 2.3 mL, 13 mmol) and HATU (1.71 g, 4.49 mmol). The mixture is stirred at rt for 6 hr, diluted with $CH_2Cl_2$ (15 mL) and washed with 1 N NaOH followed by sat. aq. $NaHCO_3$. The material is purified by passage through acidic ion exchange resin. The free base is taken up in 1 M HCl/MeOH (8 mL) and stirred for 1.5 hr. Isopropanol and Et$_2$O are added and the solid is isolated by vacuum filtration to afford Example 1001 in 25% yield. Elemental analysis for C$_{15}$H$_{17}$N$_3$OS HCl: Calc: C, 55.63; H, 5.60; N, 12.98. Found: C, 54.74; H, 5.73; N, 12.69. Theo.: C, 54.87; H, 5.68; N, 12.80.

EXAMPLE 1002

N-[(3R)-1-Azabicyclo[2.2.2]oct-3-yl]-6-fluoro-1,3-benzothiazole-2-carboxamide hydrochloride

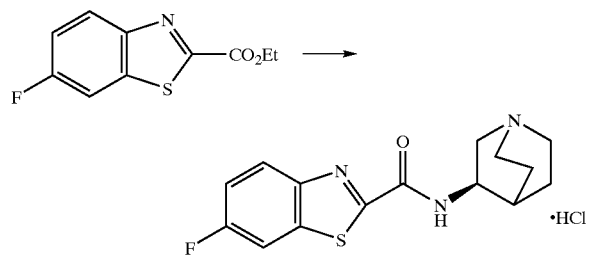

Step 1002a: Preparation of Ethyl 6-fluoro-1,3-benzothiazole-2-carboxylate

A solution of 5-fluoro-2-aminobenzenethiol (0.94 g, 6.6 mmol) in diethyl oxalate (1.8 mL, 13 mmol) is heated at reflux for overnight. The solution is poured into a mixture of water (9.8 mL), conc. HCl (3.3 mL), and EtOH (4.6 mL). The material is extracted with CHCl$_3$ (3×100 mL). The combined organic extracts are dried over MgSO$_4$, filtered and concentrated to yield an oil. The material is purified by chromatography (25% hexanes/75% CHCl$_3$) to afford a solid that is recrystallized from petroleum ether (0.16 g, 11%). MS for C$_{10}$H$_8$NO$_2$SF: m/z 226 (M+H)$^+$.

Step 1002b: Coupling 3-(R)-Aminoquinuclidine dihydrochloride (89 mg, 0.68 mmol) is dissolved in EtOH (10 mL). Ethyl 6-fluoro-1,3-benzothiazole-2-carboxylate (140 mg, 0.62 mmol) is added and the solution is heated at reflux overnight. MS indicated starting material remained; therefore, additional 3 (R)-aminoquinuclidine dihydrochloride (90 mg, 0.7 mmol) is added and the solution is heated for an additional 24 hr. The solution is concentrated and the material is purified by chromatography (10% MeOH, 89.5% CHCl$_3$, 0.5% NH$_4$OH). The material is crystallized from 3 M HCl/MeOH to afford Example 1002 (189 mg, 79%). MS C$_{15}$H$_{16}$N$_3$SFO: m/z 306 (M+H)$^+$.

EXAMPLE 1004

N-[(3R)-1-Azabicyclo[2.2.2]oct-3-yl]-3H-imidazo[4,5-b]pyridine-2-carboxamide hydrochloride

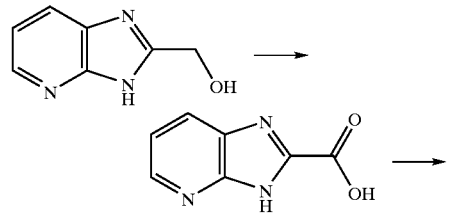

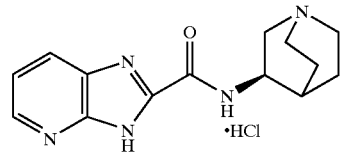

Step 1004a: Preparation of 3H-imidazo[4,5-b]pyridin-2-ylmethanol 2,3-Diaminopyridine (0.74 g, 6.8 mmol) and glycolic acid (1.1 g, 15 mmol) are heated at reflux for 4.5 hr. The solution is cooled to rt, and sat. aq. NaHCO$_3$ is added until the solution is basic. The resulting solids are collected by vacuum filtration and recrystallized from water (34% yield). MS C$_7$H$_7$N$_3$O: m/z 150.0 (M+H)$^+$.

Step 1004b: Preparation of 3H-imidazo[4,5-b]pyridine-2-carboxylic acid

To a boiling solution of KMnO$_4$ (0.38 g, 2.4 mmol) in water (8 mL), a boiling solution of 3H-imidazo[4,5-b]pyridin-2-ylmethanol (0.20 g, 1.4 mmol) and Na$_2$CO$_3$ (0.19 g, 1.5 mmol) in water (6 mL) is added. The resulting mixture is heated at reflux for 4 hr. The hot mixture is filtered, the filtrate is cooled to rt, and the pH adjusted to 2 using conc. HCl. The resulting precipitate is collected by vacuum filtration to afford 3H-imidazo[4,5-b]pyridine-2-carboxylic acid in 100% yield: MS for C$_7$H$_5$N$_3$O$_2$: m/z 164 (M+H)$^+$.

Step 1004c: Coupling

To 3H-imidazo[4,5-b]pyridine-2-carboxylic acid (90 mg, 0.55 mmol) in DMF (4 mL) is added (R)-(+)-3-aminoquinuclidine dihydrochloride (0.11 g, 0.56 mmol), DIEA (0.25 g, 0.35 mL, 1.9 mmol) and HATU (0.21 g, 0.56 mmol). The mixture is stirred overnight at rt, diluted with CH$_2$Cl$_2$ (50 mL) and washed with 1 N NaOH (2×50 mL) followed by sat. aq. NaHCO$_3$ (50 mL). The material is purified by passage through acidic ion exchange resin. The free base is taken up in 3 M HCl/MeOH (10 mL) and stirred for 1.5 hr. Isopropanol and Et$_2$O are added and the solid is isolated by vacuum filtration to afford Example 1004 in 57% yield. MS for C$_{14}$H$_{17}$N$_5$O: 272 (M+H)$^+$.

EXAMPLE 1005

N-[(2S,3R)-2-methyl-1-azabicyclo[2.2.2]oct-3-yl]-1,3-benzothiazole-2-carboxamide hydrochloride

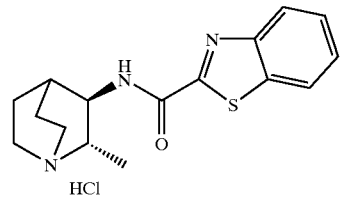

Coupling

A MeOH solution of ethyl 1,3-benzothiazole-2-carboxylate (0.48 g, 2.3 mmol) is added to a solution of NaOH (0.096 g, 2.4 mmol) dissolved in 7 mL MeOH. After 1 h, the solvent is removed. The solids are washed with ether and dried in vacuo to provide 0.43 g (92%) of the sodium salt. Sodium 1,3-benzothiazole-2-carboxylate (0.21 g, 1.05 mmol), HATU (0.46 g, 1.2 mmol) and (2S,3R)-2-methyl-1-azabicyclo[2.2.2]octan-3-amine dihydrochloride (0.22 g, 1.02 mmol) are suspended in 15 mL CH$_3$CN. DIEA (1.5 mL, 8.6 mmol) is added dropwise. After 24 h, 1N NaOH is added, and the mixture is extracted with CHCl$_3$. The combined organic layers are dried (MgSO$_4$), filtered and concentrated. The residue is purified by chromatography (Biotage 40S, 90:9.5:0.5 CHCl$_3$/MeOH/NH$_4$OH). The hydrochloride salt is prepared and recrystallized from MeOH/EtOAc to provide 0.173 g (50%) of the product. HRMS (FAB) calculated for C$_{16}$H$_{19}$N$_3$OS+H 302.1327, found 302.1330.

Materials and Methods for Identifying Binding Constants

Membrane Preparation. Male Sprague-Dawley rats (300–350 g) are sacrificed by decapitation and the brains (whole brain minus cerebellum) are dissected quickly, weighed and homogenized in 9 volumes/g wet weight of ice-cold 0.32M sucrose using a rotating pestle on setting 50 (10 up and down strokes). The homogenate is centrifuged at 1,000×g for 10 minutes at 4° C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at room temperature and diluted with Kreb's −20 mM Hepes buffer pH 7.0 (at room temperature) containing 4.16 mM NaHCO$_3$, 0.44 mM KH$_2$PO$_4$, 127 mM NaCl, 5.36 mM KCl, 1.26 mM CaCl$_2$, and 0.98 mM MgCl$_2$, so that 25–150 μg protein are added per test tube. Proteins are determined by the Bradford method (Bradford, M. M., Anal. Biochem., 72, 248–254, 1976) using bovine serum albumin as the standard.

Binding Assay. For saturation studies, 0.4 mL homogenate are added to test tubes containing buffer and various concentrations of radioligand, and are incubated in a final volume of 0.5 mL for 1 hr at 25° C. Nonspecific binding was determined in tissues incubated in parallel in the presence of 0.05 ml MLA for a final concentration of 1 μM MLA, added before the radioligand. In competition studies, drugs are added in increasing concentrations to the test tubes before addition of 0.05 ml [$^3$H]-MLA for a final concentration of 3.0 to 4.0 nM [$^3$H]-MLA. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis. In competition binding studies, the inhibition constant (Ki) was calculated from the concentration dependent inhibition of [$^3$H]-MLA binding obtained from non-linear regression fitting program according to the Cheng-Prusoff equation (Cheng, Y. C. and Prussoff, W. H., Biochem. Pharmacol., 22, pp. 3099–3108, 1973). Hill coefficients were obtained using non-linear regression (GraphPad Prism sigmoidal dose-response with variable slope).

The aforementioned examples have the provided Ki values:

| Example # | Ki (nM) |
|---|---|
| Example 3 | 32 |
| Example 4 | 305 |
| Example 5 | 30 |
| Example 6 | 110 |
| Example 7 | 24 |
| Example 11 | 92 |
| Example 1005 | 73 |

What is claimed:
1. A compound of the Formula I:

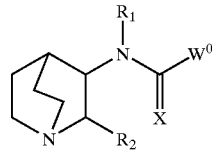

Formula I wherein W$^0$ is a bicyclic moiety and is

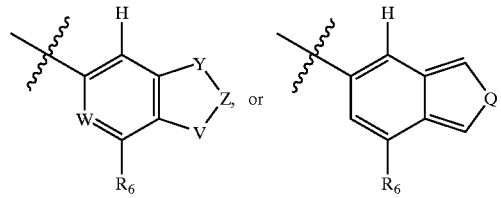

X is O, or S;

R$_1$ is H, alkyl, cycloalkyl, halogenated alkyl, substituted phenyl, or substituted naphthyl;

R$_2$ is H, alkyl, halogenated alkyl, substituted alkyl, cycloalkyl, or aryl;

R$_3$ is H, F, alkyl, halogenated alkyl, substituted alkyl, lactam heterocycloalkyl, phenoxy, substituted phenoxy, R$_7$, R$_9$, —N(R$_4$)-aryl, —O-substituted phenyl, —O-substituted naphthyl, —S-substituted phenyl, —S-substituted naphthyl, alkyl substituted on the ω carbon with naphthyl, or alkyl substituted on the ω carbon with substituted naphthyl;

W is C(H) where

V—Z—Y is selected from O—C(R$_3$)=N, O—C(R$_5$)(R$_3$)—N(R$_4$), O—C(R$_5$)(R$_3$)—S, O—N=C(R$_5$), O—C(R$_3$)(R$_8$)—O, S—C(R$_3$)=N, S—C(R$_5$)(R$_3$)—N(R$_4$), S—N=C(R$_5$), N=C(R$_3$)—O, N=C(R$_3$)—S, N=C(R$_3$)—N(R$_4$), N(R$_4$)—N=C(R$_5$), N(R$_4$)—C(R$_5$)(R$_3$)—O, N(R$_4$)—C(R$_5$)(R$_3$)—S, N(R$_4$)—C(R$_5$)(R$_3$)—N(R$_4$), C(R$_5$)$_2$—O—N(R$_4$), C(R$_5$)$_2$—N(R$_4$)—O, C(R$_5$)$_2$—N(R$_4$)—S, C(R$_5$)=N—O, C(R$_5$)=N—S, C(R$_5$)=N—N(R$_4$), C(R$_5$)$_2$—O—C(R$_5$)$_2$, C(R$_5$)$_2$—S—C(R$_5$)$_2$, C(R$_5$)$_2$—N(R$_4$)—C(R$_5$)$_2$, or C(R$_5$)(R$_{17}$)—C(R$_3$)(R$_{17}$)—C(R$_5$)(R$_{17}$);

Q is N(R$_{19}$), O, or S;

W is N where

V—Z—Y is selected from O—C(R$_3$)=N, O—C(R$_5$)(R$_3$)—N(R$_4$), O—C(R$_5$)(R$_3$)—S, O—N=C(R$_5$) O—C(R$_3$)(R$_5$)—O, S—C(R$_3$)=N, S—C(R$_5$)(R$_3$)—N(R$_4$), S—N=C(R$_5$), N=C(R$_3$)—O, N=C(R$_3$)—S, N=C(R$_3$)—N(R$_4$), N(R$_4$)—N=C(R$_5$), N(R$_4$)—C(R$_5$)(R$_3$)—O, N(R$_4$)—C(R$_5$)(R$_3$)—S, N(R$_4$)—C(R$_5$)(R$_3$)—N(R$_4$), C(R$_5$)$_2$—O—N(R$_4$), C(R$_5$)$_2$—N$_{(4)}$—O, C(R$_5$)$_2$—N(R$_4$)—S, C(R$_5$)=N—O, C(R$_5$)=N—S, C(R$_5$)=N—N(R$_4$), C(R$_5$)=C(R$_3$)—C(R$_3$)—C(R$_5$)$_2$, or C(R$_5$)$_2$—C(R$_3$)(R$_5$)—C(R$_5$)$_2$;

R$_4$ is H, or alkyl;

R$_5$ is H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)NH$_2$, —C(O)N(R$_{16}$)$_2$, —NHR$_1$, —NR$_1$COR$_{16}$, —N(R$_{10}$)$_2$, —SR$_1$, —C(O)R$_{16}$, —CO$_2$R$_1$, aryl, R$_7$, or R$_9$;

$R_6$ is H, F, Cl, Br, I, —CN, —CF$_3$, —OR$_{16}$, —SR$_{16}$, or —N(R$_{16}$)$_2$;

$R_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from R$_{20}$ and further having 0–3 substituents independently selected from F, Cl, Br, or I, or R$_7$ is 9-membered fused-ring moieties having a 6-membered ring fused to a 5-membered ring and having the formula

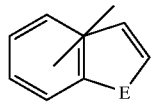

wherein E is O, S, or NR$_{19}$,

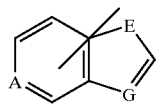

wherein E and G are independently selected from CR$_{18}$, O, S, N, or NR$_{19}$, and A is CR$_{18}$ or N, or

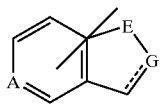

wherein E and G are independently selected from CR$_{18}$, O, S, N, or NR$_{19}$, and A is CR$_{18}$ or N, each 9-membered fused-ring moiety having 0–1 substituent selected from R$_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each R$_8$ is independently F, Br, Cl, I, alkyl, substituted alkyl, halogenated alkyl, alkenyl, substituted alkenyl, halogenated alkenyl, alkynyl, substituted alkynyl, halogenated alkynyl, —CN, —CF$_3$, —OR$_1$, —C(O)NH$_2$, —NHR$_1$, —SR$_1$, —CO$_2$R$_1$, aryl phenoxy, substituted phenoxy, heteroaryl, —N(R$_4$)-aryl, or —O-substituted aryl, R$_9$ is 6-membered heteroaromatic mono-cyclic moieties containing within the ring 1–3 heteroatoms selected from =N— and having 0–1 substituent selected from R$_{20}$ and 0–3 substituent(s) independently selected from F, Cl, Br, or I, or R$_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from R$_{20}$ and 0–3 substituent(s) independently selected from F, Cl, Br, or I and having a bond directly or indirectly attached to the core molecule where valency allows;

Each R$_{10}$ is independently H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, or substituted phenyl;

Each R$_{11}$ is independently H, alkyl, cycloalkyl, heterocyclo-alkyl, halogenated alkyl, halogenated cycloalkyl, or halogenated heterocycloalkyl;

$R_{13}$ is —OR$_{11}$, —SR$_{11}$, —NR$_{11}$R$_{11}$, —C(O)R$_{11}$, —C(O)NR$_{11}$R$_{11}$, —CN, —CF$_3$, —NR$_{11}$C(O)R$_{11}$, —S(O)$_2$NR$_{11}$R$_{11}$, —NR$_{11}$S(O)$_2$R$_{11}$, or —NO$_2$;

$R_{15}$ is aryl, R$_7$, or R$_9$;

$R_{16}$ is H, alkyl, substituted alkyl, cycloalkyl, halogenated alkyl, heterocycloalkyl, substituted heterocycloalkyl, substituted phenyl, or substituted naphthyl;

One of R$_{17}$ is H, alkyl, substituted alkyl, halogenated alkyl, alkenyl, substituted alkenyl, halogenated alkenyl, alkynyl, substituted alkynyl, halogenated alkynyl, —CN, F, Br, Cl, I, —OR$_1$, —C(O)NH$_2$, —NHR$_1$, —SR$_1$, —CO$_2$R$_1$, aryl, R$_7$, or R$_9$, and each of the other two R$_{17}$ is independently selected from alkyl, substituted alkyl, halogenated alkyl, alkenyl, substituted alkenyl, halogenated alkenyl, alkynyl, substituted alkynyl, halogenated alkynyl, —CN, F, Br, Cl, I, —OR$_1$, —C(O)NH$_2$, —NHR$_1$, —SR$_1$, —CO$_2$R$_1$, aryl, R$_7$, or R$_9$;

Each R$_{18}$ is independently selected from H, F, Cl, Br, I, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, or phenyl having 1 substituent selected from R$_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or R$_{13}$, cycloalkyl substituted with 1–4 substituent(s) independently selected from F, Cl, Br, I, or R$_{13}$, or heterocycloalkyl substituted with 1–4 substituent(s) independently selected from F, Cl, Br, I, or R$_{13}$;

Each R$_{22}$ is independently H, alkyl, substituted alkyl, cycloalkyl, halogenated alkyl, substituted cycloalkyl, heterocycloalkyl, or substituted heterocycloalkyl;

or pharmaceutically acceptable salt, or racemic mixture thereof.

2. The compound according to claim 1, wherein X is O.

3. The compound according to claim 2, wherein $R_1$ is H.

4. The compound according to claim 3, wherein $R_2$ is H.

5. The compound according to claim 4, wherein $W^0$ includes 1,3-benzoxazol-6-yl, 1,3-benzoxazol-5-yl, 1,3-benzothiazol-6-yl, indan-5-yl, 1,3-benzodioxol-5-yl, [1,3]oxazolo[5,4-c]pyridin-6-yl, 2-benzoisothiophen-5-yl, 1,3-benzothiazol-5-yl, 1,2-benzothiazol-6-yl, 1,2-benzisoxazol-5-yl, or 1H-indazol-6-yl, optionally substituted with F, Br, Cl, alkyl, halogenated alkyl, substituted alky, alkenyl, substituted alkenyl, halogenated alkenyl, alkynyl, substituted alkynyl, halogenated alkynyl, heterocycloalkyl, substituted heterocycloalkyl, lactam heterocycloalkyl, phenoxy, substituted phenoxy, —$CF_3$, —CN, —$NO_2$, —$OR_1$, —$OR_{22}$, —$NHR_1$, —$N(R_{10})_2$, —$N(R_{22})_2$, —$N(R_4)$-aryl, —$SR_1$, —$SR_{22}$, —$C(O)N(R_{16})_2$, or —$NR_1COR_{16}$.

6. The compound according to claim 3, wherein $R_2$ is alkyl, halogenated alkyl, substituted alkyl, cycloalkyl, or aryl.

7. The compound according to claim 6, wherein $W^0$ includes 1,3-benzoxazol-6-yl, 1,3-benzoxazol-5-yl, 1,3-benzothiazol-6-yl, indan-5-yl, 1,3-benzodioxol-5-yl, [1,3]oxazolo[5,4-c]pyridin-6-yl, 2-benzoisothiophen-5-yl, 1,3-benzothiazol-5-yl, 1,2-benzothiazol-6-yl, 1,2-benzisoxazol-5-yl, or 1H-indazol-6-yl, optionally substituted with F, Br, Cl, alkyl, halogenated alkyl, substituted alky, alkenyl, substituted alkenyl, halogenated alkenyl, alkynyl, substituted alkynyl, halogenated alkynyl, heterocycloalkyl, substituted heterocycloalkyl, lactam heterocycloalkyl, phenoxy, substituted phenoxy, —$CF_3$, —CN, —$NO_2$, —$OR_1$, —$OR_{22}$, —$NHR_1$, —$N(R_{10})_2$, —$N(R_{22})_2$, —$N(R_4)$-aryl, —$SR_1$, —$SR_{22}$, —$C(O)N(R_{16})_2$, or —$NR_1COR_{16}$.

8. The compound according to claim 7, wherein $R_2$ is alkyl, halogenated alkyl, or substituted alkyl.

9. The compound according to claim 8, wherein $R_2$ is alkyl.

10. The compound according to claim 9, wherein $R_2$ is $CH_3$.

11. The compound according to claim 1, wherein the compound of Formula I has the R stereochemistry at C3 of quinuclidine.

12. The compound according to claim 11, wherein the compound of Formula I includes N-((3R)-1-azabicyclo[2.2.2]oct-3-yl)-1,3-benzoxazole-6-carboxamide; N-((3R)1-azabicyclo[2.2.2]oct-3-yl)-2-methyl-1,3-benzoxazole-6-carboxamide; N-((3R)1-azabicyclo[2.2.2]oct-3-yl)-1,3-benzoxazole-5-carboxamide; N-((3R)1-azabicyclo[2.2.2]oct-3-yl)-2-methyl-1,3-benzoxazole-5-carboxamide; N-((3R)1-azabicyclo[2.2.2]oct-3-yl)-1,3-benzothiazole-6-carboxamide; N-((3R)1-azabicyclo[2.2.2]oct-3-yl)indane-5-carboxamide; N-[(3R)-1-azabicyclo[2.2.2]oct-3-yl[]1,3]oxazolo[5,4-c]pyridine-6-carboxamide; N-[(3R)-1-azabicyclo[2.2.2]oct-3-yl]-2-benzoisothiophene-5-carboxamide; N-[(3R)-1-azabicyclo[2.2.2]oct-3-yl]-1,3-benzothiazole-5-carboxamide; N-[(3-R)-1-azabicyclo[2.2.2]oct-3-yl]-3-methyl-1,2-benzisoxazole-6-carboxamide; N-[(3R)-1-azabicyclo[2.2.2]oct-3-yl]-3-methyl-1,2-benzisoxazole-5-carboxamide; N-[(3R)-1-azabicyclo[2.2.2]oct-3-yl]-1H-indazole-6-carboxamide; N-((2S,3R)-2-methyl-1-azabicyclo[2.2.2]oct-3-yl)-1,3-benzoxazole-6-carboxamide; N-((2S,3R)-2-methyl-1-azabicyclo[2.2.2]oct-3-yl)-2-methyl-1,3-benzoxazole-6-carboxamide; N-((2S,3R)-2-methyl-1-azabicyclo[2.2.2]oct-3-yl)-1,3-benzoxazole-5-carboxamide; N-((2S,3R)-2-methyl-1-azabicyclo[2.2.2]oct-3-yl)-2-methyl-1,3-benzoxazole-5-carboxamide; N-((2S,3R)-2-methyl-1-azabicyclo[2.2.2]oct-3-yl)-1,3-benzothiazole-6-carboxamide; N-((2S,3R)-2-methyl-1-azabicyclo[2.2.2]oct-3-yl)indane-5-carboxamide; N-((2S,3R)-2-methyl-1-azabicyclo[2.2.2]oct-3-yl)-1,3-benzodioxole-5-carboxamide; N-[(2S,3R)-2-methyl-1-azabicyclo[2.2.2]oct-3-yl][1,3]oxazolo[5,4-c]pyridine-6-carboxamide; N-[(2S,3R)-2-methyl-1-azabicyclo[2.2.2]oct-3-yl]-2-benzoisothiophene-5-carboxamide; N-[(2S,3R)-2-methyl-1-azabicyclo[2.2.2]oct-3-yl]-1,3-benzothiazole-5-carboxamide; N-[(2S,3R)-2-methyl-1-azabicyclo[2.2.2]oct-3-yl]-3-methyl-1,2-benzisoxazole-6-carboxamide; N-[(2S,3R)-2-methyl-1-azabicyclo[2.2.2]oct-3-yl]-3-methyl-1,2-benzisoxazole-5-carboxamide; N-[(2S,3R)-2-methyl-1-azabicyclo[2.2.2]oct-3-yl]-1H-indazole-6-carboxamide; or a pharmaceutically acceptable salt thereof.

13. The compound according to claim 11, wherein the compound of Formula I includes N-[(3R)-1-azabicyclo[2.2.2]oct-3-yl]-1H-indazole-5-carboxamide; N-[(3R)-1-azabicyclo[2.2.2]oct-3-yl]-3-methyl-1H-indazole-6-carboxamide; N-[(3R)-1-azabicyclo[2.2.2]oct-3-yl]-3-methyl-1H-indazole-5-carboxamide; N-[(3R)-1-azabicyclo[2.2.2]oct-3-yl]-3-ethyl-1H-indazole-6-carboxamide; N-[(3R)-1-azabicyclo[2.2.2]oct-3-yl]-3-ethyl-1H-indazole-5-carboxamide; N-[(3R)-1-azabicyclo[2.2.2]oct-3-yl]-1,2-benzisothiazole-6-carboxamide; N-[(3R)-1-azabicyclo[2.2.2]oct-3-yl]-1,2-benzisothiazole-5-carboxamide; N-[(3R)-1-azabicyclo[2.2.2]oct-3-yl]-3-ethyl-1,2-benzisothiazole-6-carboxamide; N-[(3R )-1-azabicyclo[2.2.2]oct-3-yl]-3-ethyl-1,2-benzisothiazole-5-carboxamide; N-[(3R )-1-azabicyclo[2.2.2]oct-3-yl]-3-methyl-1,2-benzisothiazole-6-carboxamide; N-[(3R)-1-azabicyclo[2.2.2]oct-3-yl]-3-methyl-1,2-benzisothiazole-5-carboxamide; N-[(3R)-1-azabicyclo[2.2.2]oct-3-yl]-2-cyclopropyl-1,3-benzoxazole-6-carboxamide; N-[(3R)-1-azabicyclo[2.2.2]oct-3-yl]-2-cyclopropyl-1,3-benzoxazole-5-carboxamide; N-[(3R)-1-azabicyclo[2.2.2]oct-3-yl]-2-cyclopropyl-1,3-benzothiazole-6-carboxamide; N-[(3R)-1-azabicyclo[2.2.2]oct-3-yl]-2-cyclopropyl-1,3-benzothiazole-5-carboxamide; N-[(3R)-1-azabicyclo[2.2.2]oct-3-yl]-2-methyl-1,3-benzothiazole-6-carboxamide; N-[(3R)-1-azabicyclo[2.2.2]oct-3-yl]-2-methyl-1,3-benzothiazole-5-carboxamide; N-[(3R)-1-azabicyclo[2.2.2]oct-3-yl]-2-ethyl-1,3-benzothiazole-6-carboxamide; N-[(3R)-1-azabicyclo[2.2.2]oct-3-yl]-2-ethyl-1,3-benzothiazole-5-carboxamide; N-[(3R)-1-azabicyclo[2.2.2]oct-3-yl]-2-methyl-1,3-benzodioxole-5-carboxamide; N-[(3R)-1-azabicyclo[2.2.2]oct-3-yl]-2-ethyl-1,3-benzodioxole-5-carboxamide; N-[(3R)-1-azabicyclo[2.2.2]oct-3-yl]-2,2-dimethyl-1,3-benzodioxole-5-carboxamide; N-[(3R)-1-azabicyclo[2.2.2]oct-3-yl]-2-benzofuran-5-carboxamide; N-[(3R)-1-azabicyclo[2.2.2]oct-3-yl]-2H-isoindole-5-carboxamide; N-[(3R)-1-azabicyclo[2.2.2]oct-3-yl]-1H-benzimidazole-5-carboxamide; N-[(3R)-1-azabicyclo[2.2.2]oct-3-yl][1,3]thiazolo[5,4-c]pyridine-6-carboxamide; N-[(3R)-1-azabicyclo[2.2.2]oct-3-yl][1,3]thiazolo[4,5-c]pyridine-6-carboxamide; N-[(3R)-1-azabicyclo[2.2.2]oct-3-yl][1,3]dioxolo[4,5-c]pyridine-6-carboxamide; N-[(3R)-1-azabicyclo[2.2.2]oct-3-yl][1,3]oxazolo[4,5-c]pyridine-6-carboxamide; N-[(3R)-1-azabicyclo[2.2.2]oct-3-yl]-1H]imidazo[4,5-c]pyridine-6-carboxamide;

N-[(2S,3R)-2-methyl-1-azabicyclo[2.2.2]oct-3-yl]-1H-indazole-6-carboxamide; N-[(2S,3R)-2-methyl-1-azabicyclo[2.2.2]oct-3-yl]-1H-indazole-5-carboxamide; N-[(2S,3R)-2-methyl-1-azabicyclo[2.2.2]oct-3-yl]-3-methyl-1H-indazole-6-carboxamide; N-[(2S,3R)-2-methyl-1-azabicyclo[2.2.2]oct-3-yl]-3-methyl-1H-indazole-5-carboxamide; N-[(2S,3R)-2-methyl-1-azabicyclo[2.2.2]oct-3-yl]-3-ethyl-1H- indazole-6-carboxamide ; N-[(2S,3R)-2-methyl-1-azabicyclo[2.2.2]oct-3-yl]-3-ethyl-1H-indazole-5-carboxamide; N-[(2S,3R)-2-methyl-1-azabicyclo[2.2.2]oct-3-yl]-1,2-benzisothiazole-6-carboxamide; N-[(2S,3R)-2-methyl-1-azabicyclo[2.2.2]oct-3-yl]-1,2-benzisothiazole-5-carboxamide; N-[(2S,3R)-2-methyl-1-azabicyclo[2.2.2]oct-3-yl]-3-ethyl-1,2-benzisothiazole-6-carboxamide; N-[(2S,3R)-2-methyl-1-azabicyclo[2.2.2]oct-3-yl]-3-ethyl-1,2-benzisothiazole-5-carboxamide; N-[(2S,3R)-2-methyl-1-azabicyclo[2.2.2]oct-3-yl]-3-methyl-1,2-benzisothiazole-6-carboxamide; N-[(2S,3R)-2-methyl-1-azabicyclo[2.2.2]oct-3-yl]-3-methyl-1,2-benzisothiazole-5-carboxamide; N-[(2S,3R)-2-methyl-1-azabicyclo[2.2.2]oct-3-yl]-2-cyclopropyl-1,3-benzoxazole-6-carboxamide; N-[(2S,3R)-2-methyl-1-azabicyclo[2.2.2]oct-3-yl]-2-cyclopropyl-1,3-benzoxazole-5-carboxamide; N-[(2S,3R)-2-methyl-1-azabicyclo[2.2.2]oct-3-yl]-2-cyclopropyl-1,3-benzothiazole-6-carboxamide; N-[(2S,3R)-2-methyl-1-azabicyclo[2.2.2]oct-3-yl]-2-cyclopropyl-1,3-benzothiazole-5-carboxamide; N-[(2S,3R)-2-methyl-1-azabicyclo[2.2.2]oct-3-yl]-2-methyl-1,3-benzothiazole-6-carboxamide; N-[(2S,3R)-2-methyl-1-azabicyclo[2.2.2]oct-3-yl]-2-methyl-1,3-benzothiazole-5-carboxamide; N-[(2S,3R)-2-methyl-1-azabicyclo[2.2.2]oct-3-yl]-2-ethyl-1,3-benzothiazole-6-carboxamide; N-[(2S,3R)-2-methyl-1-azabicyclo[2.2.2]oct-3-yl]-2-ethyl-1,3-benzothiazole-5-carboxamide; N-[(2S,3R)-2-methyl-1-azabicyclo[2.2.2]oct-3-yl]-2-methyl-1,3-benzodioxole-5-carboxamide; N-[(2S,3R)-2-methyl-1-azabicyclo[2.2.2]oct-3-yl]-2-ethyl-1,3-benzodioxole-5-carboxamide; N-[(2S,3R)-2-methyl-1-azabicyclo[2.2.2]oct-3-yl]-2,2-dimethyl-1,3-benzodioxole-5-carboxamide; N-[(2S,3R)-2-methyl-1-azabicyclo[2.2.2]oct-3-yl]-2-benzofuran-5-carboxamide; N-[(2S,3R)-2-methyl-1-azabicyclo[2.2.2]oct-3-yl]-2H-isoindole-5-carboxamide; N-[(2S,3R)-2-methyl-1-azabicyclo[2.2.2]oct-3-yl]-1H-benzimidazole-5-carboxamide; N-[(2S,3R)-2-methyl-1-azabicyclo[2.2.2]oct-3-yl][1,3]thiazolo[5,4-c]pyridine-6-carboxamide; N-[(2S,3R)-2-methyl-1-azabicyclo[2.2.2]oct-3-yl][1,3]thiazolo[4,5-c]pyridine-6-carboxamide; N-[(2S,3R)-2-methyl-1-azabicyclo[2.2.2]oct-3-yl][1,3]dioxolo[4,5-c]pyridine-6-carboxamide; N-[(2S,3R)-2-methyl-1-azabicyclo[2.2.2]oct-3-yl][1,3]oxazolo[4,5-c]pyridine-6-carboxamide; N-[(2S,3R)-2-methyl-1-azabicyclo[2.2.2]oct-3-yl]-1H-imidazo[4,5-c]pyridine-6-carboxamide; or a pharmaceutically acceptable salt thereof.

14. The compound according to claim 1, wherein the compound of Formula I has the S stereochemistry at C3 of quinuclidine.

15. The compound according to claim 14, wherein the compound of Formula I includes N-((3S)-1-azabicyclo[2.2.2]oct-3-yl)-1,3-benzoxazole-6-carboxamide; N-((3S)1-azabicyclo[2.2.2]oct-3-yl)-2-methyl-1,3-benzoxazole-6-carboxamide; N-((3S)1-azabicyclo[2.2.2]oct-3-yl)-1,3-benzoxazole-5-carboxamide; N-((3S)1-azabicyclo[2.2.2]oct-3-yl)-2-methyl-1,3-benzoxazole-5-carboxamide; N-((3S)1-azabicyclo[2.2.2]oct-3-yl)-1,3-benzothiazole-6-carboxamide; N-((3S)1-azabicyclo[2.2.2]oct-3-yl)indane-5-carboxamide; N-((3S)-1-azabicyclo[2.2.2]oct-3-yl)-1,3-benzodioxole-5-carboxamide; N-[(3S)-1-azabicyclo[2.2.2]oct-3-yl][1,3]oxazolo[5,4-c]pyridine-6-carboxamide; N-[(3S)-1-azabicyclo[2.2.2]oct-3-yl]-2-benzoisothiophene-5-carboxamide; N-[(3S)-1-azabicyclo[2.2.2]oct-3-yl]-1,3-benzothiazole-5-carboxamide; N-[(3S)-1-azabicyclo[2.2.2]oct-3-yl]-3-methyl-1,2-benzisoxazole-6-carboxamide; N-[(3S)-1-azabicyclo[2.2.2]oct-3-yl]-3-methyl-1,2-benzisoxazole-5-carboxamide; N-[(3S)-1-azabicyclo[2.2.2]oct-3-yl]-1H-indazole-6-carboxamide; or a pharmaceutically acceptable salt thereof.

16. A pharmaceutical composition comprising a compound according to claim 1.

17. The pharmaceutical composition according to claim 16, wherein said pharmaceutical composition is to be administered rectally, topically, orally, sublingually, or parenterally.

18. The pharmaceutical composition according to claim 17, wherein said compound is administered in an amount of from about 0.001 to about 100 mg/kg of body weight of said mammal per day.

19. The pharmaceutical composition according to claim 17, wherein said compound is administered in an amount of from about 0.1 to about 50 mg/kg of body weight of said mammal per day.

20. A pharmaceutical composition comprising a compound according to claim 1 and an anti-psychotic agent.

21. The pharmaceutical composition according to claim 20, wherein said compound and said agent are to be independently administered rectally, topically, orally, sublingually, or parenterally for a therapeutically effective interval.

22. The pharmaceutical composition according to claim 21, wherein said compound is administered in an amount of from about 0.001 to about 100 mg/kg of body weight of said mammal per day.

23. The pharmaceutical composition according to claim 21, wherein said compound is administered in an amount of from about 0.1 to about 50 mg/kg of body weight of said mammal per day.

24. A method for treating a disease or condition in a mammal in need thereof, wherein the disease or condition is cognitive and attention deficit symptoms of Alzheimer's, neurodegeneration associated with diseases such as Alzheimer's disease, pre-senile dementia (mild cognitive impairment), or senile dementia comprising administering to the mammal a therapeutically effective amount of a compound according to Formula I:

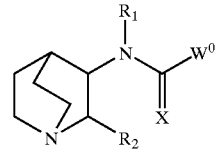

Formula I wherein $W^0$ is a bicyclic moiety and is

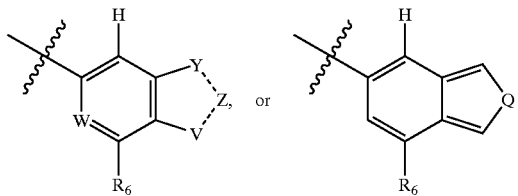

X is O, or S;

$R_1$ is H, alkyl, cycloalkyl, halogenated alkyl, substituted phenyl, or substituted naphthyl;

$R_2$ is H, alkyl, halogenated alkyl, substituted alkyl, cycloalkyl, or aryl;

$R_3$ is H, F, alkyl, halogenated alkyl, substituted alkyl, lactam heterocycloalkyl, phenoxy, substituted phenoxy, $R_7$, $R_9$, —N($R_4$)-aryl, —O-substituted phenyl, —O-substituted naphthyl, —S-substituted phenyl, —S-substituted naphthyl, alkyl substituted on the ω carbon with naphthyl, or alkyl substituted on the ω carbon with substituted naphthyl;

W is C(H) where

V—Z—Y is selected from O—C($R_3$)=N, O—C($R_5$)($R_3$)—N($R_4$), O—C($R_5$)($R_3$)—S, O—N=C($R_5$), O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)$_2$—N—N($R_4$), C($R_5$)$_2$—O—C($R_5$)$_2$, C($R_5$)$_2$—S—C($R_5$)$_2$, C($R_5$)$_2$—N($R_4$)—C($R_5$)$_2$, or C($R_5$)$_2$—C($R_3$)($R_5$)—C($R_5$)$_2$;

Q is N($R_{19}$), O, or S;

W is N where

V—Z—Y is selected from O—C($R_3$)=N, O—C($R_5$)($R_3$)—N($R_4$), O—C($R_5$)($R_3$)—S, O—N=C($R_5$) O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)$_2$=N—N($R_4$), C($R_5$)=C($R_3$)—C($R_5$)$_2$, or C($R_5$)$_2$—C($R_3$)($R_5$)—C($R_5$)$_2$;

$R_4$ is H, or alkyl;

$R_5$ is H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)NH$_2$, —C(O)N(R$_{16}$)$_2$, —NHR$_1$, —NR$_1$COR$_{16}$, —N(R$_{10}$)$_2$, —SR$_1$, —C(O)R$_{16}$, —CO$_2$R$_1$, aryl, $R_7$, or $R_9$;

$R_6$ is H, F, Cl, Br, I, —CN, —CF$_3$, —OR$_{16}$, —SR$_{16}$, or —N(R$_{16}$)$_2$;

$R_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from R$_{20}$ and further having 0–3 substituents independently selected from F, Cl, Br, or I, or $R_7$ is 9-membered fused-ring moieties having a 6-membered ring fused to a 5-membered ring and having the formula

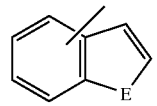

wherein E is O, S, or NR$_{19}$,

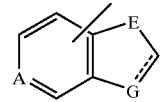

wherein E and G are independently selected from CR$_{18}$, O, S, N, or NR$_{19}$, and A is CR$_{18}$ or N, or

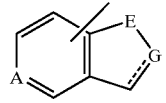

wherein E and G are independently selected from CR$_{18}$, O, S, N, or NR$_{19}$, and A is CR$_{18}$ or N, each 9-membered fused-ring moiety having 0–1 substituent selected from R$_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each $R_8$ is independently F, Br, Cl, I, alkyl, substituted alkyl, halogenated alkyl, alkenyl, substituted alkenyl, halogenated alkenyl, alkynyl, substituted alkynyl, halogenated alkynyl, —CN, —CF$_3$, —OR$_1$, —C(O)NH$_2$, —NHR$_1$, —SR$_1$, —CO$_2$R$_1$, aryl, phenoxy, substituted phenoxy, heteroaryl, —N(R$_4$)-aryl, or —O-substituted aryl.

$R_9$ is 6-membered heteroaromatic mono-cyclic moieties containing within the ring 1–3 heteroatoms selected from =N— and having 0–1 substituent selected from R$_{20}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from R$_{20}$ and 0–3 substituent(s) independently selected from F, Cl, Br, or I and having a bond directly or indirectly attached to the core molecule where valency allows;

Each $R_{10}$ is independently H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, or substituted phenyl;

Each $R_{11}$ is independently H, alkyl, cycloalkyl, heterocyclo-alkyl, halogenated alkyl, halogenated cycloalkyl, or halogenated heterocycloalkyl;

$R_{13}$ is —OR$_{11}$, —SR$_{11}$, —NR$_{11}$R$_{11}$, —C(O)R$_{11}$, —C(O)NR$_{11}$R$_{11}$, —CN, —CF$_3$, —NR$_{11}$C(O)R$_{11}$, —S(O)$_2$NR$_{11}$R$_{11}$, —NR$_{11}$S(O)$_2$R$_{11}$, or —NO$_2$;

$R_{15}$ is aryl, $R_7$, or $R_9$;

$R_{16}$ is H, alkyl, substituted alkyl, cycloalkyl, halogenated alkyl, heterocycloalkyl, substituted heterocycloalkyl, substituted phenyl, or substituted naphthyl;

Each $R_{18}$ is independently selected from H, F, Cl, Br, I, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

R$_{19}$ is H, alkyl, halogenated alkyl, substituted alkyl, cycloalkyl, halogenated cycloalkyl, substituted cycloalkyl, phenyl, or phenyl having 1 substituent selected from R$_{20}$ and further having 0–3 substituents independently selected from F, Cl, Br, or I;

R$_{20}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or R$_{13}$, cycloalkyl substituted with 1–4 substituent(s) independently selected from F, Cl, Br, I, or R$_{13}$, or heterocycloalkyl substituted with 1–4 substituent(s) independently selected from F, Cl, Br, I, or R$_{13}$;

Each R$_{22}$ is independently H, alkyl, substituted alkyl, cycloalkyl, halogenated alkyl, substituted cycloalkyl, heterocycloalkyl, or substituted heterocycloalkyl;

or pharmaceutically acceptable salt, or racemic mixture thereof.

25. The method according to claim 24, wherein X is O.

26. The method according to claim 25, wherein R$_1$ is H.

27. The method according to claim 26, wherein R$_2$ is H.

28. The method according to claim 27, wherein W$^0$ includes 1,3-benzoxazol-6-yl, 1,3-benzoxazol-5-yl, 1,3-benzothiazol-6-yl, indan-5-yl, 1,3-benzodioxol-5-yl, [1,3]oxazolo[5,4-c]pyridin-6-yl, 2-benzoisothiophen-5-yl, 1,3-benzothiazol-5-yl, 1,2-benzothiazol-6-yl, 1,2-benzisoxazol-5-yl, or 1H-indazol-6-yl, optionally substituted with F, Br, Cl, alkyl, halogenated alkyl, substituted alky, alkenyl, substituted alkenyl, halogenated alkenyl, alkynyl, substituted alkynyl, halogenated alkynyl, heterocycloalkyl, substituted heterocycloalkyl, lactam heterocycloalkyl, phenoxy, substituted phenoxy, —CF$_3$, —CN, —NO$_2$, —OR$_1$, —OR$_{22}$, —NHR$_1$, —N(R$_{10}$)$_2$, —N(R$_{22}$)$_2$, —N(R$_4$)-aryl, —SR$_1$, SR$_{22}$, —C(O)N(R$_{16}$)$_2$, or —NR$_1$COR$_{16}$.

29. The method according to claim 26, wherein R$_2$ is alkyl, halogenated alkyl, substituted alkyl, cycloalkyl, or aryl, and wherein W$^0$ includes 1,3-benzoxazol-6-yl, 1,3-benzoxazol-5-yl, 1,3-benzothiazol-6-yl, indan-5-yl, 1,3-benzodioxol-5-yl, [(1,3]oxazolo[5,4-c]pyridin-6-yl, 2-benzoisothiophen-5-yl, 1,3-benzothiazol-5-yl, 1,2-benzothiazol-6-yl, 1,2-benzisoxazol-5-yl, or 1H-indazol-6-yl, optionally substituted with F, Br, Cl, alkyl, halogenated alkyl, substituted alky, alkenyl, substituted alkenyl, halogenated alkenyl, alkynyl, substituted alkynyl, halogenated alkynyl, heterocycloalkyl, substituted heterocycloalkyl, lactam heterocycloalkyl, phenoxy, substituted phenoxy, —CF$_3$, —CN, —NO$_2$, —OR$_1$, —OR$_{22}$, —NHR$_1$, —N(R$_{10}$)$_2$, —N(R$_{22}$)$_2$, —N(R$_4$)-aryl, —SR$_1$, —SR$_{22}$, —C(O)N(R$_{16}$)$_2$, or —NR$_1$COR$_{16}$.

30. The method according to claim 29, wherein R$_2$ is alkyl, halogenated alkyl, substituted alkyl.

31. The method according to claim 24, wherein the compound of Formula I has the R stereochemistry at C3 of quinuclidine.

32. The method according to claim 31, wherein the compound of Formula I includes N-((3R)-1-azabicyclo[2.2.2]oct-3-yl)-1,3-benzoxazole-6-carboxamide; N-((3R)1-azabicyclo[2.2.2]oct-3-yl)-2-methyl-1,3-benzoxazole-6-carboxamide; N-((3R)1-azabicyclo[2.2.2]oct-3-yl)-1,3-benzoxazole-5-carboxamide; N-((3R)1-azabicyclo[2.2.2]oct-3-yl)-2-methyl-1,3-benzoxazole-5-carboxamide; N-((3R)1-azabicyclo[2.2.2]oct-3-yl)-1,3-benzothiazole-6-carboxamide; N-((3R)1-azabicyclo[2.2.2]oct-3-yl)indane-5-carboxamide; N-((3R)-1-azabicyclo[2.2.2]oct-3-yl)-1,3-benzodioxole-5-carboxamide; N-[(3R)-1-azabicyclo[2.2.2]oct-3-yl][1,3]oxazolo[5,4-c]pyridine-6-carboxamide; N-[(3R)-1-azabicyclo[2.2.2]oct-3-yl]-2-benzoisothiophene-5-carboxamide; N-[(3R)-1-azabicyclo[2.2.2]oct-3-yl]-1,3-benzothiazole-5-carboxamide; N-[(3R)-1-azabicyclo[2.2.2]oct-3-yl]-3-methyl-1,2-benzisoxazole-6-carboxamide; N-[(3R)-1-azabicyclo[2.2.2]oct-3-yl]-3-methyl-1,2-benzisoxazole-5-carboxamide; N-[(3R)-1-azabicyclo[2.2.2]oct-3-yl]-1H-indazole-6-carboxamide; N-((2S,3R)-2-methyl-1-azabicyclo[2.2.2]oct-3-yl)-1,3-benzoxazole-6-carboxamide; N-((2S,3R)-2-methyl-1-azabicyclo[2.2.2]oct-3-yl)-2-methyl-1,3-benzoxazole-6-carboxamide; N-((2S,3R)-2-methyl-1-azabicyclo[2.2.2]oct-3-yl)-1,3-benzoxazole-5-carboxamide; N-((2S,3R)-2-methyl-1-azabicyclo[2.2.2]oct-3-yl)-2-methyl-1,3-benzoxazole-5-carboxamide; N-((2S,3R)-2-methyl-1-azabicyclo[2.2.2]oct-3-yl)-1,3-benzothiazole-6-carboxamide; N-((2S,3R)-2-methyl-1-azabicyclo[2.2.2]oct-3-yl)indane-5-carboxamide; N-((2S,3R)-2-methyl-1-azabicyclo[2.2.2]oct-3-yl)-1,3-benzodioxole-5-carboxamide; N-[(2S,3R)-2-methyl-1-azabicyclo[2.2.2]oct-3-yl][1,3]oxazolo[5,4-c]pyridine-6-carboxamide; N-[(2S,3R)-2-methyl-1-azabicyclo[2.2.2]oct-3-yl]-2-benzoisothiophene-5-carboxamide; N-[(2S,3R)-2-methyl-1-azabicyclo[2.2.2]oct-3-yl]-1,3-benzothiazole-5-carboxamide; N-[(2S,3R)-2-methyl-1-azabicyclo[2.2.2]oct-3-yl]-3-methyl-1,2-benzisoxazole-6-carboxamide; N-[(2S,3R)-2-methyl-1-azabicyclo[2.2.2]oct-3-yl]-3-methyl-1,2-benzisoxazole-5-carboxamide; N-[(2S,3R)-2-methyl-1-azabicyclo[2.2.2]oct-3-yl]-1H-indazole-6-carboxamide; or a pharmaceutically acceptable salt thereof.

33. The method according to claim 31, wherein the compound of Formula I includes N-[(3R)-1-azabicyclo[2.2.2]oct-3-yl]-1H-indazole-5-carboxamide; N-[(3R)-1-azabicyclo[2.2.2]oct-3-yl]-3-methyl-1H-indazole-6-carboxamide; N-[(3R)-1-azabicyclo[2.2.2]oct-3-yl]-3-methyl-1H-indazole-5-carboxamide; N-[(3R)-1-azabicyclo[2.2.2]oct-3-yl]-3-ethyl-1H-indazole-6-carboxamide; N-[(3R)-1-azabicyclo[2.2.2]oct-3-yl]-3-ethyl-1H-indazole-5-carboxamide; N-[(3R)-1-azabicyclo[2.2.2]oct-3-yl]-1,2-benzisothiazole-6-carboxamide; N-[(3R)-1-azabicyclo[2.2.2]oct-3-yl]-1,2-benzisothiazole-5-carboxamide; N-[(3R)-1-azabicyclo[2.2.2]oct-3-yl]-3-ethyl-1,2-benzisothiazole-6-carboxamide; N-[(3R)-1-azabicyclo[2.2.2]oct-3-yl]-3-ethyl-1,2-benzisothiazole-5-carboxamide; N-[(3R)-1-azabicyclo[2.2.2]oct-3-yl]-3-methyl-1,2-benzisothiazole-6-carboxamide; N-[(3R)-1-azabicyclo[2.2.2]oct-3-yl]-3-methyl-1,2-benzisothiazole-5-carboxamide; N-[(3R)-1-azabicyclo[2.2.2]oct-3-yl]-2-cyclopropyl-1,3-benzoxazole-6-carboxamide; N-[(3R)-1-azabicyclo[2.2.2]oct-3-yl]-2-cyclopropyl-1,3-benzoxazole-5-carboxamide; N-[(3R)-1-azabicyclo[2.2.2]oct-3-yl]-2-cyclopropyl-1,3-benzothiazole-6-carboxamide; N-[(3R)-1- azabicyclo[2.2.2]oct-3-yl]-2-cyclopropyl-1,3-benzothiazole-5-carboxamide; N-[(3R)-1-azabicyclo[2.2.2]oct-3-yl]-2-methyl-1,3-benzothiazole-6-carboxamide; N-[(3R)-1-azabicyclo[2.2.2]oct-3-yl]-2-methyl-1,3-benzothiazole-5-carboxamide; N-[(3R)-1-azabicyclo[2.2.2]oct-3-yl]-2-ethyl-1,3-benzothiazole-6-carboxamide; N-[(3R)-1-azabicyclo[2.2.2]oct-3-yl]-2-ethyl-1,3-benzothiazole-5-carboxamide; N-[(3R)-1-azabicyclo[2.2.2]oct-3-yl]-2-methyl-1,3-benzodioxole-5-carboxamide; N-[(3R)-1-azabicyclo[2.2.2]oct-3-yl]-2-ethyl-1,3-benzodioxole-5-carboxamide; N-[(3R)-1-azabicyclo[2.2.2]oct-3-yl]-2,2-dimethyl-1,3-benzodioxole-5-carboxamide; N-[(3R)-1-azabicyclo[2.2.2]oct-3-yl]-2-benzofuran-5-carboxamide; N-[(3R)-1-azabicyclo[2.2.2]oct-3-yl]-2H-isoindole-5-carboxamide; N-[(3R)-1-azabicyclo[2.2.2]oct-3-yl]-1H-benzimidazole-5-carboxamide; N-[(3R)-1-azabicyclo[2.2.2]oct-3-yl][1,3]thiazolo[5,4-c]pyridine-6-carboxamide; N-[(3R)-1-azabicyclo[2.2.2]oct-3-yl][1,3]thiazolo[4,5-c]pyridine-6-carboxamide; N-[(3R)-1-azabicyclo[2.2.2]oct-3-yl][1,3]dioxolo[4,5-c]pyridine-6-carboxamide; N-[(3R)-1-azabicyclo[2.2.2]oct-3-yl][1,3]oxazolo[4,5-c]pyridine-6-carboxamide; N-[(3R)-1-azabicyclo[2.2.2]oct-3-yl]-1H-imidazo[4,5-c]pyridine-6-carboxamide;

N-[(2S,3R)-2-methyl-1-azabicyclo[2.2.2]oct-3-yl]-1H-indazole-6-carboxamide; N-[(2S,3R)-2-methyl-1-azabicyclo[2.2.2]oct-3-yl]-1H-indazole-5-carboxamide; N-[(2S,3R)-2-methyl-1-azabicyclo[2.2.2]oct-3-yl]-3-methyl-1H-indazole-6-carboxamide; N-[(2S,3R)-2-methyl-1-azabicyclo[2.2.2]oct-3-yl]-3-methyl-1H-indazole-5-carboxamide; N-[(2S,3R)-2-methyl-1-azabicyclo[2.2.2]oct-3-yl]-3-ethyl-1H-indazole-6-carboxamide; N-[(2S,3R)-2-methyl-1-azabicyclo[2.2.2]oct-3-yl]-3-ethyl-1H-indazole-5-carboxamide; N-[(2S,3R)-2-methyl-1-azabicyclo[2.2.2]oct-3-yl]-1,2-benzisothiazole-6-carboxamide; N-[(2S,3R)-2-methyl-1-azabicyclo[2.2.2]oct-3-yl]-1,2-benzisothiazole-5-carboxamide; N-[(2S,3R)-2-methyl-1-azabicyclo[2.2.2]oct-3-yl]-3-ethyl-1,2-benzisothiazole-6-carboxamide; N-[(2S,3R)-2-methyl-1-azabicyclo[2.2.2]oct-3-yl]-3-ethyl-1,2-benzisothiazole-5-carboxamide; N-[(2S,3R)-2-methyl-1-azabicyclo[2.2.2]oct-3-yl]-3-methyl-1,2-benzisothiazole-6-carboxamide; N-[(2S,3R)-2-methyl-1-azabicyclo[2.2.2]oct-3-yl]-3-methyl-1,2-benzisothiazole-5-carboxamide; N-[(2S,3R)-2-methyl-1-azabicyclo[2.2.2]oct-3-yl]-2-cyclopropyl-1,3-benzoxazole-6-carboxamide; N-[(2S,3R)-2-methyl-1-azabicyclo[2.2.2]oct-3-yl]-2-cyclopropyl-1,3-benzoxazole-5-carboxamide; N-[(2S,3R)-2-methyl-1-azabicyclo[2.2.2]oct-3-yl]-2-cyclopropyl-1,3-benzothiazole-6-carboxamide; N-[(2S,3R)-2-methyl-1-azabicyclo[2.2.2]oct-3-yl]-2-cyclopropyl-1,3-benzothiazole-5-carboxamide; N-[(2S,3R)-2-methyl-1-azabicyclo[2.2.2]oct-3-yl]-2-methyl-1,3-benzothiazole-6-carboxamide; N-[(2S,3R)-2-methyl-1-azabicyclo[2.2.2]oct-3-yl]-2-methyl-1,3-benzothiazole-5-carboxamide; N-[(2S,3R)-2-methyl-1-azabicyclo[2.2.2]oct-3-yl]-2-ethyl-1,3-benzothiazole-6-carboxamide; N-[(2S,3R)-2-methyl-1-azabicyclo[2.2.2]oct-3-yl]-2-ethyl-1,3-benzothiazole-5-carboxamide, N-[(2S,3R)-2-methyl-1-azabicyclo[2.2.2]oct-3-yl]-2-methyl-1,3-benzodioxole-5-carboxamide; N-[(2S,3R)-2-methyl-1-azabicyclo[2.2.2]oct-3-yl]-2-ethyl-1,3-benzodioxole-5-carboxamide; N-[(2S,3R)-2-methyl-1-azabicyclo[2.2.2]oct-3-yl]-2,2-dimethyl-1,3-benzodioxole-5-carboxamide; N-[(2S,3R)-2-methyl-1-azabicyclo[2.2.2]oct-3-yl]-2-benzofuran-5-carboxamide; N-[(2S,3R)-2-methyl-1-azabicyclo[2.2.2]oct-3-yl]-2H-isoindole-5-carboxamide; N-[(2S,3R)-2-methyl-1-azabicyclo[2.2.2]oct-3-yl]-1H-benzimidazole-5-carboxamide; N-[(2S,3R)-2-methyl-1-azabicyclo[2.2.2]oct-3-yl][1,3]thiazolo[5,4-c]pyridine-6-carboxamide; N-[(2S,3R)-2-methyl-1-azabicyclo[2.2.2]oct-3-yl][1,3]thiazolo[4,5-c]pyridine-6-carboxamide; N-[(2S,3R)-2-methyl-1-azabicyclo[2.2.2]oct-3-yl][1,3]dioxolo[4,5-c]pyridine-6-carboxamide; N-[(2S,3R)-2-methyl-1-azabicyclo[2.2.2]oct-3-yl][1,3]oxazolo[4,5-c]pyridine-6-carboxamide; N-[(2S,3R)-2-methyl-1-azabicyclo[2.2.2]oct-3-yl]-1H-imidazo4,5-c]pyridine-6-carboxamide; or a pharmaceutically acceptable salt thereof.

34. The method according to claim 24, wherein the compound of Formula I has the S stereochemistry at C3 of quinuclidine.

35. The method according to claim 34, wherein the compound of Formula I includes N-((3S)-1-azabicyclo[2.2.2]oct-3-yl)-1,3-benzoxazole-6-carboxamide; N-((3S)1-azabicyclo[2.2.2]oct-3-yl)-2-methyl-1,3-benzoxazole-6-carboxamide; N-((3S)1-azabicyclo[2.2.2]oct-3-yl)-1,3-benzoxazole-5-carboxamide; N-((3S)1-azabicyclo[2.2.2]oct-3-yl)-2-methyl-1,3-benzoxazole-5-carboxamide; N-((3S)1-azabicyclo[2.2.2]oct-3-yl)-1,3-benzothiazole-6-carboxamide; N-((3S)1-azabicyclo[2.2.2]oct-3-yl)indane-5-carboxamide; N-((3S)-1-azabicyclo[2.2.2]oct-3-yl)-1,3-benzodioxole-5-carboxamide; N-[(3S)-1-azabicyclo[2.2.2]oct-3-yl][1,3]oxazolo[5,4-c]pyridine-6-carboxamide; N-[(3S)-1-azabicyclo[2.2.2]oct-3-yl]-2-benzoisothiophene-5-carboxamide; N-[(3S)-1-azabicyclo[2.2.2]oct-3-yl]-1,3-benzothiazole-5-carboxamide; N-[(3S)-1-azabicyclo[2.2.2]oct-3-yl]-3-methyl-1,2-benzisoxazole-6-carboxamide; N-[(3S)-1-azabicyclo[2.2.2]oct-3-yl]-3-methyl-1,2-benzisoxazole-5-carboxamide; N-[(3S)-1-azabicyclo[2.2.2]oct-3-yl]-1H-indazole-6-carboxamide; or a pharmaceutically acceptable salt thereof.

36. A method for treating schizophrenia in a mammal in need thereof wherein the cognitive and attention deficits associated with schizophrenia are treated and comprising administering to the mammal a therapeutically effective amount of compound according to Formula I:

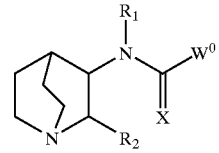

Formula I wherein W⁰ is a bicyclic moiety and is

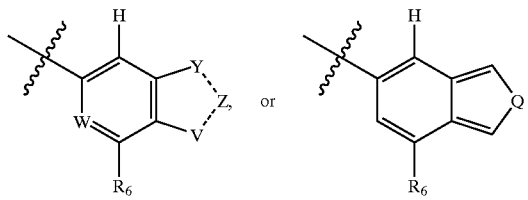

X is O, or S;

R₁ is H, alkyl, cycloalkyl, halogenated alkyl, substituted phenyl, or substituted naphthyl;

$R_2$ is H, alkyl, halogenated alkyl, substituted alkyl, cycloalkyl, or aryl;

$R_3$ is H, F, alkyl, halogenated alkyl, substituted alkyl, lactam heterocycloalkyl, phenoxy, substituted phenoxy, $R_7$, $R_9$, —N($R_4$)-aryl, —O-substituted phenyl, —O-substituted naphthyl, —S-substituted phenyl, —S-substituted naphthyl, alkyl substituted on the ω carbon with naphthyl, or alkyl substituted on the ω carbon with substituted naphthyl;

W is C(H) where

V—Z—Y is selected from O—C($R_3$)=N, O—C($R_5$)($R_3$)—N($R_4$), O—C($R_5$)($R_3$)—S, O—N=C($R_5$), O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_5$), N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)$_2$=N—O, C($R_5$)=N—S, C($R_5$)=N—N($R_4$), C($R_5$)$_2$—O—C($R_5$)$_2$, C($R_5$)$_2$—S—C($R_5$)$_2$, C($R_5$)$_2$—N($R_4$)—C($R_5$)$_2$, or C($R_5$)$_2$—C($R_3$)($R_5$)—C($R_5$)$_2$;

Q is N($R_{19}$), O, or S;

W is N where

V—Z—Y is selected from O—C($R_3$)=N, O—C($R_5$)($R_3$)—N($R_4$), O—C($R_5$)($R_3$)—S, O—N=C($R_5$) O—C($R_3$)($R_5$)—O, S—C($R_3$)=N, S—C($R_5$)($R_3$)—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)($R_3$)—O, N($R_4$)—C($R_5$)($R_3$)—S, N($R_4$)—C($R_5$)($R_3$)—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)=C($R_3$)—C($R_5$)$_2$, or C($R_5$)$_2$—C($R_3$)($R_5$)—C($R_5$)$_2$;

$R_4$ is H, or alkyl;

$R_5$ is H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)NH$_2$, —C(O)N(R$_{16}$)$_2$, —NHR$_1$, —NR$_1$COR$_{16}$, —N(R$_{10}$)$_2$, —SR$_1$, —C(O)R$_{16}$, —CO$_2$R$_1$, aryl, $R_7$, or $R_9$;

$R_6$ is H, F, Cl, Br, I, —CN, —CF$_3$, —OR$_{16}$, —SR$_{16}$, or —N(R$_{16}$)$_2$;

$R_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from $R_{20}$ and further having 0–3 substituents independently selected from F, Cl, Br, or I, or $R_7$ is 9-membered fused-ring moieties having a 6-membered ring fused to a 5-membered ring and having the formula

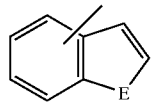

wherein E is O, S, or NR$_{19}$,

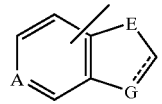

wherein E and G are independently selected from CR$_{18}$, O, S, N, or NR$_{19}$, and A is CR$_{18}$ or N, or

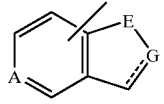

wherein E and G are independently selected from CR$_{18}$, O, S, N, or NR$_{19}$, and A is CR$_{18}$ or N, each 9-membered fused-ring moiety having 0–1 substituent selected from $R_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each $R_8$ is independently F, Br, Cl, I, alkyl, substituted alkyl, halogenated alkyl, alkenyl, substituted alkenyl, halogenated alkenyl, alkynyl, substituted alkynyl, halogenated alkynyl, —CN, —CF$_3$, —OR$_1$, —C(O)NH$_2$, —NHR$_1$, —SR$_1$, —CO$_2$R$_1$, aryl, phenoxy, substituted phenoxy, heteroaryl, —N(R$_4$)-aryl, or —O-substituted aryl.

$R_9$ is 6-membered heteroaromatic mono-cyclic moieties containing within the ring 1–3 heteroatoms selected from =N— and having 0–1 substituent selected from $R_{20}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{20}$ and 0–3 substituent(s) independently selected from F, Cl, Br, or I and having a bond directly or indirectly attached to the core molecule where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently H, alkyl, cycloalkyl, heterocyclo-alkyl, halogenated alkyl, halogenated cycloalkyl, or halogenated heterocycloalkyl;

$R_{13}$ is —OR$_{11}$, —SR$_{11}$, —NR$_{11}$R$_{11}$, —C(O)R$_{11}$, —C(O)NR$_{11}$R$_{11}$, —CN, —CF$_3$, —NR$_{11}$C(O)R$_{11}$, —S(O)$_2$NR$_{11}$R$_{11}$, —NR$_{11}$S(O)$_2$R$_{11}$, or —NO$_2$;

$R_{15}$ is aryl, $R_7$, or $R_9$;

$R_{16}$ is H, alkyl, substituted alkyl, cycloalkyl, halogenated alkyl, heterocycloalkyl, substituted heterocycloalkyl, substituted phenyl, or substituted naphthyl;

Each $R_{18}$ is independently selected from H, F, Cl, Br, I, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

R$_{19}$ is H, alkyl, halogenated alkyl, substituted alkyl, cycloalkyl, halogenated cycloalkyl, substituted cycloalkyl, phenyl, or phenyl having 1 substituent selected from R$_{20}$ and further having 0–3 substituents independently selected from F. Cl, Br, or I;

R$_{20}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or R$_{13}$, cycloalkyl substituted with 1–4 substituent(s) independently selected from F, Cl, Br, I, or R$_{13}$, or heterocycloalkyl substituted with 1–4 substituent(s) independently selected from F, Cl, Br, I, or R$_{13}$;

Each R$_{22}$ is independently H, alkyl, substituted alkyl, cycloalkyl, halogenated alkyl, substituted cycloalkyl, heterocycloalkyl, or substituted heterocycloalkyl;

or pharmaceutically acceptable salt, or racemic mixture thereof.

37. The method according to claim 36, wherein X is O.
38. The method according to claim 37, wherein R$_1$ is H.
39. The method according to claim 38, wherein R$_2$ is H.
40. The method according to claim 39, wherein W$^0$ includes 1,3-benzoxazol-6-yl, 1,3-benzoxazol-5-yl, 1,3-benzothiazol-6-yl, indan-5-yl, 1,3-benzodioxol-5-yl, [1,3]oxazolo[5,4-c]pyridin-6-yl, 2-benzoisothiophen-5-yl, 1,3-benzothiazol-5-yl, 1,2-benzothiazol-6-yl, 1,2-benzisoxazol-5-yl, or 1H-indazol-6-yl, optionally substituted with F, Br, Cl, alkyl, halogenated alkyl, substituted alky, alkenyl, substituted alkenyl, halogenated alkenyl, alkynyl, substituted alkynyl, halogenated alkynyl, heterocycloalkyl, substituted heterocycloalkyl, lactam heterocycloalkyl, phenoxy, substituted phenoxy, —CF$_3$, —CN, —NO$_2$, —OR$_1$, —OR$_{22}$, —NHR$_1$, —N(R$_{10}$)$_2$, —N(R$_{22}$)$_2$, —N(R$_4$)-arly, —SR$_1$, —$_{22}$, —C(O)N(R$_{16}$)$_2$, —NR$_1$COR$_{16}$.

41. The method according to claim 38, wherein R$_2$ is alkyl, halogenated alkyl, substituted alkyl, cycloalkyl, or aryl, and wherein W$^0$ includes 1,3-benzoxazol-6-yl, 1,3-benzoxazol-5-yl, 1,3-benzothiazol-6-yl, indan-5-yl, 1,3-benzodioxol-5-yl, [1,3]oxazolo[5,4-c]pyridin-6-yl, 2-benzoisothiophen-5-yl, 1,3-benzothiazol-5-yl, 1,2-benzothiazol-6-yl, 1,2-benzisoxazol-5-yl, or 1H-indazol-6-yl, optionally substituted with F, Br, Cl, alkyl, halogenated alkyl, substituted alky, alkenyl, substituted alkenyl, halogenated alkenyl, alkynyl, substituted alkynyl, halogenated alkynyl, heterocycloalkyl, substituted heterocycloalkyl, lactam heterocycloalkyl, phenoxy, substituted phenoxy, —CF$_3$, —CN, —NO$_2$, —OR$_1$, —OR$_{22}$, —NHR$_1$, —N(R$_{10}$)$_2$, —N(R$_{22}$)$_2$, —N(R$_4$)-aryl, —SR$_1$, —SR$_{22}$, —C(O)N(R$_{16}$)$_2$, or —NR$_1$COR$_{16}$.

42. The method according to claim 41, wherein R$_2$ is alkyl, halogenated alkyl, substituted alkyl.
43. The method according to claim 36, wherein the compound of Formula I has the R stereochemistry at C3 of quinuclidine.
44. The method according to claim 43, wherein the compound of Formula I includes N-((3R)-1-azabicyclo[2.2.2]oct-3-yl)-1,3-benzoxazole-6-carboxamide; N-((3R)1-azabicyclo[2.2.2]oct-3-yl)-2-methyl-1,3-benzoxazole-6-carboxamide; N-((3R)1-azabicyclo[2.2.2]oct-3-yl)-1,3-benzoxazole-5-carboxamide; N-((3R)1-azabicyclo[2.2.2]oct-3-yl)-2-methyl-1,3-benzoxazole-5-carboxamide; N-((3R)1-azabicyclo[2.2.2]oct-3-yl)-1,3-benzothiazole-6-carboxamide; N-((3R)1-azabicyclo[2.2.2]oct-3-yl)indane-5-carboxamide; N-((3R)-1-azabicyclo[2.2.2]oct-3-yl)-1,3-benzodioxole-5-carboxamide; N-[(3R)-1-azabicyclo[2.2.2]oct-3-yl][1,3]oxazolo[5,4-c]pyridine-6-carboxamide; N-[(3R)-1-azabicyclo[2.2.2]oct-3-yl]-2-benzoisothiophene-5-carboxamide; N-[(3R)-1-azabicyclo[2.2.2]oct-3-yl]-1,3-benzothiazole-5-carboxamide; N-[(3R)-1-azabicyclo[2.2.2]oct-3-yl]-3-methyl-1,2-benzisoxazole-6-carboxamide; N-[(3R)-1-azabicyclo[2.2.2]oct-3-yl]-3-methyl-1,2-benzisoxazole-5-carboxamide; N-[(3R)-1-azabicyclo[2.2.2]oct-3-yl]-1H-indazole-6-carboxamide; N-((2S,3R)-2-methyl-1-azabicyclo[2.2.2]oct-3-yl)-1,3-benzoxazole-6-carboxamide; N-((2S,3R)-2-methyl-1-azabicyclo[2.2.2]oct-3-yl)-2-methyl-1,3-benzoxazole-6-carboxamide; N-((2S,3R)-2-methyl-1-azabicyclo[2.2.2]oct-3-yl)-1,3-benzoxazole-5-carboxamide; N-((2S,3R)-2-methyl-1-azabicyclo[2.2.2]oct-3-yl)-2-methyl-1,3-benzoxazole-5-carboxamide; N-((2S,3R)-2-methyl-1-azabicyclo[2.2.2]oct-3-yl)-1,3-benzothiazole-6-carboxamide; N-((2S,3R)-2-methyl-1-azabicyclo[2.2.2]oct-3-yl)indane-5-carboxamide; N-((2S,3R)-2-methyl-1-azabicyclo[2.2.2]oct-3-yl)-1,3-benzodioxole-5-carboxamide; N-[(2S,3R)-2-methyl-1-azabicyclo[2.2.2]oct-3-yl][1,3]oxazolo[5,4-c]pyridine-6-carboxamide; N-[(2S,3R)-2-methyl-1-azabicyclo[2.2.2]oct-3-yl]-2-benzoisothiophene-5-carboxamide; N-[(2S,3R)-2-methyl-1-azabicyclo[2.2.2]oct-3-yl]-1,3-benzothiazole-5-carboxamide; N-[(2S,3R)-2-methyl-1-azabicyclo[2.2.2]oct-3-yl]-3-methyl-1,2-benzisoxazole-6-carboxamide; N-[(2S,3R)-2-methyl-1-azabicyclo[2.2.2]oct-3-yl]-3-methyl-1,2-benzisoxazole-5-carboxamide; N-[(2S,3R)-2-methyl-1-azabicyclo[2.2.2]oct-3-yl]-1H-indazole-6-carboxamide; or a pharmaceutically acceptable salt thereof.

45. The method according to claim 43, wherein the compound of Formula I includes N-[(3R)-1-azabicyclo[2.2.2]oct-3-yl]-1H-indazole-5-carboxamide; N-[(3R)-1-azabicyclo[2.2.2]oct-3-yl]-3-methyl-1H-indazole-6-carboxamide; N-[(3R)-1-azabicyclo[2.2.2]oct-3-yl]-3-methyl-1H-indazole-5-carboxamide; N-[(3R)-1-azabicyclo[2.2.2]oct-3-yl]-3-ethyl-1H-indazole-6-carboxamide; N-[(3R)-1-azabicyclo[2.2.2]oct-3-yl]-3-ethyl-1H-indazole-5-carboxamide; N-[(3R)-1-azabicyclo[2.2.2]oct-3-yl]-1,2-benzisothiazole-6-carboxamide; N-[(3R)-1-azabicyclo[2.2.2]oct-3-yl]-1,2-benzisothiazole-5-carboxamide; N-[(3R)-1-azabicyclo[2.2.2]oct-3-yl]-3-ethyl-1,2-benzisothiazole-6-carboxamide; N-[(3R)-1-azabicyclo[2.2.2]oct-3-yl]-3-ethyl-1,2-benzisothiazole-5-carboxamide; N-[(3R)-1-azabicyclo[2.2.2]oct-3-yl]-3-methyl-1,2-benzisothiazole-6-carboxamide; N-[(3R)-1-azabicyclo[2.2.2]oct-3-yl]-3-methyl-1,2-benzisothiazole-5-carboxamide; N-[(3R)-1-azabicyclo[2.2.2]oct-3-yl]-2-cyclopropyl-1,3-benzoxazole-6-carboxamide; N-[(3R)-1-azabicyclo[2.2.2]oct-3-yl]-2-cyclopropyl-1,3-benzoxazole-5-carboxamide; N-[(3R)-1-azabicyclo[2.2.2]oct-3-yl]-2-cyclopropyl-1,3-benzothiazole-6-carboxamide; N-[(3R)-1- azabicyclo[2.2.2]oct-3-yl]-2-cyclopropyl-1,3-benzothiazole-5-carboxamide; N-[(3R)-1-azabicyclo[2.2.2]oct-3-yl]-2-methyl-1,3-benzothiazole-6-carboxamide; N-[(3R)-1-azabicyclo[2.2.2]oct-3-yl]-2-methyl-1,3-benzothiazole-5-carboxamide; N-[(3R)-1-azabicyclo[2.2.2]oct-3-yl]-2-ethyl-1,3-benzothiazole-6-carboxamide; N-[(3R)-1-azabicyclo[2.2.2]oct-3-yl]-2-ethyl-1,3-benzothiazole-5-carboxamide; N-[(3R)-1-azabicyclo[2.2.2]oct-3-yl]-2-methyl-1,3-benzodioxole-5-carboxamide; N-[(3R)-1-azabicyclo[2.2.2]oct-3-yl]-2-ethyl-1,3-benzodioxole-5-carboxamide; N-[(3R)-1-azabicyclo[2.2.2]oct-3-yl]-2,2-dimethyl-1,3-benzodioxole-5-carboxamide; N-[(3R)-1-azabicyclo[2.2.2]oct-3-yl]-2-benzofuran-5-carboxamide; N-[(3R)-1-azabicyclo[2.2.2]oct-3-yl]-2H-isoindole-5-carboxamide; N-[(3R)-1-azabicyclo[2.2.2]oct-3-yl]-1H-benzimidazole-5-carboxamide; N-[(3R)-1-azabicyclo[2.2.2]oct-3-yl][1,3]thiazolo[5,4-c]pyridine-6-carboxamide; N-[(3R)-1-azabicyclo[2.2.2]oct-3-yl][1,3]thiazolo[4,5-c]pyridine-6-carboxamide; N-[(3R)-1-azabicyclo[2.2.2]oct-3-yl][1,3]dioxolo[4,5-c]pyridine-6-carboxamide; N-[(3R)-1-azabicyclo[2.2.2]oct-3-yl][1,3]oxazolo[4,5-c]pyridine-6-carboxamide; N-[(3R)-1-azabicyclo[2.2.2]oct-3-yl]-1H-imidazo[4,5-c]pyridine-6-carboxamide;

N-[(2S,3R)-2-methyl-1-azabicyclo[2.2.2]oct-3-yl]-1H-indazole-6-carboxamide; N-[(2S,3R)-2-methyl-1-azabicyclo[2.2.2]oct-3-yl]-1H-indazole-5-carboxamide; N-[(2S,3R)-2-methyl-1-azabicyclo[2.2.2]oct-3-yl]-3-methyl-1H-indazole-6-carboxamide; N-[(2S,3R)-2-methyl-1-azabicyclo[2.2.2]oct-3-yl]-3-methyl-1H-indazole-5-carboxamide; N-[(2S,3R)-2-methyl-1-azabicyclo[2.2.2]oct-3-yl]-3-ethyl-1H-indazole-6-carboxamide ; N-[(2S,3R)-2-methyl-1-azabicyclo[2.2.2]oct-3-yl]-3-ethyl-1H-indazole-5-carboxamide ; N-[(2S,3R)-2-methyl-1-azabicyclo[2.2.2]oct-3-yl]-1,2-benzisothiazole-6-carboxamide; N-[(2S,3R)-2-methyl-1-azabicyclo[2.2.2]oct-3-yl]-1,2-benzisothiazole-5-carboxamide; N-[(2S,3R)-2-methyl-1-azabicyclo[2.2.2]oct-3-yl]-3-ethyl-1,2-benzisothiazole-6-carboxamide; N-[(2S,3R)-2-methyl-1-azabicyclo[2.2.2]oct-3-yl]-3-ethyl-1,2-benzisothiazole-5-carboxamide; N-[(2S,3R)-2-methyl-1-azabicyclo[2.2.2]oct-3-yl]-3-methyl-1,2-benzisothiazole-6-carboxamide; N-[(2S,3R)-2-methyl-1-azabicyclo[2.2.2]oct-3-yl]-3-methyl-1,2-benzisothiazole-5-carboxamide; N-[(2S,3R)-2-methyl-1-azabicyclo[2.2.2]oct-3-yl]-2-cyclopropyl-1,3-benzoxazole-6-carboxamide; N-[(2S,3R)-2-methyl-1-azabicyclo[2.2.2]oct-3-yl]-2-cyclopropyl-1,3-benzoxazole-5-carboxamide; N-[(2S,3R)-2-methyl-1-azabicyclo[2.2.2]oct-3-yl]-2-cyclopropyl-1,3-benzothiazole-6-carboxamide; N-[(2S,3R)-2-methyl-1-azabicyclo[2.2.2]oct-3-yl]-2-cyclopropyl-1,3-benzothiazole-5-carboxamide; N-[(2S,3R)-2-methyl-1-azabicyclo[2.2.2]oct-3-yl]-2-methyl-1,3-benzothiazole-6-carboxamide; N-[(2S,3R)-2-methyl-1-azabicyclo[2.2.2]oct-3-yl]-2-methyl-1,3-benzothiazole-5-carboxamide; N-[(2S,3R)-2-methyl-1-azabicyclo[2.2.2]oct-3-yl]-2-ethyl-1,3-benzothiazole-6-carboxamide; N-[(2S,3R)-2-methyl-1-azabicyclo[2.2.2]oct-3-yl]-2-ethyl-1,3-benzothiazole-5-carboxamide; N-[(2S,3R)-2-methyl-1-azabicyclo[2.2.2]oct-3-yl]-2-methyl-1,3-benzodioxol-5-carboxamide; N-[(2S,3R)-2-methyl-1-azabicyclo[2.2.2]oct-3-yl]-2-ethyl-1,3-benzodioxole-5-carboxamide; N-[(2S,3R)-2-methyl-1-azabicyclo[2.2.2]oct-3-yl]-2,2-dimethyl-1,3-benzodioxole-5-carboxamide; N-[(2S,3R)-2-methyl-1-azabicyclo[2.2.2]-oct-3-yl]-2-benzofuran-5-carboxamide; N-[(2S,3R)-2-methyl-1-azabicyclo[2.2.2oct-3-yl]-2H-isoindole-5-carboxamide; N-[(2,3R)-2-methyl-1-azabicyclo[2.2.2]oct-3-yl]-1H-benzimidazole-5-carboxamide; N-[(2S,3R)-2-methyl-1-azabicyclo[2.2.2]oct-3-yl][1,3]thiazolo[5,4-c]pyridine-6-carboxamide; N-[(2S,3R)-2-methyl-1-azabicyclo[2.2.2]oct-3-yl][1,3]thiazolo[4,5-c]pyridine-6-carboxamide; N-[(2S,3R)-2-methyl-1-azabicyclo[2.2.2]oct-3-yl][1,3]dioxolo[4,5-c]pyridine-6-carboxamide; N-[(2S,3R)-2-methyl-1-azabicyclo[2.2.2]oct-3-yl][1,3]oxazolo[4,5-c]pyridine-6-carboxamide; N-[(2S,3R)-2-methyl-1-azabicyclo[2.2.2]oct-3-yl]-1H-imidazo]4,5-c]pyridine-6-carboxamide; or a pharmaceutically acceptable salt thereof.

46. The method according to claim 36, wherein the compound of Formula I has the S stereochemistry at C3 of quinuclidine.

47. The method according to claim 68, wherein the compound of Formula I includes N-((3S)-1-azabicyclo[2.2.2]oct-3-yl)-1,3-benzoxazole-6-carboxamide; N-((3S)1-azabicyclo[2.2.2]oct-3-yl)-2-methyl-1,3-benzoxazole-6-carboxamide; N-((3S)-1-azabicyclo[2.2.2]oct-3-yl)-1,3-benzoxazole-5-carboxamide; N-((3S)1-azabicyclo[2.2.2]oct-3-yl)-2-methyl-1,3-benzoxazole-5-carboxamide; N-((3S)1-azabicyclo[2.2.2]oct-3-yl)-1,3-benzothiazole-6-carboxamide; N-((3S)1-azabicyclo[2.2.2]oct-3-yl)indane-5-carboxamide; N-((3S)-1-azabicyclo[2.2.2]oct-3-yl)-1,3-benzodioxole-5-carboxamide; N-[(3S)-1-azabicyclo[2.2.2]oct-3-yl][1,3]oxazolo[5,4-c]pyridine-6-carboxamide; N-[(3S)-1-azabicyclo[2.2.2]oct-3-yl]-2-benzoisothiophene-5-carboxamide; N-[(3S)-1-azabicyclo[2.2.2]oct-3-yl]-1,3-benzothiazole-5-carboxamide; N-[(3S)-1-azabicyclo[2.2.2]oct-3-yl]-3-methyl-1,2-benzisoxazole-6-carboxamide; N-[(3S)-1-azabicyclo[2.2.2]oct-3-yl]-3-methyl-1,2-benzisoxazole-5-carboxamide; N-[(3S)-1-azabicyclo[2.2.2]oct-3-yl]-1H-indazole-6-carboxamide; or a pharmaceutically acceptable salt thereof.

48. A pharmaceutical composition comprising a compound according to claim 43.

49. The pharmaceutical composition according to claim 48, wherein said pharmaceutical composition is to be administered rectally, topically, orally, sublingually, or parenterally.

50. The pharmaceutical composition according to claim 49, wherein said compound is administered in an amount of from about 0.001 to about 100 mg/kg of body weight of said mammal per day.

51. The pharmaceutical composition according to claim 50, wherein said compound is administered in an amount of from about 0.1 to about 50 mg/kg of body weight of said mammal per day.

52. A pharmaceutical composition comprising a compound according to claim 43 and an anti-psychotic agent.

53. The pharmaceutical composition according to claim 52, wherein said compound and said agent are to be independently administered rectally, topically, orally, sublingually, or parenterally for a therapeutically effective interval.

54. The pharmaceutical composition according to claim 53, wherein said compound is administered in an amount of from about 0.001 to about 100 mg/kg of body weight of said mammal per day.

55. The pharmaceutical composition according to claim 53, wherein said compound is administered in an amount of from about 0.1 to about 50 mg/kg of body weight of said mammal per day.

56. A pharmaceutical composition comprising a compound according to claim 46.

57. The pharmaceutical composition according to claim 56, wherein said pharmaceutical composition is to be administered rectally, topically, orally, sublingually, or parenterally.

58. The pharmaceutical composition according to claim 57, wherein said compound is administered in an amount of from about 0.001 to about 100 mg/kg of body weight of said mammal per day.

59. The pharmaceutical composition according to claim 57, wherein said compound is administered in an amount of from about 0.1 to about 50 mg/kg of body weight of said mammal per day.

60. A pharmaceutical composition comprising a compound according to claim 46 and an anti-psychotic agent.

61. The pharmaceutical composition according to claim 59, wherein said compound and said agent are to be independently administered rectally, topically, orally, sublingually, or parenterally for a therapeutically effective interval.

62. The pharmaceutical composition according to claim 61, wherein said compound is administered in an amount of from about 0.001 to about 100 mg/kg of body weight of said mammal per day.

63. The pharmaceutical composition according to claim 61, wherein said compound is administered in an amount of from about 0.1 to about 50 mg/kg of body weight of said mammal per day.

\* \* \* \* \*